US012714758B2

(12) United States Patent
Larson et al.

(10) Patent No.: US 12,714,758 B2
(45) Date of Patent: Aug. 25, 2026

(54) DOTA-HAPTEN COMPOSITIONS FOR ANTI-DOTA/ANTI-TUMOR ANTIGEN BISPECIFIC ANTIBODY PRETARGETED RADIOIMMUNOTHERAPY

(71) Applicant: Memorial Sloan Kettering Cancer Center, New York, NY (US)

(72) Inventors: Steven Larson, New York, NY (US); Darren Veach, New York, NY (US); Sarah Taldone, New York, NY (US); Ouathek Ouerfelli, New York, NY (US); Guangbin Yang, New York, NY (US); Nai-Kong Cheung, New York, NY (US); Brian Santich, New York, NY (US); Hong Xu, New York, NY (US)

(73) Assignee: Memorial Sloan Kettering Cancer Center, New York, NY (US)

(*) Notice: Subject to any disclaimer, the term of this patent is extended or adjusted under 35 U.S.C. 154(b) by 876 days.

(21) Appl. No.: 18/003,659

(22) PCT Filed: Jun. 28, 2021

(86) PCT No.: PCT/US2021/039423
§ 371 (c)(1),
(2) Date: Dec. 28, 2022

(87) PCT Pub. No.: WO2022/005998
PCT Pub. Date: Jan. 6, 2022

(65) Prior Publication Data

US 2023/0256121 A1 Aug. 17, 2023

Related U.S. Application Data

(60) Provisional application No. 63/045,632, filed on Jun. 29, 2020.

(51) Int. Cl.
*A61K 51/04* (2006.01)
*A61K 47/68* (2017.01)
*A61K 51/06* (2006.01)

(52) U.S. Cl.
CPC ........ *A61K 51/065* (2013.01); *A61K 47/6893* (2017.08); *A61K 51/0497* (2013.01)

(58) Field of Classification Search
CPC .............................. A61K 51/04; A61K 51/065
See application file for complete search history.

(56) References Cited

U.S. PATENT DOCUMENTS

| | | | |
|---|---|---|---|
| 2010/0254987 A1 | 10/2010 | Davis et al. | |
| 2019/0038671 A1 | 2/2019 | Fan et al. | |
| 2019/0177345 A1 | 6/2019 | Larsen | |
| 2019/0388473 A1 | 12/2019 | Mata-Fink et al. | |
| 2020/0140543 A1 | 5/2020 | Cheal et al. | |

FOREIGN PATENT DOCUMENTS

| | | | |
|---|---|---|---|
| WO | WO-2015/091130 A1 | 6/2015 | |
| WO | WO-2018/200562 A1 | 11/2018 | |
| WO | WO-2019/006465 A1 | 1/2019 | |
| WO | WO-2019010299 A1 * | 1/2019 | ......... A61K 47/6879 |
| WO | WO-2019/157037 A1 | 8/2019 | |
| WO | WO-2019/177970 A1 | 9/2019 | |
| WO | WO-2019/209991 A1 | 10/2019 | |
| WO | WO-2020/219715 A1 | 10/2020 | |

OTHER PUBLICATIONS

International Search Report and Written Opinion on PCT PCT/US2021/039409 Dtd Oct. 26, 2021.
International Search Report and Written Opinion on PCT PCT/US2021/039418 Dtd Oct. 27, 2021.
International Search Report and Written Opinion on PCT PCT/US2021/039420 Dtd Dec. 13, 2021.
International Search Report on PCT PCT/US2021/039423 Dtd Sep. 29, 2021.
Krebs et al., "Antibody with Infinite Affinity for In Vivo Tracking of Genetically Engineered Lymphocytes," Dec. 2018, vol. 59, No. 12, (8, pages).
Orozco Johnnie J et al., "Novel Bispecific Antibody Targeting CD45 and 90 Y-DOTA Is Effective Therapy for Acute Myeloid Leukemia in Preclinical Murine Models", , Jan. 1, 2017 (Jan. 1, 2017), XP093170748, DOI: 10.1182/blood.V130.Suppl_ 1.1355.1355.
Krebs et al., "Imaging of CAR T-Cells in Cancer Patients: Paving the Way to Treatment Monitoring and Outcome Prediction", J. Nucl. Med., online May 3, 2019, 60: 879-881.
Mah et al., Biological Target vol. CAR T-Cell Oncologic Imaging, 2008, Abstract 2 pages.
Unknown, Sequence Alignment, Search Completed Feb. 25, 2026, 1 page.

* cited by examiner

*Primary Examiner* — Michael G. Hartley
*Assistant Examiner* — Jagadishwar R Samala
(74) *Attorney, Agent, or Firm* — Foley & Lardner LLP

(57) ABSTRACT

The present disclosure provides compositions and methods for the detection and treatment of cancer. Specifically, the compositions of the present technology include novel compounds that may be complexed with a radioisotope. Also disclosed herein are methods of the using the DOTA-haptens of the present technology in diagnostic imaging as well as pretargeted radioimmunotherapy.

20 Claims, 14 Drawing Sheets

FIG. 2

| Organ | Pretargeted<br>[89Zr]DFO-PEG4-LuDOTA<br>SW1222-tumor bearing mice<br>(n = 3)<br>200 pmol/1.48 MBq [40 μCi]<br>4 h p.i. | Non-pretargeted<br>[89Zr]DFO-PEG4-LuDOTA<br>tumor-free mice<br>(n = 5)<br>215 pmol/1.59 MBq [43 μCi]<br>4 h p.i. |
|---|---|---|
| Blood | 0.92 ± 0.12 | 0.09 ± 0.02 |
| SW1222 tumor | 9.30 ± 2.88 | N/A |
| Heart | 0.29 ± 0.08 | 0.05 ± 0.02 |
| Lungs | 0.50 ± 0.07 | 0.20 ± 0.13 |
| Liver | 0.59 ± 0.06 | 0.39 ± 0.10 |
| Spleen | 0.27 ± 0.06 | 0.06 ± 0.01 |
| Stomach | 0.10 ± 0.06 | 0.39 ± 0.34 |
| Small Intestine | 0.24 ± 0.08 | 0.29 ± 0.33 |
| Large Intestine | 3.03 ± 0.89 | 1.90 ± 0.57 |
| Kidneys | 6.45 ± 0.85 | 8.78 ± 1.94 |
| Muscle | 0.17 ± 0.03 | 0.03 ± 0.01 |
| Bone | 0.11 ± 0.02 | 0.05 ± 0.01 |
| *Tumor (g)* | *0.673 ± 0.387* | |
| *Tumor-to-tissue ratios* | | |
| Blood | 10.1 ± 2.0 | |
| Heart | 31.7 ± 7.6 | |
| Lungs | 18.7 ± 3.6 | |
| Liver | 15.7 ± 2.9 | |
| Spleen | 34.4 ± 7.7 | |
| Stomach | 93.0 ± 37.4 | |
| Small Intestine | 38.2 ± 9.7 | |
| Large Intestine | 3.1 ± 0.8 | |
| Kidneys | 1.4 ± 0.3 | |
| Muscle | 53.7 ± 10.6 | |
| Bone | 82.1 ± 16.0 | |

FIG. 3

| Time post-injection (minutes) | n | %IA/g |
|---|---|---|
| 5 | 3 | 5.16 ± 0.84 |
| 30 | 3 | 1.26 ± 0.27 |
| 60 | 2 | 0.58 ± 0.10 |
| 120 | 2 | 0.17 ± 0.04 |
| 240 | 5 | 0.09 ± 0.02 |

FIG. 4

| Time post-injection (minutes) | n | %IA |
|---|---|---|
| 0 | 5 | 100 |
| 30 | 5 | 79.2 ± 19.7 |
| 120 | 5 | 20.4 ± 4.59 |

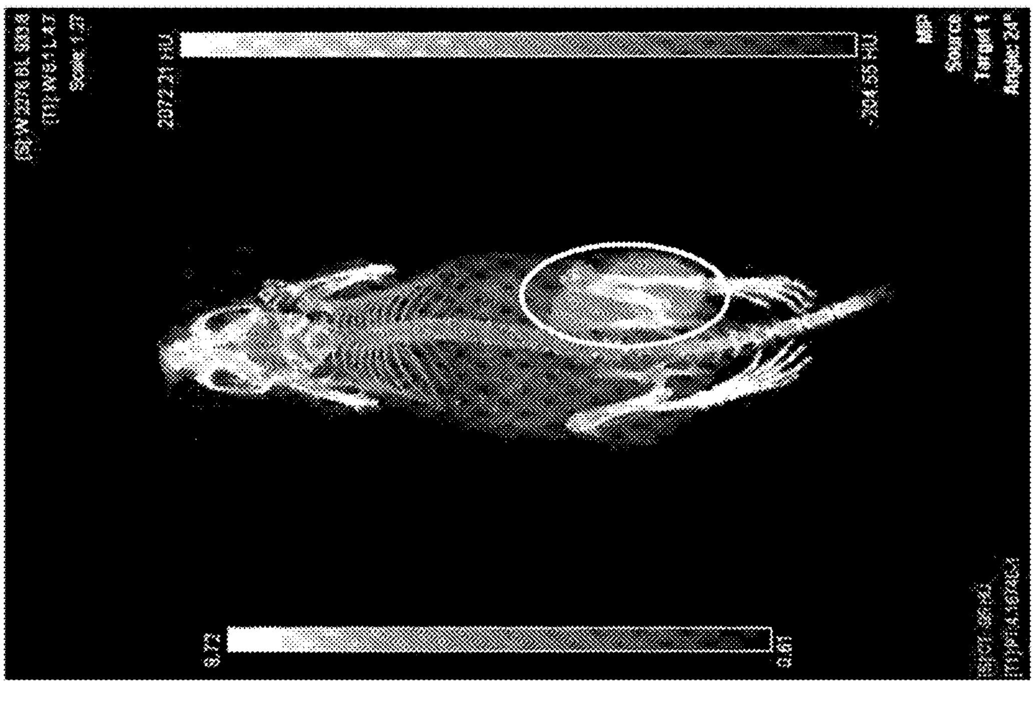
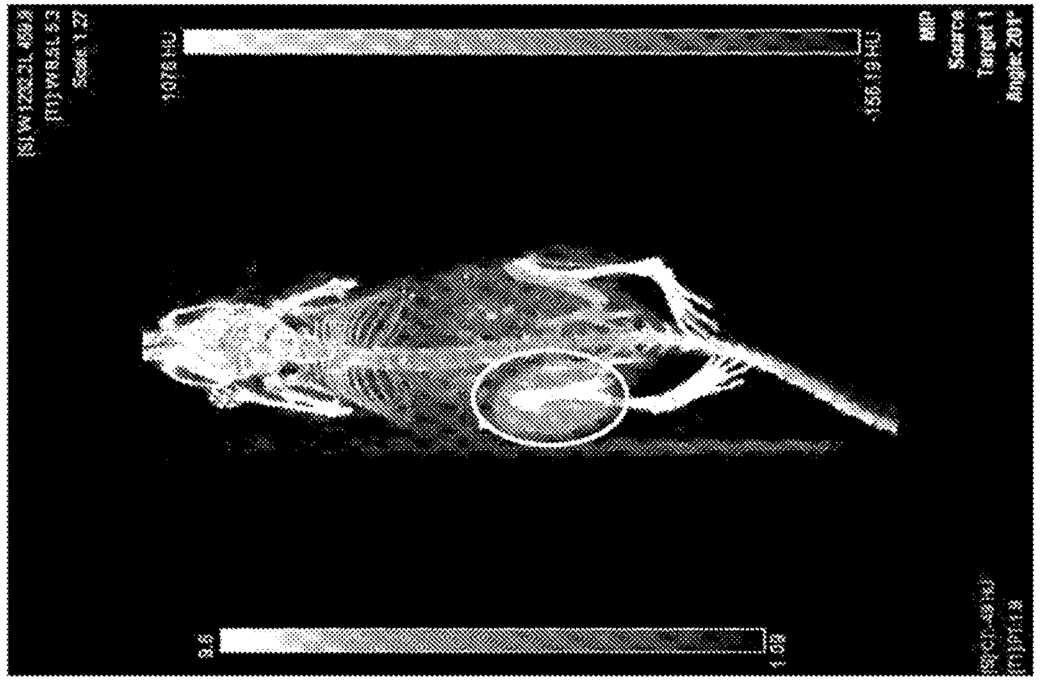
FIG. 5

FIG. 6

| Organ | Pretargeted $^{68}$Ga]NODAGA-PEG4-LuDOTA SW1222-tumor bearing mice (n = 3) 130 pmol/6.0 MBq [161 μCi] 1 h p.i. | Pretargeted $^{68}$Ga]DO3A-PEG4-LuDOTA SW1222-tumor bearing mice (n = 3) 337 pmol/4.1 MBq [112 μCi] 1 h p.i. |
|---|---|---|
| Blood | 1.29 ± 0.57 | 0.41 ± 0.23 |
| SW1222 tumor | 16.44 ± 4.75 | 1.91 ± 1.01 |
| Heart | 0.63 ± 0.27 | 0.19 ± 0.09 |
| Lungs | 0.99 ± 0.30 | 0.70 ± 0.71 |
| Liver | 0.99 ± 0.15 | 3.11 ± 2.88 |
| Spleen | 0.57 ± 0.11 | 0.91 ± 1.00 |
| Stomach | 0.13 ± 0.08 | 0.04 ± 0.01 |
| Small Intestine | 0.42 ± 0.19 | 0.06 ± 0.03 |
| Large Intestine | 0.11 ± 0.04 | 0.04 ± 0.02 |
| Kidneys | 1.23 ± 0.25 | 0.24 ± 0.14 |
| Muscle | 0.45 ± 0.34 | 0.04 ± 0.02 |
| Bone | 1.15 ± 0.73* | 0.45 ± 0.34 |
| *Tumor (g)* | *0.348 ± 0.190* | *0.352 ± 0.193* |
| *Tumor-to-tissue ratios* | | |
| Blood | 12.7 ± 3.9 | 4.6 ± 2.1 |
| Heart | 26.0 ± 7.8 | 10.0 ± 4.0 |
| Lungs | 16.6 ± 4.0 | 2.7 ± 1.8 |
| Liver | 16.6 ± 3.1 | 0.6 ± 0.4 |
| Spleen | 28.7 ± 5.7 | 2.1 ± 1.5 |
| Stomach | 123.3 ± 49.3 | 52.5 ± 16.6 |
| Small Intestine | 38.8 ± 12.0 | 30.1 ± 13.2 |
| Large Intestine | 149.5 ± 40.1 | 51.9 ± 24.7 |
| Kidneys | 13.4 ± 2.7 | 7.8 ± 3.5 |
| Muscle | 36.8 ± 17.2 | 51.2 ± 19.8 |
| Bone | 14.4 ± 6.9 | 4.3 ± 2.3 |

*with 5.02 %ID/g outlier not excluded 2.44 ± 2.30

FIG. 8

| Tissues | 5 min (n = 4) | 15 min (n = 4) | 30 min (n = 4) | 60 min (n = 4) |
|---|---|---|---|---|
| Blood | 3.80 ± 0.61 | 2.05 ± 0.70 | 0.90 ± 0.09 | 1.18 ± 0.16 |
| Heart | 1.08 ± 0.07 | 0.68 ± 0.23 | 0.32 ± 0.09 | 0.43 ± 0.07 |
| Lungs | 2.09 ± 0.21 | 1.39 ± 0.35 | 0.66 ± 0.16 | 0.66 ± 0.05 |
| Liver | 1.28 ± 0.30 | 0.97 ± 0.23 | 0.70 ± 0.01 | 0.57 ± 0.07 |
| Spleen | 0.67 ± 0.11 | 0.53 ± 0.11 | 0.30 ± 0.03 | 0.25 ± 0.06 |
| Stomach | 0.78 ± 0.47 | 0.24 ± 0.09 | 0.06 ± 0.02 | 0.10 ± 0.02 |
| Small Int. | 0.52 ± 0.12 | 0.37 ± 0.13 | 0.13 ± 0.05 | 0.13 ± 0.03 |
| Large Int. | 0.26 ± 0.07 | 0.16 ± 0.05 | 0.08 ± 0.04 | 0.09 ± 0.01 |
| Kidneys | 5.75 ± 1.35 | 2.86 ± 1.01 | 0.89 ± 0.13 | 0.95 ± 0.14 |
| Muscle | 0.75 ± 0.23 | 0.42 ± 0.19 | 0.17 ± 0.04 | 0.28 ± 0.06 |
| Bone | 0.57 ± 0.25 | 0.31 ± 0.09 | 0.13 ± 0.03 | 0.28 ± 0.12 |
| *Tumor* | *4.82 ± 2.26* | *8.21 ± 2.06** | *8.54 ± 0.72* | *9.73 ± 1.50* |
| *Tumor size (g)* | *0.518 ± 0.284* | *0.428 ± 0.299*** | *0.939 ± 0.126* | *0.918 ± 0.066* |
| *Tumor-to-tissue ratios* | | | | |
| Blood | 1.3 ± 0.3 | 4.0 ± 0.9 | 9.5 ± 0.6 | 8.3 ± 0.8 |
| Heart | 4.5 ± 1.1 | 12.1 ± 2.7 | 26.7 ± 3.9 | 22.7 ± 2.6 |
| Lungs | 2.3 ± 0.6 | 5.9 ± 1.1 | 12.9 ± 1.6 | 14.7 ± 1.3 |
| Liver | 3.8 ± 1.0 | 8.4 ± 1.6 | 12.2 ± 0.5 | 17.2 ± 1.7 |
| Spleen | 7.2 ± 1.8 | 15.6 ± 2.8 | 28.7 ± 2.0 | 38.5 ± 5.2 |
| Stomach | 6.2 ± 2.4 | 34.9 ± 8.2 | 136.6 ± 19.5 | 97.3 ± 14.1 |
| Small Int. | 9.4 ± 2.5 | 22.5 ± 5.1 | 64.4 ± 13.1 | 73.4 ± 10.5 |
| Large Int. | 18.5 ± 5.0 | 52.9 ± 11.0 | 110.2 ± 30.2 | 114.4 ± 11.1 |
| Kidneys | 0.8 ± 0.2 | 2.9 ± 0.7 | 9.6 ± 0.8 | 10.3 ± 1.1 |
| Muscle | 6.4 ± 1.8 | 19.4 ± 5.2 | 50.2 ± 6.6 | 35.4 ± 4.7 |
| Bone | 8.5 ± 2.7 | 26.3 ± 5.5 | 67.0 ± 8.3 | 34.4 ± 7.6 |

Without 0.0631 g outlier excluded 0.428 ± 0.299 g
Without 0.0631 g outlier excluded 6.68 ± 3.49 %IA/g

FIG. 10

| Organ | Pretargeted [$^{64}$Cu]NODAGA-PEG$_4$-LuDOTA SW1222-tumor bearing mice (n = 4) 150 pmol/1.9 MBq [51 µCi] 24 h p.i. | Pretargeted [$^{64}$Cu]NODAGA-PEG$_4$LuDOTA SW1222-tumor bearing mice (n = 1) 1000 pmol/11 MBq [300 µCi] 24 h p.i. |
|---|---|---|
| Blood | 0.22 ± 0.03 | 0.07 |
| SW1222 tumor | 3.53 ± 0.55 | 1.84 |
| Heart | 0.16 ± 0.04 | 0.06 |
| Lungs | 0.25 ± 0.05 | 0.12 |
| Liver | 0.61 ± 0.23 | 0.17 |
| Spleen | 0.20 ± 0.07 | 0.10 |
| Stomach | 0.08 ± 0.01 | 0.03 |
| Small Intestine | 0.14 ± 0.01 | 0.11 |
| Large Intestine | 0.20 ± 0.05* | 0.18 |
| Kidneys | 0.41 ± 0.03 | 0.25 |
| Muscle | 0.08 ± 0.06 | 0.18 |
| Bone | 0.03 ± 0.03** | 0.54 |
| *Tumor (g)* | *0.360 ± 0.09* | *0.379* |
| *Tumor-to-tissue ratios* | | |
| Blood | 15.8 ± 1.7 | 26.7 |
| Heart | 22.2 ± 3.3 | 31.5 |
| Lungs | 14.1 ± 1.7 | 15.1 |
| Liver | 5.8 ± 2.2 | 11.1 |
| Spleen | 17.2 ± 6.4 | 17.9 |
| Stomach | 45.6 ± 9.8 | 55.8 |
| Small Intestine | 25.5 ± 2.5 | 16.7 |
| Large Intestine | 17.5 ± 2.9 | 10.0 |
| Kidneys | 8.6 ± 0.7 | 7.35 |
| Muscle | 45.3 ± 16.4 | 10.4 |
| Bone | 131.2 ± 84.6 | 3.40 |

*with 1.92 %ID/g outlier not excluded 0.63 ± 0.86
** with 0.18 %ID/g outlier not excluded 0.06 ± 0.08

FIG. 12A

| Tissues | [$^{177}$Lu]Lu-aminobenzylDOTA, 10 μCi, 2 pmol (*n* = 5) | [$^{177}$Lu]Lu-aminobenzylDOTA, 1000 μCi, 200 pmol (*n* = 5) | [$^{177}$Lu]Lu-GeminiDOTA, 10 μCi, 80 pmol (*n* = 6) | [$^{177}$Lu]Lu-GeminiDOTA, 200 μCi, 1.6 nmol (*n* = 4) |
|---|---|---|---|---|
| Blood | 2.20 ± 1.00 | 0.11 ± 0.05 | 1.95 ± 0.61 | 0.14 ± 0.02 |
| Heart | 0.97 ± 0.29 | 0.05 ± 0.01 | 0.89 ± 0.25 | 0.06 ± 0.01 |
| Lungs | 1.32 ± 0.51 | 0.09 ± 0.03 | 0.90 ± 0.31 | 0.09 ± 0.02 |
| Liver | 1.28 ± 0.52 | 0.08 ± 0.02 | 0.90 ± 0.26 | 0.09 ± 0.02 |
| Spleen | 0.83 ± 0.24 | 0.05 ± 0.01 | 0.57 ± 0.26 | 0.05 ± 0.01 |
| Stomach | 0.25 ± 0.05 | 0.03 ± 0.01 | 0.20 ± 0.06 | 0.02 ± 0.00 |
| Small Int. | 0.33 ± 0.08 | 0.03 ± 0.01 | 0.25 ± 0.07 | 0.03 ± 0.00 |
| Large Int. | 0.47 ± 0.09 | 0.07 ± 0.01 | 0.24 ± 0.09 | 0.04 ± 0.01 |
| Kidneys | 1.30 ± 0.42 | 0.45 ± 0.05 | 1.17 ± 0.19 | 0.48 ± 0.05 |
| Muscle | 0.95 ± 0.36 | 0.02 ± 0.00 | 0.26 ± 0.06 | 0.03 ± 0.01 |
| Bone | 2.37 ± 1.17 | 0.07 ± 0.04 | 1.04 ± 0.34 | 0.04 ± 0.01 |
| *Tumor* | *17.66 ± 2.06* | *3.76 ± 0.32* | *15.00 ± 4.53* | *5.07 ± 0.38* |
| *Tumor size (g)* | *0.06 ± 0.01* | *0.10 ± 0.02* | *0.06 ± 0.01* | *0.10 ± 0.02* |
| *Tumor-to-tissue ratios* | | | | |
| Blood | 8.0 ± 3.7 | 33.0 ± 14.0 | 7.7 ± 3.3 | 36.2 ± 5.8 |
| Heart | 18.1 ± 5.8 | 75.3 ± 20.1 | 17.0 ± 7.0 | 88.2 ± 13.3 |
| Lungs | 13.4 ± 5.4 | 40.9 ± 12.5 | 16.7 ± 7.6 | 56.3 ± 13.9 |
| Liver | 13.8 ± 5.8 | 44.8 ± 10.1 | 16.8 ± 7.1 | 57.9 ± 13.2 |
| Spleen | 21.2 ± 6.5 | 75.3 ± 19.6 | 26.6 ± 14.8 | 101.4 ± 26.0 |
| Stomach | 70.6 ± 16.4 | 110.7 ± 30.0 | 76.9 ± 32.6 | 289.7 ± 46.8 |
| Small Int. | 52.9 ± 14.4 | 134.4 ± 21.4 | 61.2 ± 26.2 | 184.4 ± 35.0 |
| Large Int. | 37.9 ± 8.7 | 52.3 ± 9.3 | 62.1 ± 29.2 | 135.2 ± 38.5 |
| Kidneys | 13.6 ± 4.7 | 8.3 ± 1.1 | 12.9 ± 4.4 | 10.6 ± 1.3 |
| Muscle | 18.7 ± 7.5 | 171.1 ± 32.6 | 57.0 ± 21.1 | 156.0 ± 32.4 |
| Bone | 7.5 ± 3.8 | 55.4 ± 33.3 | 14.5 ± 6.4 | 144.9 ± 28.9 |

FIG. 12B

| Tissues | [$^{177}$Lu]Lu-aminobenzylDOTA, 1000 μCi, 200 pmol (*n* = 5) | [$^{177}$Lu]Lu-GeminiDOTA, 200 μCi, 1.6 nmol (*n* = 4) | *P* *Student's t-test* |
|---|---|---|---|
| Blood | 0.11 ± 0.05 | 0.14 ± 0.02 | 0.330 |
| Heart | 0.05 ± 0.01 | 0.06 ± 0.01 | 0.325 |
| Lungs | 0.09 ± 0.03 | 0.09 ± 0.02 | 0.478 |
| Liver | 0.08 ± 0.02 | 0.09 ± 0.02 | 0.448 |
| Spleen | 0.05 ± 0.01 | 0.05 ± 0.01 | 0.500 |
| Stomach | 0.03 ± 0.01 | 0.02 ± 0.00 | 0.074 |
| Small Int. | 0.03 ± 0.01 | 0.03 ± 0.00 | 0.468 |
| Large Int. | 0.07 ± 0.01 | 0.04 ± 0.01 | 0.031 |
| Kidneys | 0.45 ± 0.05 | 0.48 ± 0.05 | 0.354 |
| Muscle | 0.02 ± 0.00 | 0.03 ± 0.01 | 0.088 |
| Bone | 0.07 ± 0.04 | 0.04 ± 0.01 | 0.250 |
| *Tumor* | *3.76 ± 0.32* | *5.07 ± 0.38* | 0.017 |
| *Tumor size (g)* | *0.10 ± 0.02* | *0.10 ± 0.02* | |
| *Tumor-to-tissue ratios* | | | |
| Blood | 33.0 ± 14.0 | 36.2 ± 5.8 | |
| Heart | 75.3 ± 20.1 | 88.2 ± 13.3 | |
| Lungs | 40.9 ± 12.5 | 56.3 ± 13.9 | |
| Liver | 44.8 ± 10.1 | 57.9 ± 13.2 | |
| Spleen | 75.3 ± 19.6 | 101.4 ± 26.0 | |
| Stomach | 110.7 ± 30.0 | 289.7 ± 46.8 | |
| Small Int. | 134.4 ± 21.4 | 184.4 ± 35.0 | |
| Large Int. | 52.3 ± 9.3 | 135.2 ± 38.5 | |
| Kidneys | 8.3 ± 1.1 | 10.6 ± 1.3 | |
| Muscle | 171.1 ± 32.6 | 156.0 ± 32.4 | |
| Bone | 55.4 ± 33.3 | 144.9 ± 28.9 | |

FIG. 13

| Tissues | [$^{203}$Pb]TCMC-proteus-DOTA, 1.11 MBq (30 μCi), 280 pmol (*n* = 4) | [$^{203}$Pb]Proteus-DOTA, 1.11 MBq (30 μCi), 280 pmol (*n* = 4) | *P* *Student's t-test* |
|---|---|---|---|
| Blood | 0.31 ± 0.12 | 0.28 ± 0.10 | 0.342 |
| Heart | 0.14 ± 0.04 | 0.12 ± 0.03 | 0.210 |
| Lungs | 0.36 ± 0.11 | 0.27 ± 0.08 | 0.108 |
| Liver | 0.65 ± 0.04 | 0.25 ± 0.04 | $<0.0001$ |
| Spleen | 0.23 ± 0.04 | 0.12 ± 0.03 | 0.003 |
| Stomach | 0.05 ± 0.01 | 0.03 ± 0.01 | 0.107 |
| Small Int. | 0.08 ± 0.02 | 0.07 ± 0.01 | 0.036 |
| Large Int. | 0.11 ± 0.02 | 0.15 ± 0.05 | 0.092 |
| Kidneys | 1.49 ± 0.07 | 1.02 ± 0.18 | 0.001 |
| Muscle | 0.09 ± 0.02 | 0.04 ± 0.01 | 0.001 |
| Bone | 0.09 ± 0.03 | 0.11 ± 0.02 | 0.144 |
| *Tumor* | *27.79 ± 7.38* | *25.66 ± 10.47* | 0.376 |
| *Tumor size (g)* | *0.022 ± 0.012* | *0.015 ± 0.016* | |
| *Tumor-to-tissue ratios* | | | |
| Blood | 89.6 ± 20.6 | 92.5 ± 25.0 | |
| Heart | 198.5 ± 36.5 | 213.9 ± 50.9 | |
| Lungs | 77.7 ± 15.8 | 96.8 ± 24.1 | |
| Liver | 42.9 ± 5.8 | 101.6 ± 22.3 | |
| Spleen | 122.1 ± 20.1 | 223.2 ± 55.7 | |
| Stomach | 617.4 ± 120.7 | 789.6 ± 222.0 | |
| Small Int. | 336.8 ± 54.2 | 394.8 ± 82.4 | |
| Large Int. | 264.6 ± 46.2 | 174.0 ± 46.6 | |
| Kidneys | 18.6 ± 2.5 | 25.3 ± 5.6 | |
| Muscle | 308.7 ± 49.7 | 733.2 ± 182.6 | |
| Bone | 308.7 ± 68.0 | 228.1 ± 51.7 | |

FIG. 14

| Tissues | [111In]proteus-DOTA(Lu), 1.85 MBq (50 μCi), 200 pmol (*n* = 4) | [111In]proteus-DOTA(Gd), 1.85 MBq (50 μCi), 200 pmol (*n* = 4) | *P* *Student's t-test* |
|---|---|---|---|
| Blood | 0.63 ± 0.31 | 0.46 ± 0.21 | 0.198 |
| Heart | 0.23 ± 0.10 | 0.17 ± 0.07 | 0.201 |
| Lungs | 0.34 ± 0.16 | 0.28 ± 0.11 | 0.286 |
| Liver | 0.30 ± 0.12 | 0.24 ± 0.08 | 0.223 |
| Spleen | 0.20 ± 0.07 | 0.15 ± 0.05 | 0.143 |
| Stomach | 0.05 ± 0.02 | 0.05 ± 0.02 | 0.456 |
| Small Int. | 0.08 ± 0.05 | 0.06 ± 0.02 | 0.249 |
| Large Int. | 0.10 ± 0.05 | 0.12 ± 0.04 | 0.247 |
| Kidneys | 0.67 ± 0.13 | 0.58 ± 0.11 | 0.163 |
| Muscle | 0.06 ± 0.02 | 0.06 ± 0.02 | 0.492 |
| Bone | 0.12 ± 0.07 | 0.08 ± 0.04 | 0.184 |
| *Tumor* | *9.25 ± 2.72* | *7.66 ± 4.74* | 0.291 |
| *Tumor size (g)* | *0.111 ± 0.012* | *0.140 ± 0.041* | |
| *Tumor-to-tissue ratios* | | | |
| Blood | 14.6 ± 4.2 | 16.6 ± 6.3 | |
| Heart | 40.3 ± 10.5 | 43.9 ± 16.3 | |
| Lungs | 27.3 ± 7.6 | 27.3 ± 10.1 | |
| Liver | 31.1 ± 8.0 | 32.4 ± 11.5 | |
| Spleen | 45.6 ± 10.7 | 51.2 ± 18.3 | |
| Stomach | 177.3 ± 44.6 | 142.0 ± 52.3 | |
| Small Int. | 114.2 ± 37.2 | 123.3 ± 44.6 | |
| Large Int. | 96.8 ± 27.3 | 64.6 ± 23.3 | |
| Kidneys | 13.9 ± 2.5 | 13.3 ± 4.3 | |
| Muscle | 154.3 ± 38.9 | 127.1 ± 43.7 | |
| Bone | 76.8 ± 25.8 | 96.9 ± 40.6 | |

DOTA-HAPTEN COMPOSITIONS FOR ANTI-DOTA/ANTI-TUMOR ANTIGEN BISPECIFIC ANTIBODY PRETARGETED RADIOIMMUNOTHERAPY

CROSS-REFERENCE TO RELATED APPLICATIONS

This application is a U.S. National Stage Application of PCT/US2021/039423, filed Jun. 28, 2021, which claims the benefit of and priority to U.S. Provisional Patent Application No. 63/045,632, filed Jun. 29, 2020, the contents of which are incorporated by reference herein in its entirety.

STATEMENT OF GOVERNMENT SUPPORT

This invention was made with government support under CA008748 and CA184746 awarded by the National Institutes of Health. The government has certain rights in the invention.

TECHNICAL FIELD

The present technology relates generally to compositions including novel DOTA-haptens and methods of using the same in diagnostic imaging as well as pretargeted radioimmunotherapy.

BACKGROUND

The following description of the background of the present technology is provided simply as an aid in understanding the present technology and is not admitted to describe or constitute prior art to the present technology.

Radiolabeled agents have been used as delivery vehicles of ionizing radiation to specific disease sites for over 50 years (Larson S M. *Cancer* 67:1253-1260 (1991); Britton K E. *Nucl Med Commun.* 18:992-1007 (1997)). A large number of molecules have been considered for targeted delivery of radioisotopes, including radiolabeled antibodies, antibody fragments, alterative scaffolds, and small molecules (Tolmachev V, et al. *Cancer Res.* 67:2773-2782 (2007); Birchler M T, et al., *Otolaryngol Head Neck Surg.* 136:543-548 (2007); Reubi J C, Maecke H R. *J Nucl Med.* 49:1735-1738 (2008)). Using antibodies to target poisons to tumors, e.g., radioimmunotherapy (RIT) with directly conjugated antibodies, has been challenging due in part to suboptimal tumor dose and therapeutic index (TI). Further, because of normal tissue bystander toxicity, dose escalation is not feasible and therefore such therapy results in limited anti-tumor effect. Moreover, antibodies exhibit long half-lives in the blood resulting in low tumor-to-background ratios. Antibody fragments and other smaller binding scaffolds exhibit faster blood clearance, but result in high kidney and/or liver uptake. Radiolabeled small molecule ligands generally exhibit more rapid blood clearance and lower background compared to antibodies and antibody fragments, but usually result in poor specificity due to relatively low affinities for the desired target.

In pretargeted radioimmunotherapy (PRIT), a nonradioactive bifunctional antibody with specificity for both a tumor antigen and a small molecule hapten is administered and allowed to localize to the tumor(s). After sufficient blood clearance of the antibody, a radiolabeled small molecule is administered and is captured by the pretargeted antibody. However, many small peptide and metal chelate haptens used in PRIT systems exhibit significant whole-body retention, which results in unwanted background activity that limits signal-to-background ratios for imaging and contributes to nonspecific radiation that limits the maximum tolerated dose for therapy applications (Orcutt et al., *Mol Imaging Biol* 13:215-221 (2011)).

Thus, there is a need for novel molecules that permit (a) efficient pretargeted radioimmunotherapy of tumors in vivo and (b) rapid clearance of radiolabeled small molecules from non-tumor tissue.

SUMMARY OF THE PRESENT TECHNOLOGY

In one aspect, the present disclosure provides a compound of Formula I (I)

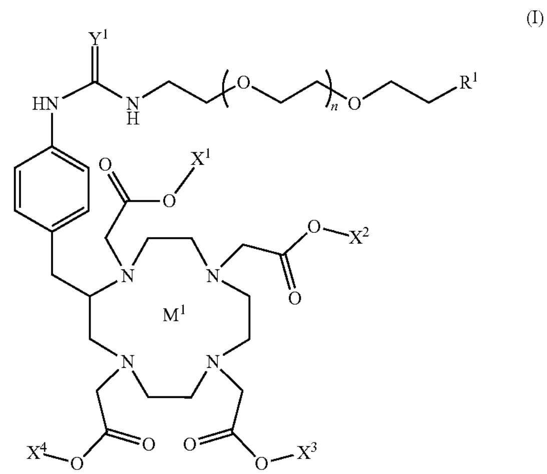

or a pharmaceutically acceptable salt thereof, wherein $M^1$ is a chelated $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$ or $^{160}Gd^{3+}$.

$R^1$ is
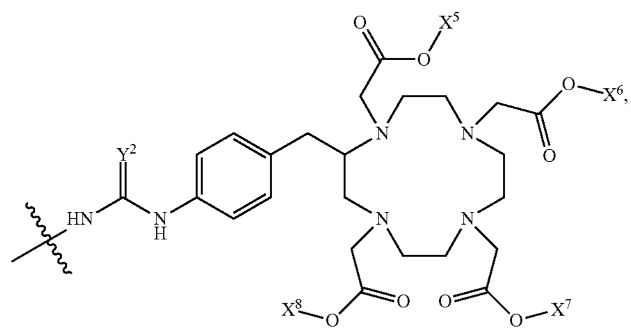
,
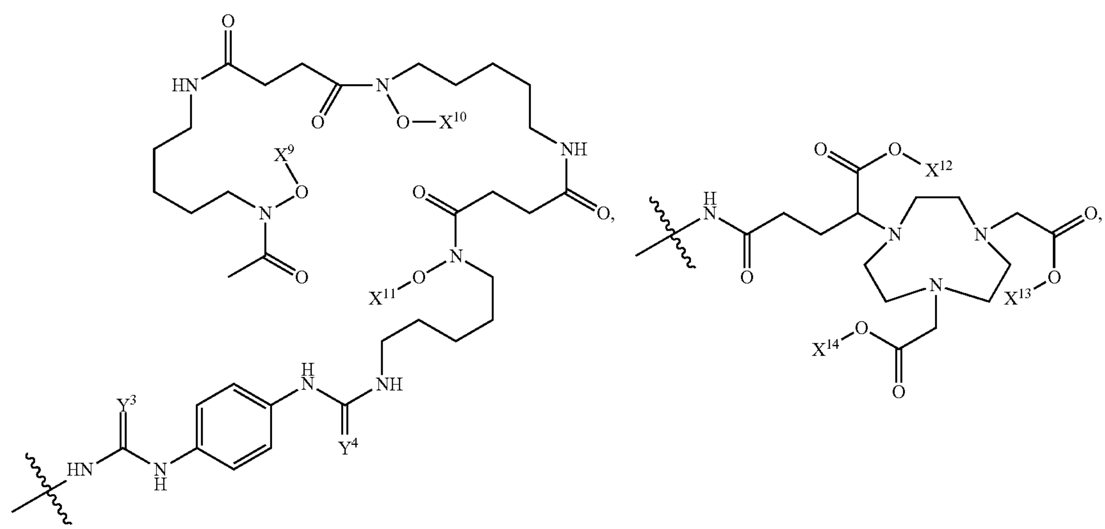
,
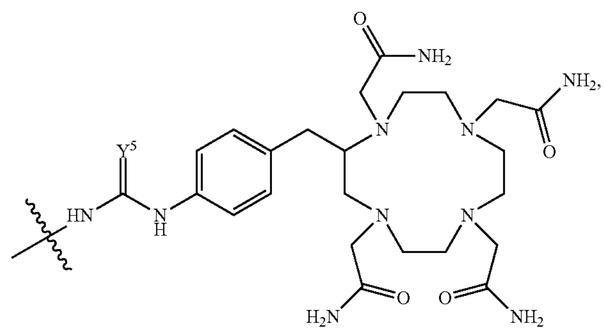
,
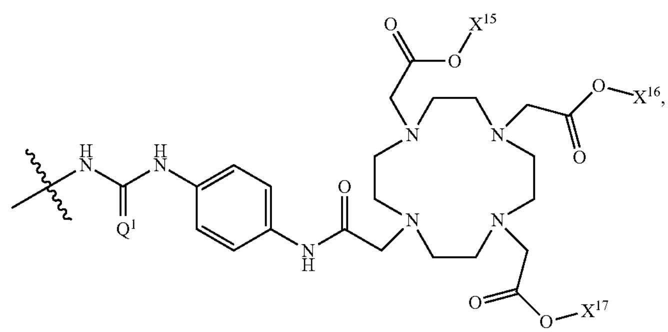
,

-continued
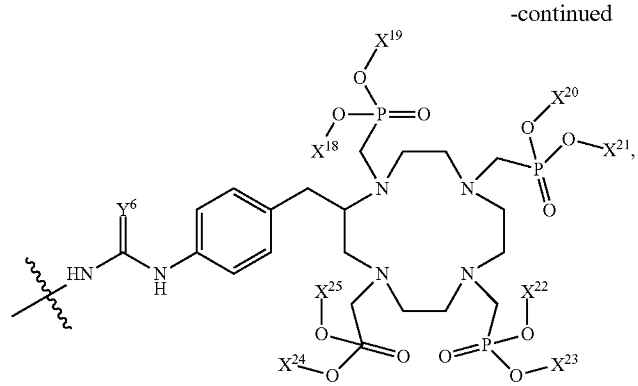
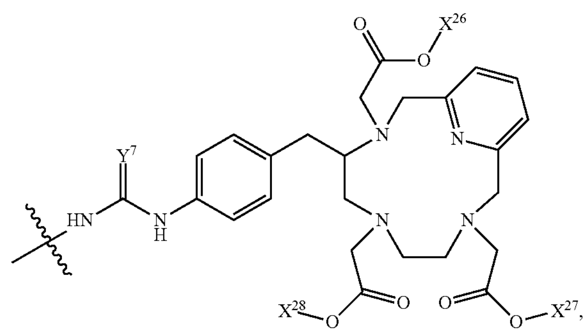
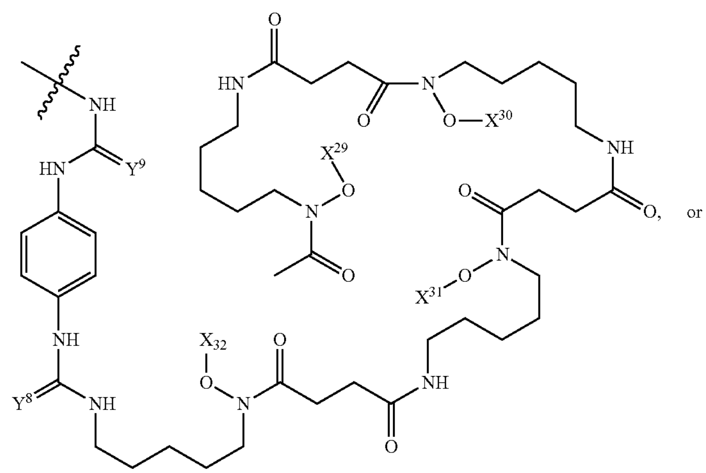
or

-continued

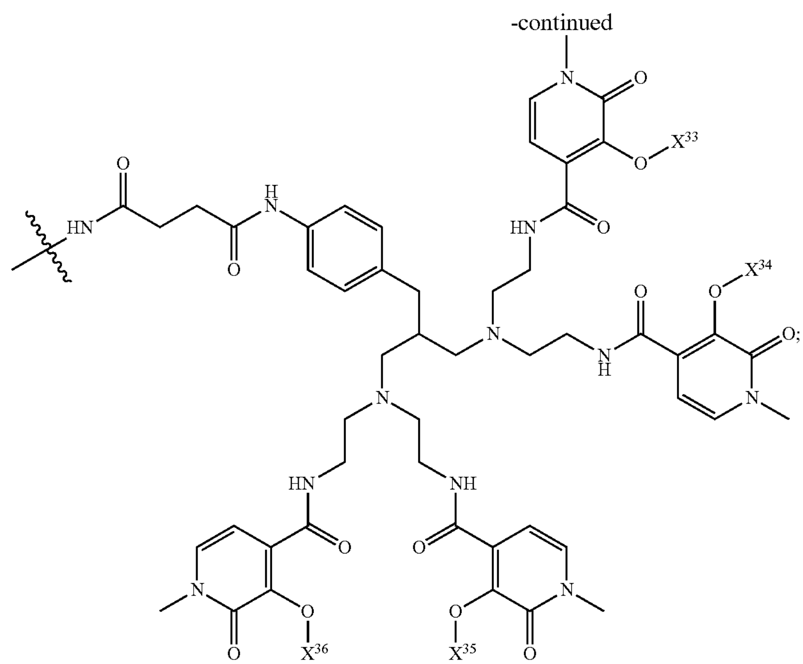

$X^1$, $X^2$, $X^3$, $X^4$, $X^5$, $X^6$, $X^7$, $x^8$, $X^9$, $X^{10}$, $X^{11}$, $x^{12}$, $X^{13}$, $X^{14}$, $X^{15}$, $X^{16}$, $X^{17}$, $x^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, $X^{35}$, and $X^{36}$ are each independently a lone pair of electrons (i.e., providing an oxygen anion) or H; $Y^1$, $Y^2$, $Y^3$, $Y^4$, $Y^5$, $Y^6$, $Y^7$, $Y^8$, and $Y^9$ are each independently S or O; $Q^1$ is S or O; and n is 1, 2, 3, 4, 5, 6, 7, 8, 9, 10, 11, 12, 13, 14, 15, 16, 17, 18, 19, 20, 21, or 22. In certain embodiments, n is 3.

In another aspect, the present disclosure provides a bis-chelate comprising any of the above compounds of Formula I and a radionuclide cation. In some embodiments, the bischelate is of Formula II (II)

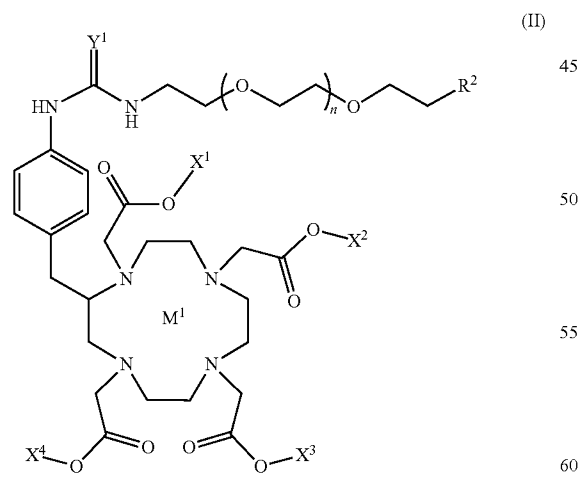

or a pharmaceutically acceptable salt thereof, wherein $M^1$ is a chelated $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $^{60}Gd^{3+}$.

$R^2$ is
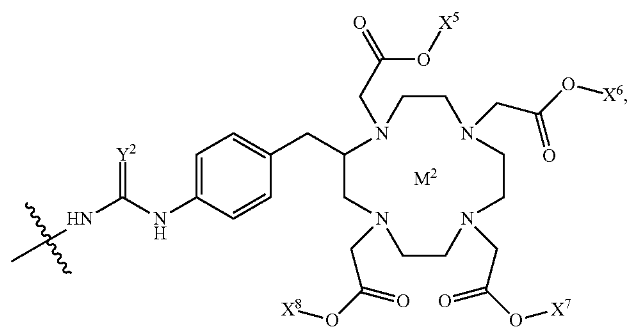
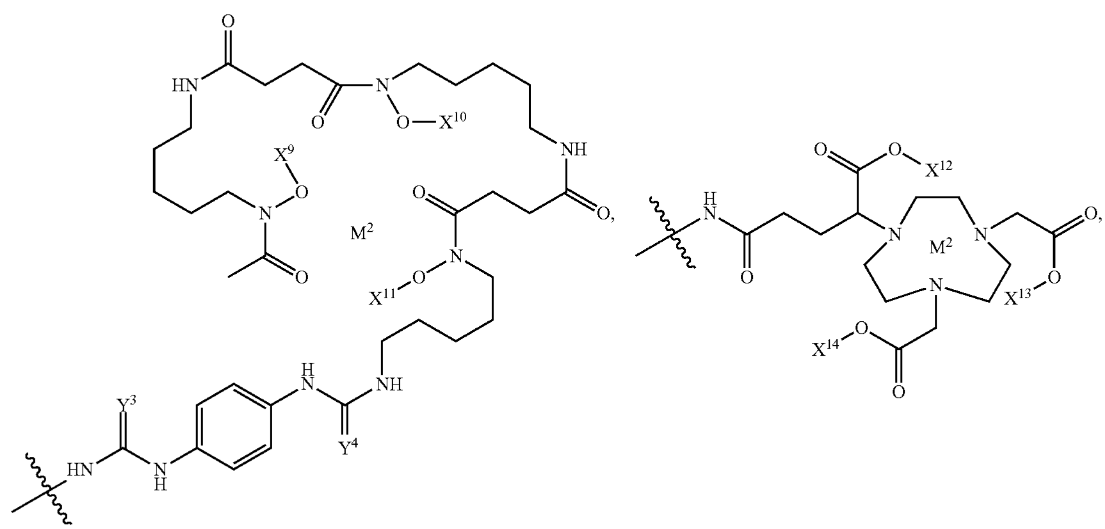
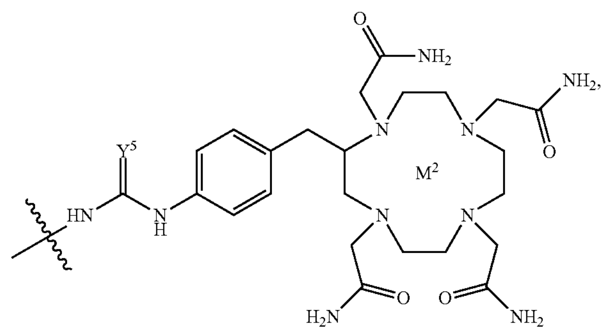
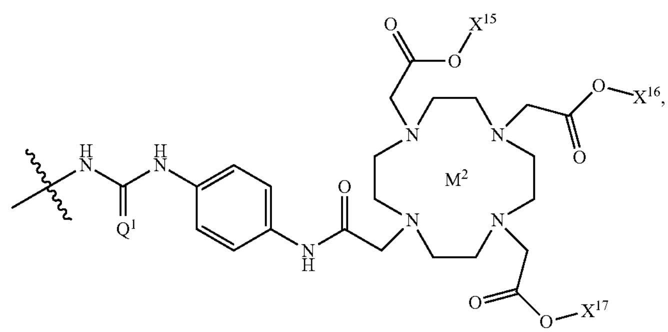

-continued
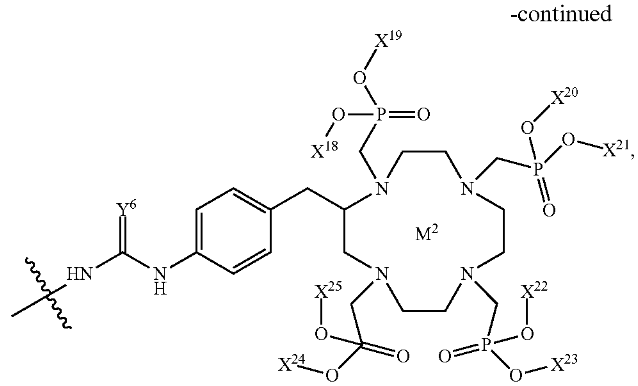
,
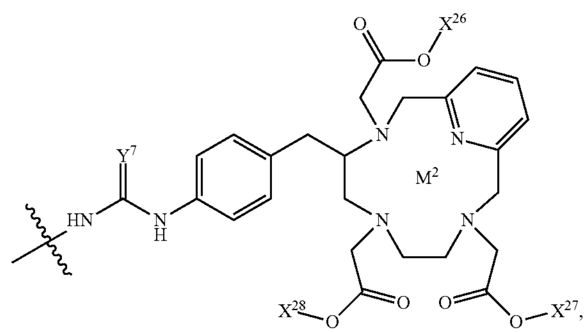
,
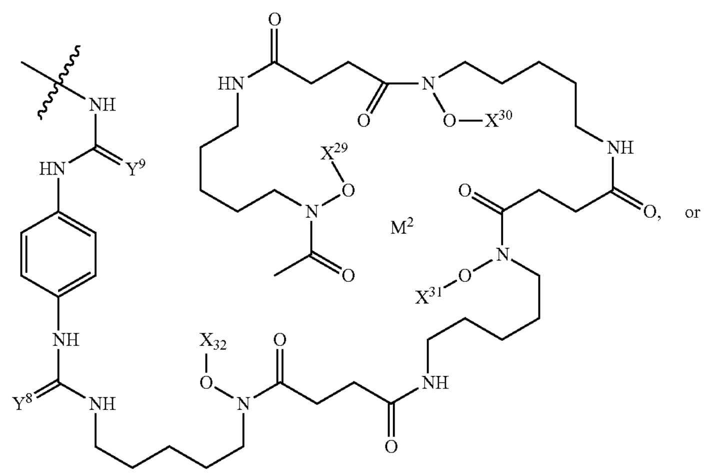
, or

-continued

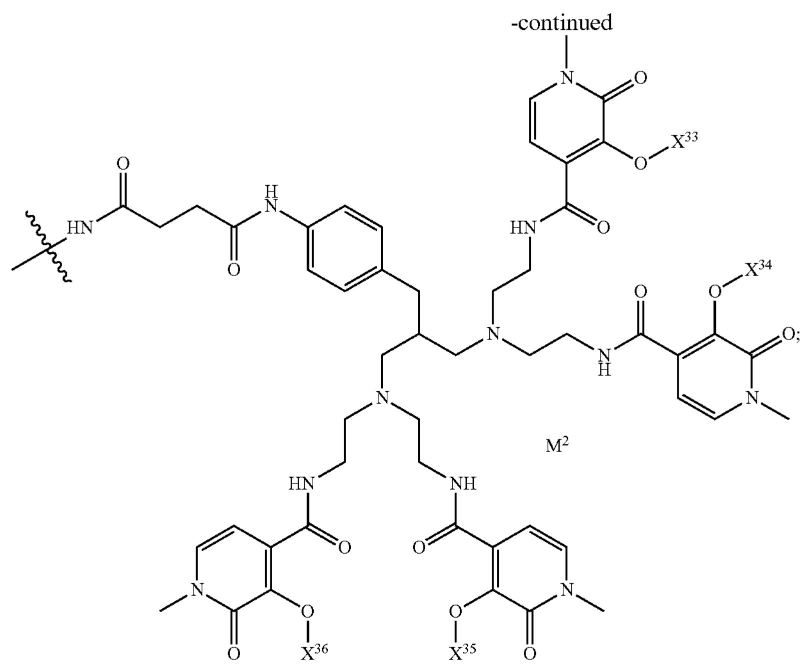

$M^2$ is independently at each occurrence a radionuclide cation chelated by the $R^2$ group; $X^1$, $X^2$, $X^3$, $X^4$, $X^5$, $X^6$, $X^7$, $x^8$, $X^9$, $X^{10}$, $x^{11}$, $X^{12}$, $X^{13}$, $X^{14}$, $x^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, $X^{35}$, and $X^{36}$ are each independently a lone pair of electrons (i.e., providing an oxygen anion) or H; $Y^1$, $Y^2$, $Y^3$, $Y^4$, $Y^5$, $Y^6$, $Y^7$, $Y^8$, and $Y^9$ are each independently S or O; $Q^1$ is S or O; and n is 1, 2, 3, 4, 5, 6, 7, 8, 9, 10, 11, 12, 13, 14, 15, 16, 17, 18, 19, 20, 21, or 22. In certain embodiments, n is 3. Additionally or alternatively, in some embodiments, the radionuclide cation is a divalent cation or a trivalent cation.

In any and all embodiments, the compound of Formula II includes a radionuclide cation that is chelated by the $R^2$ group. The radionuclide cation may be an alpha particle-emitting isotope, a beta particle-emitting isotope, an Auger-emitter, or a combination of any two or more thereof. Examples of alpha particle-emitting isotopes include, but are not limited to, $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Examples of beta particle-emitting isotopes include, but are not limited to, $^{86}$Y, $^{90}$Y, $^{89}$Sr, $^{165}$Dy, $^{186}$Re, $^{188}$Re, $^{177}$Lu, and $^{67}$Cu. Examples of Auger-emitters include $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, and $^{203}$Pb. In some embodiments of the compounds of Formula II, the radionuclide cation is $^{89}$Zr, $^{68}$Ga, $^{203}$Pb, $^{212}$Pb, $^{227}$Th, or $^{64}$Cu.

In some embodiments, the radionuclide cation has a decay energy in the range of 20 to 6,000 keV. Decay energies can be within the range of 60 to 200 keV for an Auger emitter, 100-2,500 keV for a beta emitter, and 4,000-6,000 keV for an alpha emitter. Maximum decay energies of useful beta-particle-emitting nuclides can range from 20-5,000 keV, 100-4,000 keV, or 500-2,500 keV. Decay energies of useful Auger-emitters can be $<$1,000 keV, $<$100 keV, or $<$70 keV. Decay energies of useful alpha-particle-emitting radionuclides can range from 2,000-10,000 keV, 3,000-8,000 keV, or 4,000-7,000 keV.

In another aspect, the present disclosure provides a complex comprising the compound of Formula I and a bispecific antibody that recognizes and binds to the compound and a tumor antigen target. The present disclosure also provides a complex comprising the bischelate of Formula II and a bispecific antibody that binds to the bischelate and a tumor antigen target. In any of the above embodiments of the complexes disclosed herein, the bispecific antibody may be an infinite binder. In some embodiments, the bispecific antibody comprises an antigen binding fragment of C825 (See Cheal et al., *Mol Cancer Ther.* 13(7):1803-12 (2014)) or 2D12.5 (Corneillie et al., *J. Inorganic Biochemistry* 100:882-890 (2006)). Additionally or alternatively, in any of the above embodiments of the complexes disclosed herein, the bispecific antibody comprises an antigen binding fragment of C825 with a G54C substitution. Additionally or alternatively, in any of the above embodiments of the complexes disclosed herein, the bispecific antibody comprises an antigen binding fragment of 2D12.5 with a G54C substitution.

In any of the above embodiments of the complexes disclosed herein, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM. Additionally or alternatively, in some embodiments of the complex, the bispecific antibody binds to the compound or the bischelate with a $K_d$ that is lower than or equal to 100 nM-95 nM, 95-90 nM, 90-85 nM, 85-80 nM, 80-75 nM, 75-70 nM, 70-65 nM, 65-60 nM, 60-55 nM, 55-50 nM, 50-45 nM, 45-40 nM, 40-35 nM, 35-30 nM, 30-25 nM, 25-20 nM, 20-15 nM, 15-10 nM, 10-5 nM, 5-1 nM, 1 nM-950 pM, 950 pM-900 pM, 900 pM-850 pM, 850 pM-800 pM, 800 pM-750 pM, 750 pM-700 pM, 700 pM-650 pM, 650 pM-600 pM, 600 pM-550 pM, 550 pM-500 pM, 500 pM-450 pM, 450 pM-400 pM, 400 pM-350 pM, 350 pM-300 pM, 300 pM-250 pM, 250 pM-200 pM, 200 pM-150 pM, 150 pM-100 pM, 100 pM-50 pM, 50 pM-40 pM, 40 pM-30 pM, 30 pM-20 pM, 20 pM-10 pM, 9 pM, 8 pM, 7 pM, 6 pM, 5 pM, 4 pM, 3 pM, 2.5 pM, 2 pM, 1.5 pM, or 1 pM.

In one aspect, the present disclosure provides a method for detecting tumors in a subject in need thereof comprising (a) administering to the subject an effective amount of a complex comprising the bischelate of Formula II and a bispecific antibody that binds to the bischelate and a tumor antigen target, wherein the complex is configured to localize to a tumor expressing the tumor antigen target recognized by the bispecific antibody of the complex; and (b) detecting the presence of tumors in the subject by detecting radioactive levels emitted by the complex that are higher than a reference value. The tumors may be solid tumors or liquid tumors. In some embodiments, the subject is human.

In another aspect, the present disclosure provides a method for selecting a subject for pretargeted radioimmunotherapy comprising (a) administering to the subject an effective amount of a complex comprising the bischelate of Formula II and a bispecific antibody that binds to the bischelate and a tumor antigen target, wherein the complex is configured to localize to a tumor expressing the tumor antigen target recognized by the bispecific antibody of the complex; (b) detecting radioactive levels emitted by the complex; and (c) selecting the subject for pretargeted radioimmunotherapy when the radioactive levels emitted by the complex are higher than a reference value. In some embodiments, the subject is human.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having cancer. The cancer may be selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, and head-and-neck cancer. In some embodiments, the brain cancer is a pituitary adenoma, a meningioma, a neuroblastoma, or a craniopharyngioma.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally or intranasally. In certain embodiments, the complex is administered into the cerebral spinal fluid or blood of the subject.

In some embodiments of the methods disclosed herein, the radioactive levels emitted by the complex are detected between 4 to 24 hours after the complex is administered. In certain embodiments of the methods disclosed herein, the radioactive levels emitted by the complex are expressed as the percentage injected dose per gram tissue (% ID/g). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with cancer comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of Formula II to the subject, wherein the bischelate is configured to bind to the anti-DOTA bispecific antibody. In some embodiments, the method further comprises administering an effective amount of a clearing agent to the subject prior to administration of the bischelate. The clearing agent may be a 500 kD amino-dextran-DOTA conjugate (e.g., 500 kD dextran-DOTA-Bn (Y), 500 kD dextran-DOTA-Bn (Lu), or 500 kD dextran-DOTA-Bn (In) etc.). In some embodiments, the subject is human.

Additionally or alternatively, in some embodiments of the method, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM.

Additionally or alternatively, in some embodiments of the method, the anti-DOTA bispecific antibody and/or the bischelate is administered intravenously, intramuscularly, intraarterially, intrathecally, intracapsularly, intraorbitally, intradermally, intraperitoneally, transtracheally, subcutaneously, intracerebroventricularly, orally or intranasally.

In one aspect, the present disclosure provides a method for increasing tumor sensitivity to radiation therapy in a subject diagnosed with cancer comprising administering to the subject an effective amount of a complex comprising the bischelate of Formula II and a bispecific antibody that recognizes and binds to the bischelate and a tumor antigen target, wherein the complex is configured to localize to a tumor expressing the tumor antigen target recognized by the bispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments, the subject is human.

In another aspect, the present disclosure provides a method for treating cancer in a subject in need thereof comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of Formula II to the subject, wherein the bischelate is configured to bind to the anti-DOTA bispecific antibody. In certain embodiments, the method further comprises administering an effective amount of a clearing agent to the subject prior to administration of the bischelate. Also provided herein are methods for treating cancer in a subject in need thereof comprising administering to the subject an effective amount of a complex comprising the bischelate of Formula II and a bispecific antibody that recognizes and binds to the bischelate and a tumor antigen target, wherein the complex is configured to localize to a tumor expressing the tumor antigen target recognized by the bispecific antibody of the complex.

The methods for treating cancer may further comprise sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11. In some embodiments, the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, and head-and-neck cancer. In some embodiments, the subject is human.

Also disclosed herein are kits containing components suitable for treating or diagnosing cancer in a patient. In one aspect, the kits comprise a compound or bischelate of the present technology, at least one anti-DOTA bispecific antibody, and instructions for use. The kits may further comprise a clearing agent (e.g., 500 kDa aminodextran conjugated to DOTA) and/or one or more radionuclides.

BRIEF DESCRIPTION OF THE DRAWINGS

FIG. 2 shows ex vivo biodistribution studies of $^{89}$Zr activity in various tissues for pretargeting of [$^{89}$Zr]DFO-PEG$_4$-LuDOTA and non-pretargeted [$^{89}$Zr]DFO-PEG$_4$-LuDOTA in SW1222-tumor bearing mice and tumor-free mice, respectively at 4 hours (h) post-injection (p.i.). Data is presented as average±standard deviation.

FIG. 3 shows whole-blood sampling via retro orbital bleeding of tumor-free mice administered [$^{89}$Zr]DFO-PEG$_4$-LuDOTA. Data is presented as average±standard deviation. % IA/g refers to percent area under an ideal dose-volume histogram curve (IA) per gram.

FIG. 4 shows whole-body $^{89}$Zr activity of tumor-free mice administered [$^{89}$Zr]DFO-PEG$_4$-LuDOTA. Data is presented as average±standard deviation.

FIG. 5 shows representative PET maximum intensity projection images of two different mice that underwent PRIT with [$^{89}$Zr]DFO-PEG$_4$-LuDOTA (200 pmol/1.48 MBq). Images were obtained at 4 hours post-injection of [$^{89}$Zr]DFO-PEG$_4$-LuDOTA. Signal was detected in the s.c. GPA33-expressing SW1222 xenografts (circled regions).

FIG. 6 shows ex vivo biodistribution studies of $^{68}$Ga activity in various tissues for pretargeting of [$^{68}$Ga]NODAGA-PEG$_4$-LuDOTA and [$^{68}$Ga]DO3A-PEG$_4$-LuDOTA (described in WO2019/010299) in SW1222-tumor bearing mice at 1 hour (h) post-injection (p.i.). Data is presented as average±standard deviation. For calculation of mol, doses drawn up were 225 μCi and 145 μCi for [$^{68}$Ga]NODAGA-PEG$_4$-LuDOTA and [$^{68}$Ga]DO3A-PEG$_4$-LuDOTA, respectively. *with 5.02% ID/g outlier not excluded 2.44±2.30.

FIG. 8 shows ex vivo serial biodistribution studies of $^{68}$Ga activity in various tissues for pretargeting of [$^{68}$Ga]NODAGA-PEG$_4$-LuDOTA in SW1222-tumor bearing mice. Data is presented as average±standard deviation. *Without 0.0631 g outlier excluded 0.428±0.299 g; **Without 0.0631 g outlier excluded 6.68±3.49% IA/g.

FIG. 10 shows ex vivo biodistribution studies of $^{64}$Cu activity in various tissues for pretargeting of [$^{64}$Cu]NODAGA-PEG$_4$-LuDOTA in SW1222-tumor bearing mice at 24 h post-injection. Data is presented as average±standard deviation. *with 1.92% ID/g outlier not excluded 0.63±0.86; ** with 0.18% ID/g outlier not excluded 0.06±0.08.

FIGS. 12A-12B show ex vivo biodistribution studies of $^{177}$Lu activity in various tissues for pretargeting of [$^{177}$Lu]DOTABn-PEG$_4$-LuDOTA (also referred to as "[$^{177}$Lu]Lu-GeminiDOTA") in SW1222-tumor bearing mice at 24 h post-injection. Data is presented as % injected activity per gram of tissue (% IA/g), (average±SEM).

FIG. 13 shows ex vivo biodistribution studies of $^{203}$Pb activity in various tissues for pretargeting of $^{203}$Pb]TCMC-PEG$_4$-LuDOTA (also referred to herein as "[$^{203}$Pb]TCMC-proteus-DOTA") or [$^{203}$Pb]DO3A-PEG$_4$-LuDOTA (also referred to herein as "[$^{203}$Pb]Proteus-DOTA") in SW1222- tumor bearing mice at 24 h post-injection. Data is presented as % injected activity per gram of tissue (% IA/g), (average±SD).

Figure 1A:
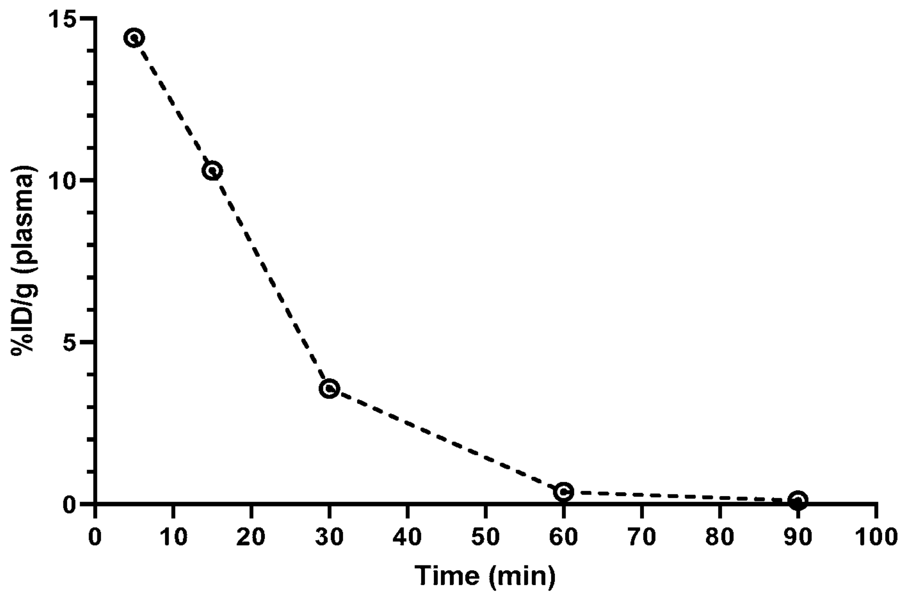
FIG. 1A shows a plot of percent injected dose per gram (% ID/g) versus time for mice injected with a compound of the present technology including a chelated radionuclide ([$^{203}$Pb]TCMC-PEG$_4$-LuDOTA). These results demonstrate that the vast majority (>97%) of [$^{203}$Pb]TCMC-PEG$_4$-LuDOTA is cleared from the plasma after 1 hour.

FIG. 14 shows ex vivo biodistribution studies of $^{111}$In activity in various tissues for pretargeting of [$^{111}$In]proteus-DOTA(Lu) or [$^{111}$In]proteus-DOTA(Gd) in SW1222-tumor bearing mice at 24 h post-injection. Data is presented as % injected activity per gram of tissue (% IA/g), (average±SD).

DETAILED DESCRIPTION

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

The compositions of the present technology include novel DOTA-haptens that are useful in diagnostic imaging/dosimetry and PRIT (e.g., alpha-particle radioimmunotherapy). The DOTA-PRIT platform entails a three-step pretargeting strategy including the administration of (1) an IgG-single chain variable fragment (scFv) bispecific antibody construct (IgG-scFv) comprising antibody sequences for an anti-tumor antigen antibody (the IgG-portion) and a pM-affinity anti-DOTA-hapten single chain variable fragment scFv "C825", (2) a 500 kD-dextran-DOTA-hapten clearing agent, and (3) a radiolabeled DOTA hapten composition of the present technology.

Previous studies have demonstrated that anti-GPA33-DOTA-PRIT could be used to pretarget $^{177}$Lu- or $^{86}$Y-S-2-(4-aminobenzyl)-1,4,7,10-tetraazacyclododecane tetraacetic acid chelate (DOTA-Bn) hapten for theranostic beta-particle radioimmunotherapy (RIT) or in vivo positron emission tomography (PET) of athymic nude mice bearing GPA33-expressing colon cancer xenografts, respectively. However, pretargeting with $^{225}$Ac-DOTA-Bn in vivo using a model PRIT system led to unremarkable tumor uptake of $^{225}$Ac-DOTA-Bn 24 hours post-injection (<1% ID/g). See WO2019/010299. Thus, conventional DOTA-haptens are ill-suited for DOTA-PRIT radiotherapy applications involving high linear energy transfer (LET) alpha particle-emitting isotopes such as $^{225}$Ac.

In contrast, the compositions disclosed herein (a) permit efficient in vivo pretargeted radiotherapy of tumors, (b) exhibit complete renal clearance with no unwanted kidney/whole-body retention, and (c) can bind to an anti-DOTA bispecific antibody (e.g., anti-huA33-C825) with high affinity (i.e., the DOTA hapten composition of the present technology does not sterically block the interactions between the lutetium-DOTA moiety of the DOTA hapten composition and an anti-DOTA bispecific antibody).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

The phrase "and/or" as used in the present disclosure will be understood to mean any one of the recited members individually or a combination of any two or more thereof—for example, "A, B, and/or C" would mean "A, B, C, A and B, A and C, or B and C."

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

As used herein, the "administration" of an agent or drug to a subject includes any route of introducing or delivering to a subject a compound to perform its intended function.

Administration can be carried out by any suitable route, including orally, intranasally, parenterally (intravenously, intramuscularly, intraperitoneally, or subcutaneously), rectally, or topically. Administration includes self-administration and the administration by another.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes "intact immunoglobulins") and "antigen binding fragments" specifically bind to a molecule of interest (or a group of highly similar molecules of interest) to the substantial exclusion of binding to other molecules (for example, antibodies and antibody fragments that have a binding constant for the molecule of interest that is about $10^3$ $M^{-1}$ times greater, about $10^4$ $M^{-1}$ times greater or about $10^5$ $M^{-1}$ times greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology,* 3$^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the j-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds a target protein or molecule (e.g., DOTA) will have a specific $V_H$ region and $V_L$ region sequence, and thus specific CDR sequences. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). Examples of antibodies include monoclonal antibodies, polyclonal antibodies, humanized antibodies, chimeric antibodies, recombinant antibodies, multispecific antibodies, bispecific antibodies, and antibody fragments. An antibody specifically binds to an antigen.

A "bispecific antibody" is an antibody that can bind simultaneously to two different antigens. Bispecific antibodies (BsAb) and bispecific antibody fragments (BsFab) may have at least one arm that specifically binds to, for example, a tumor-associated antigen and at least one other arm that specifically binds to a targetable conjugate that bears a therapeutic or diagnostic agent (e.g., a bischelate of the present technology). A variety of different bi-specific antibody structures are known in the art. In some embodiments, each binding moiety in a bispecific antibody comprises a $V_H$ and/or $V_L$ region from different monoclonal antibodies. In some embodiments, the bispecific antibody comprises an immunoglobulin molecule having $V_H$ and/or $V_L$ regions that contain CDRs from a first monoclonal antibody, and an antibody fragment (e.g., Fab, F(ab'), $F(ab')_2$, Fd, Fv, dAB, scFv, etc.) having $V_H$ and/or $V_L$ regions that contain CDRs from a second monoclonal antibody.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404, 097; WO 93/11161; and 30 Hollinger et al., *Proc. Natl. Acad. Sci. USA,* 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ (scFv)). Bird et al. (1988) Science 242:423-426 and Huston et al. (1988) *Proc. Natl. Acad Sci. USA* 85:5879-5883. Such single-chain antibodies can be prepared by recombinant techniques or enzymatic or chemical cleavage of intact antibodies.

As used herein, the terms "intact antibody" or "intact immunoglobulin" mean an antibody or immunoglobulin that has at least two heavy (H) chain polypeptides and two light (L) chain polypeptides interconnected by disulfide bonds.

Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, an "antigen" refers to a molecule to which an antibody can selectively bind. The target antigen may be a protein (e.g., an antigenic peptide), carbohydrate, nucleic acid, lipid, hapten, or other naturally occurring or synthetic compound. An antigen may also be administered to an animal subject to generate an immune response in the subject.

As used herein, the term "antigen binding fragment" refers to a fragment of a whole immunoglobulin structure which possesses a part of a polypeptide responsible for binding to an antigen. Examples of the antigen binding fragment useful in the present technology include scFv, $(scFv)_2$, scFvFc, Fab, Fab' and $F(ab')_2$, diabodies; linear antibodies; single-chain antibody molecules; and multispecific antibodies formed from antibody fragments.

By "binding affinity" is meant the strength of the total noncovalent interactions between a single binding site of a molecule (e.g., an antibody) and its binding partner (e.g., an antigen). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, a "clearing agent" is an agent that binds to excess bifunctional antibody that is present in the blood compartment of a subject to facilitate rapid clearance via kidneys. The use of the clearing agent prior to hapten administration facilitates better tumor-to-background ratios in PRIT systems. Examples of clearing agents include 500 kD-dextran-DOTA-Bn(Y) (Orcutt et al., *Mol Cancer Ther.* 11(6): 1365-1372 (2012)), 500 kD aminodextran-DOTA conjugate, antibodies against the pretargeting antibody, etc.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" of a composition, is a quantity sufficient to achieve a desired prophylactic or therapeutic effect, e.g., an amount which results in the decrease in the symptoms associated with a disease that is being treated, e.g., the diseases or medical conditions associated with target polypeptide (e.g., breast cancer, colorectal cancer, brain cancer etc.). The amount of a composition of the present technology administered to the subject will depend on the degree, type and severity of the disease and on the characteristics of the individual, such as general health, age, sex, body weight and tolerance to drugs. The skilled artisan will be able to determine appropriate dosages depending on these and other factors. The compositions of the present technology can also be administered in combination with one or more additional therapeutic compounds.

As used herein, the term "epitope" means an antigenic determinant capable of specific binding to an antibody. Epitopes usually consist of chemically active surface groupings of molecules and usually have specific three dimensional structural characteristics, as well as specific charge characteristics.

As used herein, an "infinite binder" refers to an anti-metal chelate bispecific antibody that is characterized by the formation of a highly specific permanent bond between the bispecific antibody and the metal chelate upon binding. See Corneillie et al., *J. Inorganic Biochemistry* 100:882-890 (2006).

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, "specifically binds" refers to a molecule (e.g., an antibody) which recognizes and binds another molecule (e.g., an antigen), but does not substantially recognize and bind other molecules. The terms "specific binding," "specifically binds to," or is "specific for" a particular molecule (e.g., an antigen, or an epitope on an antigen), as used herein, can be exhibited, for example, by a molecule having a $K_d$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M.

As used herein, the terms "subject," "individual," or "patient" are used interchangeably and refer to an individual organism, a vertebrate, a mammal, or a human. In certain embodiments, the individual, patient or subject is a human.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. By "treating a cancer" is meant that the symptoms associated with the cancer are, e.g., alleviated, reduced, cured, or placed in a state of remission.

It is also to be appreciated that the various modes of treatment of diseases as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

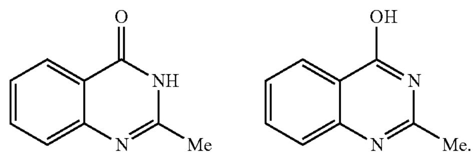 [SMILES: Cc1nc2ccccc2c(=O)[nH]1 ; Cc1nc(O)c2ccccc2n1]

As another example, guanidines may exhibit the following isomeric forms in protic organic solution (e.g., water), also referred to as tautomers of each other:

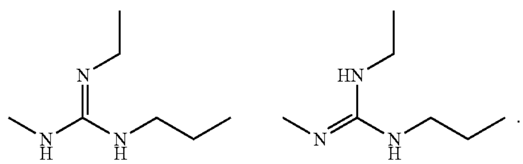

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Pretargeted Radioimmunotherapy (PRIT)

Pre-targeting is a multistep process that resolves the slow blood clearance of tumor targeting antibodies, which contributes to undesirable toxicity to normal tissues such as bone marrow. In pre-targeting, a radionuclide or other diagnostic or therapeutic agent is attached to a small hapten. A pre-targeting bispecific antibody, which has binding sites for the hapten as well as a target antigen, is administered first. Unbound antibody is then allowed to clear from circulation and the hapten is subsequently administered.

DOTA-PRIT has been used to effectively target a beta-emitting radioisotope (e.g., lutetium-177) to GD2- or GPA33-expressing human carcinoma xenografts, thus reducing toxicity to normal tissues such as bone marrow and kidney. Beta-particle emissions (e.g., from $^{177}$Lu-DOTA-Bn haptens) are considered to be low linear energy transfer, with a range of 1-10 nm and 0.1-1 MeV energy. DOTA-PRIT is optimally suited for targeting beta-particle emitting radioactive isotopes of lutetium and yttrium ($^{177}$Lu and $^{90}$Y, respectively) because anti-DOTA C825 (an anti-DOTA scFv) binds DOTA-complexes containing such radiolanthanides with pM affinity.

However, solid tumors are generally radio-resistant. Alpha-particle radiotherapy (e.g., with $^{225}$Ac-DOTA-haptens) on the other hand results in highly potent cell-killing activity with minimal collateral damage via high linear energy transfer alpha particle emissions with a range of 50-80 microns and 5-8 MeV energy. Unlike beta-particles that can deposit their energy over a longer distance, alpha-particle radiotherapy has a high therapeutic potential against small-volume tumors, including minimal residual disease which can be a major cause of cancer relapse. Thus there is a need to increase the effectiveness of DOTA-PRIT radiotherapy with alpha-particle emitters, which have greater therapeutic potential compared to beta-particles.

An inherent limitation of C825 is the variation in binding affinity that the scFv has for various anti-DOTA-haptens, which is highly dependent on the ionic radius of the trivalent rare earth. Previous modeling studies have demonstrated that a hapten-binding affinity of 100 pM is needed for efficient delivery of ionizing radiation in PRIT (assuming conditions of high antigen density and saturating BsAb dose), specifically to achieve near-maximal hapten retention in vascular tumors and micrometastases. C825 was shown to bind DOTA-Bn [S-2-(4-aminobenzyl)-1,4,7,10-tetraazacyclododecane tetraacetic acid chelate] complexes of Y, Lu, or Gd with a $K_d$ (equilibrium dissociation constant, as mean±SD) of 15.4±2.0 pM, 10.8±2.5 pM, or 34.0±5.3 pM, respectively. In contrast, the $K_d$ for DOTA-Bn complexes containing In or Ga was 1.01±0.04 nM or 52±12 nM. Thus, DOTA-PRIT is well suited for targeting beta-particle emitters yttrium-90 and lutetium-177, but is less likely to be compatible with an alpha-particle emitter (e.g., Actinium isotopes).

Preliminary experiments have shown that pretargeting with $^{225}$Ac-DOTA-Bn in vivo using a model DOTA-PRIT system (anti-GD2-DOTA-PRIT) led to statistically significant ($p \leq 0.005$; unpaired, two-tailed Student's t-test) and unremarkable tumor uptake of $^{225}$Ac-DOTA-Bn 24 hours post-injection compared to equimolar administered $^{177}$Lu-DOTA-Bn (as % ID/g; average standard deviation (SD); for $^{225}$Ac-DOTA-Bn (n=5): 0.82±0.17; for $^{177}$Lu-DOTA-Bn (n=5): 10.29±2.87). See WO2019/010299. There were no major differences observed in normal tissue such as blood or kidney (for blood: 0.33±0.03 or 0.49±0.09 for $^{225}$Ac- or $^{177}$Lu-DOTA-Bn, respectively; for kidney: 0.65±0.15 or 0.83±0.10 for $^{225}$Ac- or $^{177}$Lu-DOTA-Bn, respectively; both p>0.05), suggesting that the in vivo fate of the two tracers was similar, and in vivo stability was likely not a limiting factor for tumor localization.

Compositions of the Present Technology

DOTA is a macrocyclic chelating agent that forms stable metal complexes that are irreversible under physiological conditions. DOTA has a molecular weight of 405 Daltons, and exhibits rapid diffusion and renal clearance. DOTA and its variants chelate a wide range of metals including paramagnetic metals and radionuclides. Exemplary metals include yttrium, indium, gallium, gadolinium, europium, terbium, lutetium, copper, bismuth, actinium and all lanthanide metals.

In one aspect, the present disclosure provides a compound of Formula I (I)

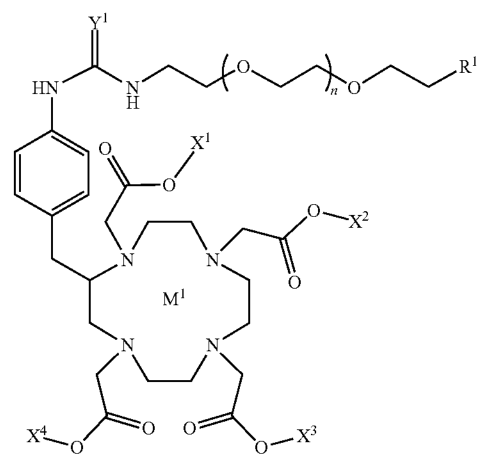

or a pharmaceutically acceptable salt thereof, wherein $M^1$ is a chelated $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $^{160}Gd^{3+}$.

$R^1$ is

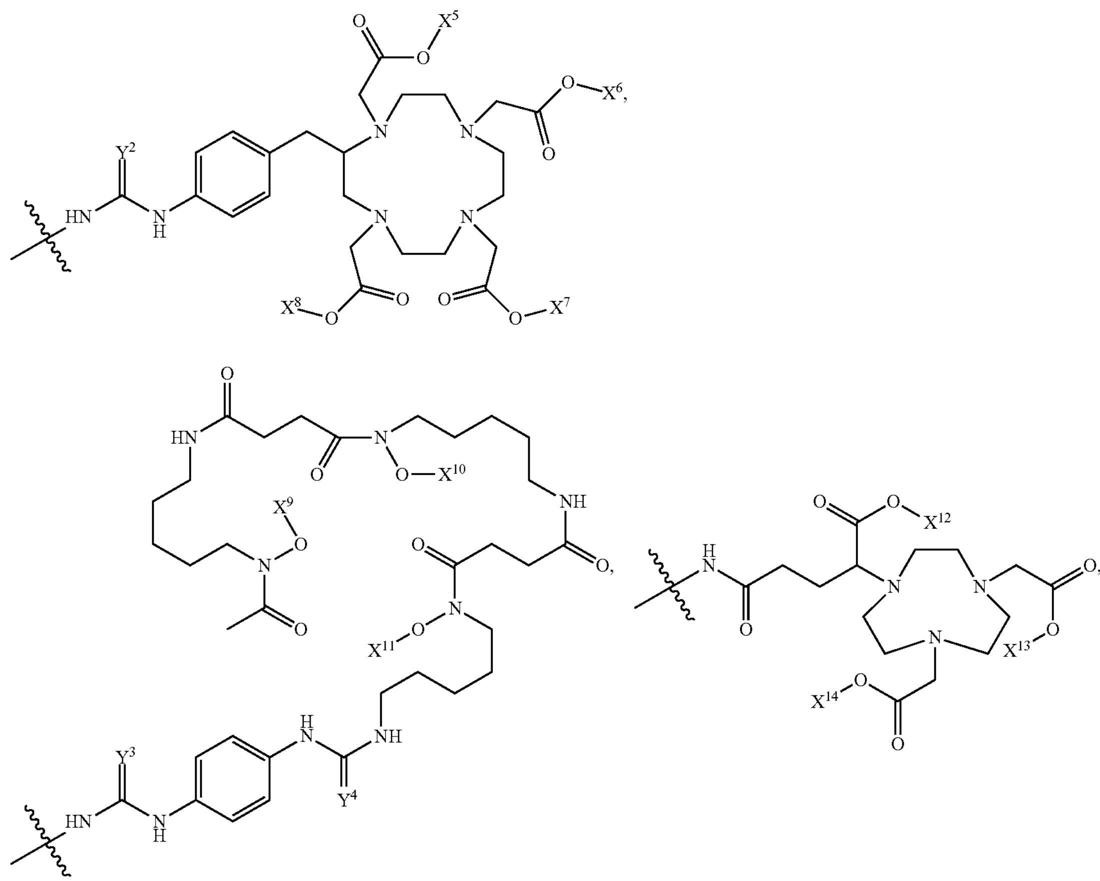

-continued
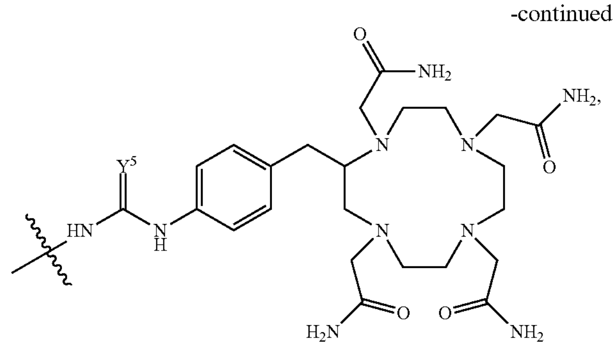
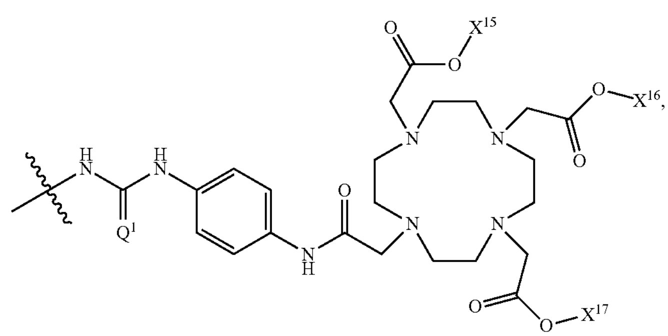
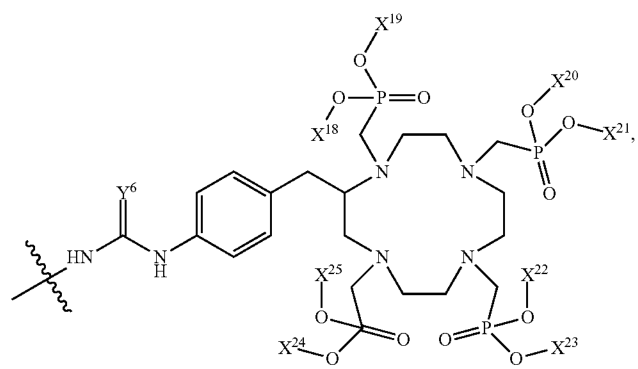
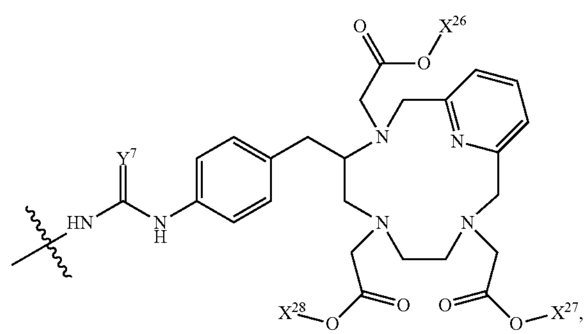

-continued

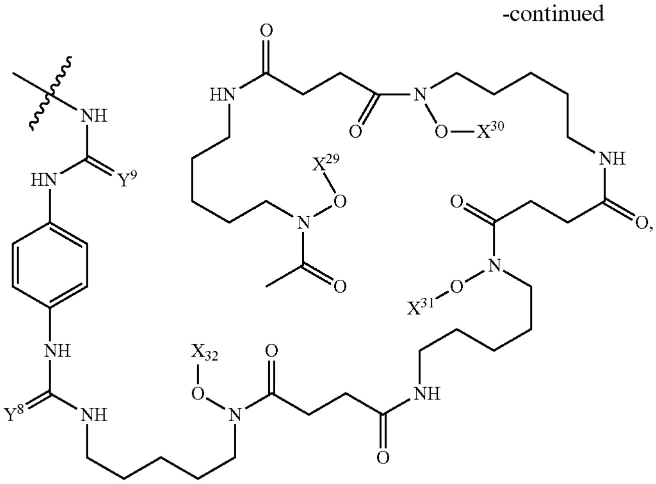

or

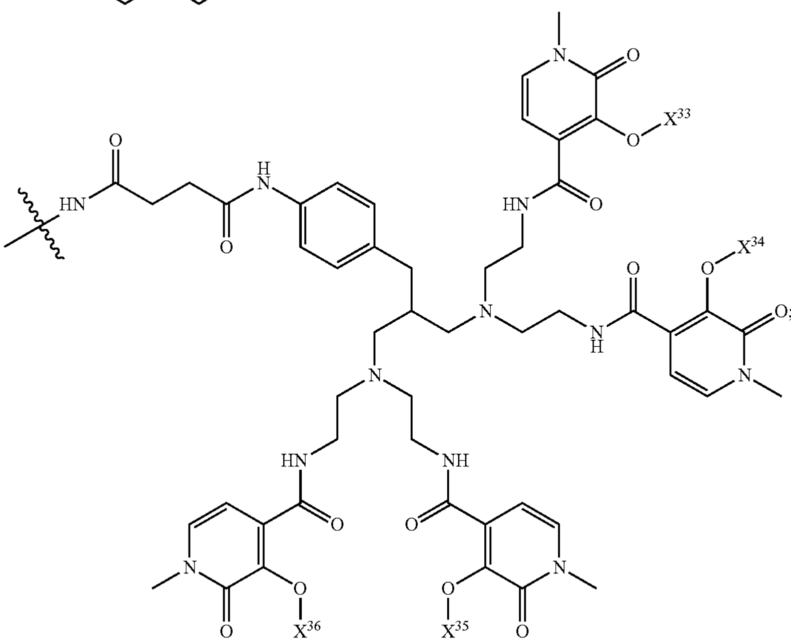

$X^1$, $X^2$, $X^3$, $X^4$, $X^5$, $X^6$, $X^7$, $x^8$, $X^9$, $X^{10}$, $x^{11}$, $X^{12}$, $X^{13}$, $X^4$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, $X^{35}$, and $X^{36}$ are each independently a lone pair of electrons (i.e., providing an oxygen anion) or H; $Y^1$, $Y^2$, $Y^3$, $Y^4$, $Y^5$, $Y^6$, $Y^7$, $Y^8$, and $Y^9$ are each independently S or O; $Q^1$ is S or O; and n is 1, 2, 3, 4, 5, 6, 7, 8, 9, 10, 11, 12, 13, 14, 15, 16, 17, 18, 19, 20, 21, or 22. In certain embodiments, n is 3.

In another aspect, the present disclosure provides a bischelate comprising any of the above compounds of Formula I and a radionuclide cation. In some embodiments, the compound of Formula I can bind a radionuclide cation with a $K_d$ of about 1 pM-1 nM (e.g., about 1-10 pM; 1-100 pM; 5-50 pM; 100-500 pM; or 500 pM-1 nM). In some embodiments, the $K_d$ is in the range of about 1 nM to about 1 pM, for example, no more than about 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 150 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2.5 pM, 2 pM, or 1 pM. In some embodiments, the bischelate is of Formula II (II)

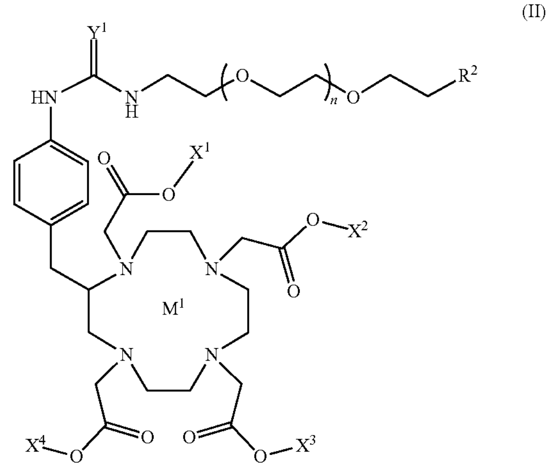

or a pharmaceutically acceptable salt thereof, wherein $M^1$ is a chelated $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $^{160}Gd^{3+}$.
$R^2$ is
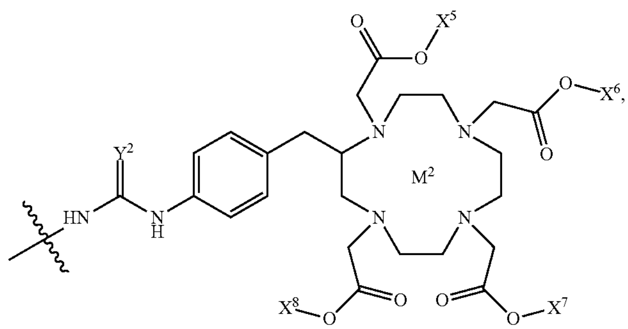
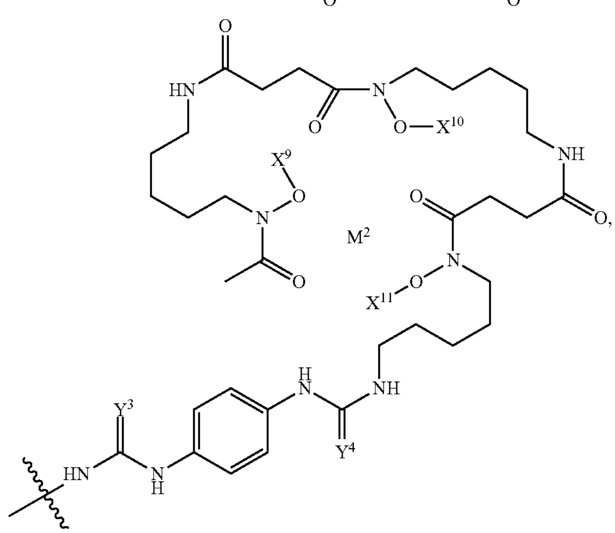
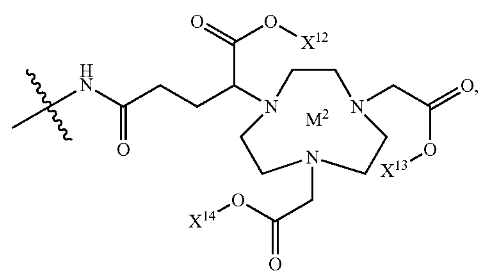
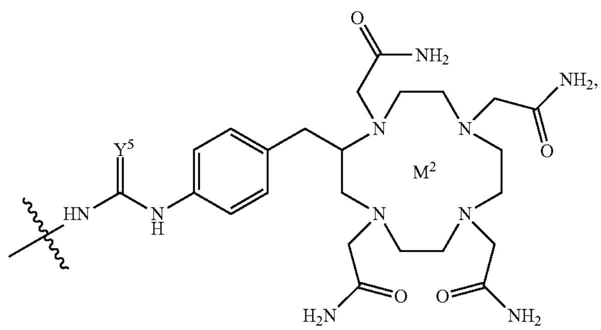
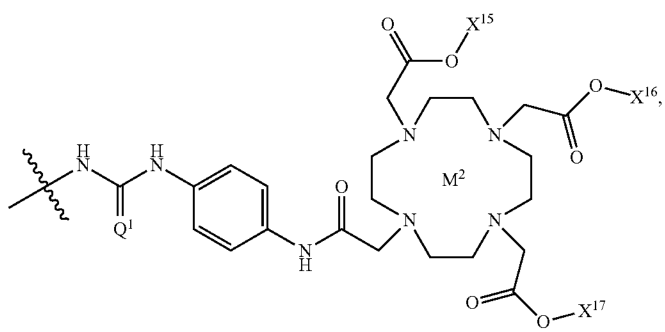

-continued
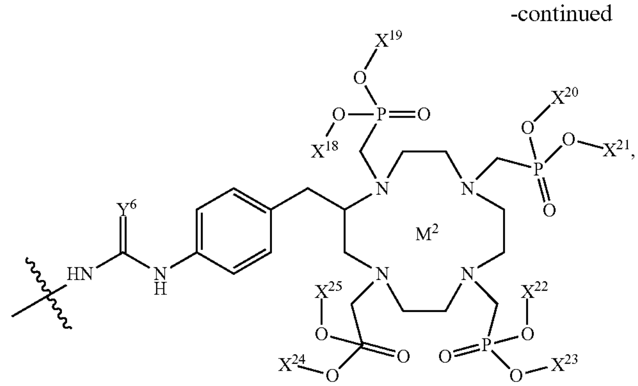
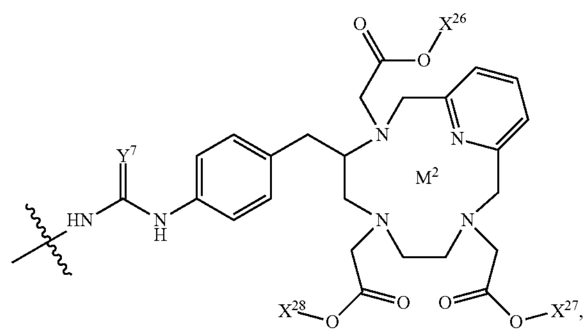
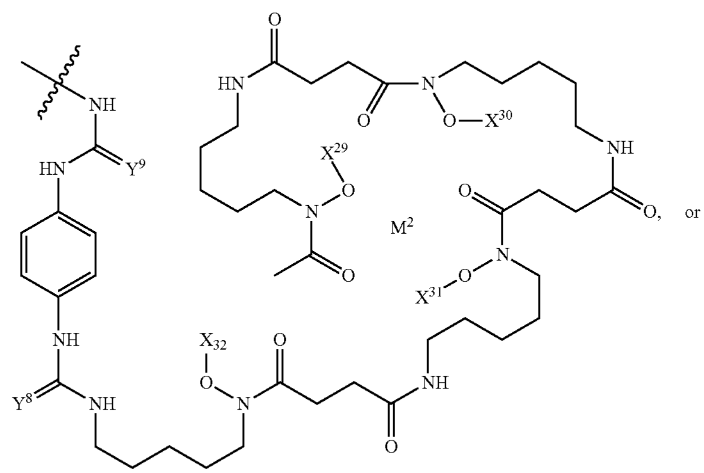
or

-continued

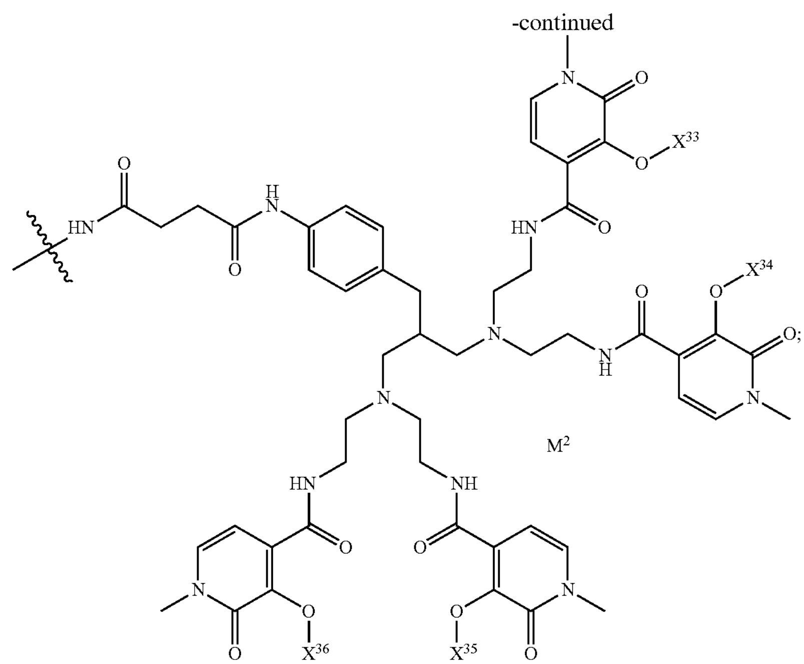

$M^2$ is independently at each occurrence a radionuclide cation chelated by the $R^2$ group; $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, $X^{35}$, and $X^{36}$ are each independently a lone pair of electrons (i.e., providing an oxygen anion) or H; $Y^1$, $Y^2$, $Y^3$, $Y^4$, $Y^5$, $Y^6$, $Y^7$, $Y^8$, and $Y^9$ are each independently S or O; $Q^1$ is S or O; and n is 1, 2, 3, 4, 5, 6, 7, 8, 9, 10, 11, 12, 13, 14, 15, 16, 17, 18, 19, 20, 21, or 22. In certain embodiments, n is 3. Additionally or alternatively, in some embodiments, the radionuclide cation is a divalent cation or a trivalent cation.

In any and all embodiments, the compound of Formula II includes a radionuclide cation that is chelated by the $R^2$ group. The radionuclide cation may be an alpha particle-emitting isotope, a beta particle-emitting isotope, an Auger-emitter, or a combination of any two or more thereof. Examples of alpha particle-emitting isotopes include, but are not limited to, $^{213}Bi$, $^{211}At$, $^{225}Ac$, $^{152}Dy$, $^{212}Bi$, $^{223}Ra$, $^{219}Rn$, $^{215}Po$, $^{211}Bi$, $^{221}Fr$, $^{217}At$, and $^{255}Fm$. Examples of beta particle-emitting isotopes include, but are not limited to, $^{86}Y$, $^{90}Y$, $^{89}Sr$, $^{165}Dy$, $^{186}Re$, $^{188}Re$, $^{177}Lu$, and $^{67}Cu$. Examples of Auger-emitters include $^{111}In$, $^{67}Ga$, $^{51}Cr$, $^{58}Co$, $^{99m}Tc$, $^{103m}Rh$, $^{195m}Pt$, $^{119}Sb$, $^{161}Ho$, $^{189m}Os$, $^{192}Ir$, $^{201}Tl$, and $^{203}Pb$. In some embodiments of the compounds of Formula II, the radionuclide cation is $^{89}Zr$, $^{68}Ga$, $^{203}Pb$, $^{212}Pb$, $^{227}Th$, or $^{64}Cu$.

In some embodiments, the radionuclide cation has a decay energy in the range of 20 to 6,000 keV. Decay energies can be within the range of 60 to 200 keV for an Auger emitter, 100-2,500 keV for a beta emitter, and 4,000-6,000 keV for an alpha emitter. Maximum decay energies of useful beta-particle-emitting nuclides can range from 20-5,000 keV, 100-4,000 keV, or 500-2,500 keV. Decay energies of useful Auger-emitters can be <1,000 keV, <100 keV, or <70 keV. Decay energies of useful alpha-particle-emitting radionuclides can range from 2,000-10,000 keV, 3,000-8,000 keV, or 4,000-7,000 keV.

In another aspect, the present disclosure provides a complex comprising the compound of Formula I and a bispecific antibody that recognizes and binds to the compound and a tumor antigen target. The present disclosure also provides a complex comprising the bischelate of Formula II and a bispecific antibody that binds to the bischelate and a tumor antigen target. In any of the above embodiments of the complexes disclosed herein, the bispecific antibody may be an infinite binder. In some embodiments, the bispecific antibody comprises an antigen binding fragment of C825 (See Cheal et al., *Mol Cancer Ther.* 13(7):1803-12 (2014)) or 2D12.5 (Corneillie et al., *J. Inorganic Biochemistry* 100:882-890 (2006)). Additionally or alternatively, in any of the above embodiments of the complexes disclosed herein, the bispecific antibody comprises an antigen binding fragment of C825 with a G54C substitution. Additionally or alternatively, in any of the above embodiments of the complexes disclosed herein, the bispecific antibody comprises an antigen binding fragment of 2D12.5 with a G54C substitution.

In any of the above embodiments of the complexes disclosed herein, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM. Additionally or alternatively, in some embodiments of the complex, the bispecific antibody binds to the compound or the bischelate with a $K_d$ that is lower than or equal to 100 nM-95 nM, 95-90 nM, 90-85 nM, 85-80 nM, 80-75 nM, 75-70 nM, 70-65 nM, 65-60 nM, 60-55 nM, 55-50 nM, 50-45 nM, 45-40 nM, 40-35 nM, 35-30 nM, 30-25 nM, 25-20 nM, 20-15 nM, 15-10 nM, 10-5 nM, 5-1 nM, 1 nM-950 pM, 950 pM-900 pM, 900 pM-850 pM, 850 pM-800 pM, 800 pM-750 pM, 750 pM-700 pM, 700 pM-650 pM, 650 pM-600 pM, 600 pM-550 pM, 550 pM-500 pM, 500 pM-450 pM, 450 pM-400 pM, 400 pM-350 pM, 350 pM-300 pM, 300 pM-250 pM, 250 pM-200 pM, 200 pM-150 pM, 150 pM-100 pM, 100 pM-50 pM, 50 pM-40 pM, 40 pM-30 pM, 30 pM-20 pM, 20 pM-10 pM, 9 pM, 8 pM, 7 pM, 6 pM, 5 pM, 4 pM, 3 pM, 2.5 pM, 2 pM, 1.5 pM, or 1 pM.

Diagnostic and Therapeutic Methods of the Present Technology

In one aspect, the present disclosure provides a method for detecting tumors in a subject in need thereof comprising (a) administering to the subject an effective amount of a complex comprising the bischelate of Formula II and a bispecific antibody that binds to the bischelate and a tumor antigen target, wherein the complex is configured to localize to a tumor expressing the tumor antigen target recognized by the bispecific antibody of the complex; and (b) detecting the presence of tumors in the subject by detecting radioactive levels emitted by the complex that are higher than a reference value. Also disclosed herein is a method for detecting tumors in a subject in need thereof comprising (a) administering an effective amount of an anti-DOTA bispecific antibody to the subject, wherein the anti-DOTA bispecific antibody is configured to localize to a tumor expressing a tumor antigen target; (b) administering an effective amount of the bischelate of Formula II to the subject, wherein the bischelate is configured to bind to the anti-DOTA bispecific antibody, and (c) detecting the presence of tumors in the subject by detecting radioactive levels emitted by the bischelate that are higher than a reference value. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the bischelate of Formula II is administered after a time period that may be sufficient to permit clearance of unbound anti-DOTA bispecific antibody. Additionally or alternatively, in some embodiments of the methods disclosed herein, the tumors are solid tumors or liquid tumors. In any and all embodiments of the methods disclosed herein, detecting tumors in the subject comprises imaging tumors in vivo and/or measuring the amount or dosage of radiation absorbed by the subject. In some embodiments, the subject is human.

In another aspect, the present disclosure provides a method for selecting a subject for pretargeted radioimmunotherapy comprising (a) administering to the subject an effective amount of a complex comprising the bischelate of Formula II and a bispecific antibody that binds to the bischelate and a tumor antigen target, wherein the complex is configured to localize to a tumor expressing the tumor antigen target recognized by the bispecific antibody of the complex; (b) detecting radioactive levels emitted by the complex; and (c) selecting the subject for pretargeted radioimmunotherapy when the radioactive levels emitted by the complex are higher than a reference value. Also provided herein is a method for selecting a subject for pretargeted radioimmunotherapy comprising (a) administering an effective amount of an anti-DOTA bispecific antibody to the subject, wherein the anti-DOTA bispecific antibody is configured to localize to a tumor expressing a tumor antigen target; (b) administering an effective amount of the bischelate of Formula II to the subject, wherein the bischelate is configured to bind to the anti-DOTA bispecific antibody, (c) detecting radioactive levels emitted by the bischelate, and (d) selecting the subject for pretargeted radioimmunotherapy when the radioactive levels emitted by the bischelate are higher than a reference value. Additionally or alternatively, in some embodiments of the methods disclosed herein, the tumors are solid tumors or liquid tumors. In some embodiments, the subject is human.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having cancer. The cancer may be selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, and head-and-neck cancer. In some embodiments, the brain cancer is a pituitary adenoma, a meningioma, a neuroblastoma, or a craniopharyngioma.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally or intranasally. In certain embodiments, the complex is administered into the cerebral spinal fluid or blood of the subject.

In some embodiments of the methods disclosed herein, the radioactive levels emitted by the complex are detected between 4 to 24 hours after the complex is administered. In certain embodiments of the methods disclosed herein, the radioactive levels emitted by the complex are expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, *J Nucl Med.* 45(9):1431-4 (2004). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with cancer comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of Formula II to the subject, wherein the bischelate is configured to bind to the anti-DOTA bispecific antibody. In some embodiments, the subject is human. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the bischelate of Formula II is administered after a time period that may be sufficient to permit clearance of unbound anti-DOTA bispecific antibody.

The bischelate may be administered at any time between 1 minute to 4 or more days following administration of the anti-DOTA bispecific antibody. For example, in some embodiments, the bischelate is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the bischelate may be administered at any time after 4 or more days following administration of the anti-DOTA bispecific antibody.

Additionally or alternatively, in some embodiments, the method further comprises administering an effective amount of a clearing agent to the subject prior to administration of the bischelate. A clearing agent can be any molecule (dextran or dendrimer or polymer) that can be conjugated with C825-hapten. In some embodiments, the clearing agent is no more than 2000 kD, 1500 kD, 1000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, or 5 kD. In some embodiments, the clearing agent is a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.).

In some embodiments, the clearing agent and the bischelate of Formula II are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody (optionally so that relevant tumor cells are saturated); (ii) administration of a bischelate of Formula II and, optionally a clearing agent; (iii) optional additional administration of the bischelate of Formula II and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Additionally or alternatively, in some embodiments of the method, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM.

Additionally or alternatively, in some embodiments of the method, the anti-DOTA bispecific antibody and/or the bischelate is administered intravenously, intramuscularly, intraarterially, intrathecally, intracapsularly, intraorbitally, intradermally, intraperitoneally, transtracheally, subcutaneously, intracerebroventricularly, orally or intranasally.

In one aspect, the present disclosure provides a method for increasing tumor sensitivity to radiation therapy in a subject diagnosed with cancer comprising administering to the subject an effective amount of a complex comprising the bischelate of Formula II and a bispecific antibody that recognizes and binds to the bischelate and a tumor antigen target, wherein the complex is configured to localize to a tumor expressing the tumor antigen target recognized by the bispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments, the subject is human.

In another aspect, the present disclosure provides a method for treating cancer in a subject in need thereof comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of Formula II to the subject, wherein the bischelate is configured to bind to the anti-DOTA bispecific antibody. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the bischelate of Formula II is administered after a time period that may be sufficient to permit clearance of unbound anti-DOTA bispecific antibody. In some embodiments, the subject is human.

Accordingly, in some embodiments, the method further comprises administering an effective amount of a clearing agent to the subject prior to administration of the bischelate. The bischelate may be administered at any time between 1 minute to 4 or more days following administration of the anti-DOTA bispecific antibody. For example, in some embodiments, the bischelate is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the bischelate may be administered at any time after 4 or more days following administration of the anti-DOTA bispecific antibody.

The clearing agent may be a 500 kD aminodextran-DOTA conjugate (e.g., 500 kD dextran-DOTA-Bn (Y), 500 kD dextran-DOTA-Bn (Lu), or 500 kD dextran-DOTA-Bn (In)

etc.). In some embodiments, the clearing agent and the bischelate of Formula II are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody (optionally so that relevant tumor cells are saturated); (ii) administration of a bischelate of Formula II and, optionally a clearing agent; (iii) optional additional administration of the bischelate of Formula II and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Also provided herein are methods for treating cancer in a subject in need thereof comprising administering to the subject an effective amount of a complex comprising the bischelate of Formula II and a bispecific antibody that recognizes and binds to the bischelate and a tumor antigen target, wherein the complex is configured to localize to a tumor expressing the tumor antigen target recognized by the bispecific antibody of the complex. The therapeutic effectiveness of such a complex may be determined by computing the area under the curve (AUC) tumor:AUC normal tissue ratio. In some embodiments, the complex has a AUC tumor:AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

The methods for treating cancer may further comprise sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11. In some embodiments, the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, and head-and-neck cancer. In some embodiments, the subject is human.

The methods of treating cancer disclosed herein may further comprise monitoring the tumor progression over time after administration of (a) the bischelate of Formula II or (b) the complex comprising the bischelate of Formula II and the bispecific antibody that recognizes and binds to the bischelate and the tumor antigen target.

Kits

The present technology provides kits containing components suitable for treating or diagnosing cancer in a patient. In one aspect, the kits comprise a compound of the present technology, at least one anti-DOTA BsAb, and instructions for use. The kits may further comprise a clearing agent (e.g., 500 kDa aminodextran conjugated to DOTA or 500 kD dextran-DOTA-Bn (Y)) and/or one or more radionuclides.

In some embodiments, the at least one anti-DOTA BsAb binds to a tumor antigen target selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), and Ki-67. Additionally or alternatively, in some embodiments, the at least one anti-DOTA BsAb binds to a tumor antigen target selected from the group consisting of CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM. The at least one anti-DOTA BsAb may be provided in the form of a prefilled syringe or autoinjection pen containing a sterile, liquid formulation or lyophilized preparation of the antibody (e.g., Kivitz et al., *Clin. Ther.* 28:1619-29 (2006)).

Additionally or alternatively, in some embodiments of the kits of the present technology, the one or more radionuclides are selected from among $^{213}Bi$, $^{211}At$, $^{225}Ac$, $^{152}Dy$, $^{212}Bi$, $^{223}Ra$, $^{219}Rn$ $^{215}Po$, $^{211}Bi$, $^{221}Fr$, $^{217}At$, and $^{255}Fm$. Additionally or alternatively, in certain embodiments, the one or more radionuclides are selected from the group consisting of $^{86}Y$, $^{90}Y$, $^{89}Sr$, $^{165}Dy$, $^{186}Re$, $^{188}Re$, $^{177}Lu$, $^{67}Cu$, $^{111}In$, $^{67}Ga$, $^{51}Cr$, $^{58}Co$, $^{99m}Tc$, $^{103m}Rh$, $^{195m}Pt$, $^{119}Sb$, $^{161}Ho$, $^{189m}Os$, $^{192}Ir$, $^{201}Tl$, $^{203}Pb$, $^{68}Ga$, $^{227}Th$, and $^{64}Cu$.

If the kit components are not formulated for oral administration, a device capable of delivering the kit components through some other route may be included. Examples of such devices include syringes (for parenteral administration) or inhalation devices.

The kit components may be packaged together or separated into two or more containers. In some embodiments, the containers may be vials that contain sterile, lyophilized formulations of a DOTA hapten and/or BsAb composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers.

EXAMPLES

Example 1: Materials and Methods for Generating the Compositions of the Present Technology General. DOTA-Bn-isothiocyanate (p-SCN-Bn-DOTA) was purchased from Macrocyclics, Inc. (Plano, TX) and Amine-$PEG_4$-DOTA was purchased from CheMatech (Dijon, France). Optima™ grade hydrochloric acid was purchased from Thermo Fisher Scientific (Waltham, MA). Chelex-100 resin, 200-400 mesh was purchased from Bio-Rad Laboratories (Hercules, CA). PD-10 gel-filtration size-exclusion columns (containing 8.3 mL of Sephadex™ G-25 resin/column) were purchased from GE Healthcare Life Sciences (Pittsburgh, PA). All other reagents and synthesis-grade chemicals were purchased from Sigma-Aldrich (St. Louis, MO) and used without further purification. All solvents used for HPLC analysis (HPLC grade) and compound purification were also purchased from Thermo Fisher Scientific (Waltham, MA). All buffers and solutions were prepared using ultrapure water (18 MΩ-cm resistivity).

All liquid chromatography mass spectrometry (LC/MS) data was obtained using a Waters Autopure system (Milford, MA) comprising the following instrumentation: 2767 Sample Manager, 2545 Binary Gradient Module, System Fluidics Organizer, 2424 Evaporative Light Scattering Detector, 2998 Photodiode Array Detector, 3100 Mass Detector. HPLC solvents (solvent A, 0.05% TFA in water; solvent B, 0.05% TFA in acetonitrile) were filtered prior to use. The analytical method was 5-25% solvent B in 10 min, 1.2 mL/min flow rate. Analytical columns: Waters XBridge BEH300 (Milford, MA), C4, 3.5 μm, 4.6×50 mm and C18, 4 μm, 4.6×50 mm. Preparative method: 5-25% solvent B in 30 min, 20 mL/min flow rate. Preparative column: Waters XBridge Prep (Milford, MA) C18, 4 μm, Optimum Bed Density, 19×150 mm.

All NMR data were obtained with either a Bruker AV500 or AV600 instruments (Bruker, Billerica, MA) at ambient temperature. The following abbreviations were used: singlet (s), broad singlet (bs), doublet (d), triplet (t), quartet (q), pentet (p), doublet of a doublet (dd), multiplet (m).

All PET imaging experiments were conducted on a Focus 120 MicroPET camera (Siemens, Knoxville, TN) dedicated small-animal scanner.

p-SCN-Bn-DOTA·$Lu^{3+}$ Complex:

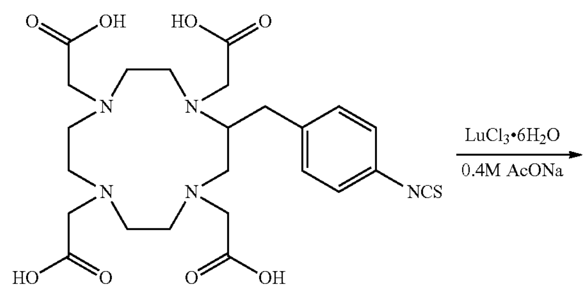

-continued

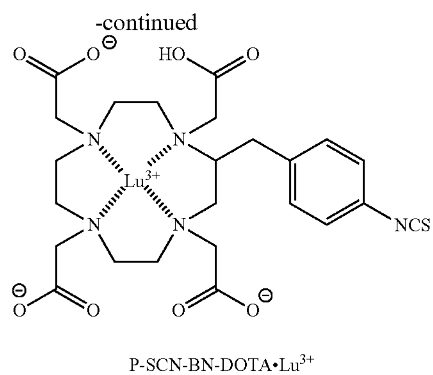

P-SCN-BN-DOTA•$Lu^{3+}$

To a solution of $LuCl_3·6H_2O$ (142 mg, 365 μmol) in 0.6 mL NaOAc (0.4 M solution) was added p-SCN-Bn-DOTA·2.5HCl·2.5$H_2O$ (50 mg, 73 μmol). The mixture was stirred at room temperature (about 21° C.) overnight. Purification was performed by C-18 column using 0-40% ACN/water as gradient to provide a major isomer 31.2 mg (60.5%) and a minor isomer 8 mg (15.2%).

Isolated major isomer (p-SCN-Bn-DOTA·$Lu^{3+}$ complex): $^1H$ NMR ($D_2O$): 7.24 (d, 2H), 7.19 (d, 2H), 3.62-3.48 (m, 3H), 3.42-3.18 (m, 8H), 2.95-3.1 (m, 2H), 2.37-2.82 (m, 11H), 2.12 (d, 1H). MS calculated for $C_{24}H_{30}LuN_5O_8S$ $[M+1]^+$=724.13, Found: 724.18, Negative mode: 722.11. HPLC, C-18, 5-50% gradient of acetonitrile in water containing 0.01% TFA. Peak $R_f$=4.35 minutes in an 8 minute run.

Example 2: Synthesis of DOTA·$Lu^{3+}$-PEG 4-DFO

Scheme 1 provides a synthetic route to provide DOTA·$Lu^{3+}$-PEG 4-DFO of the present technology. Experimental details of the synthesis are provided thereafter.

Scheme 1.

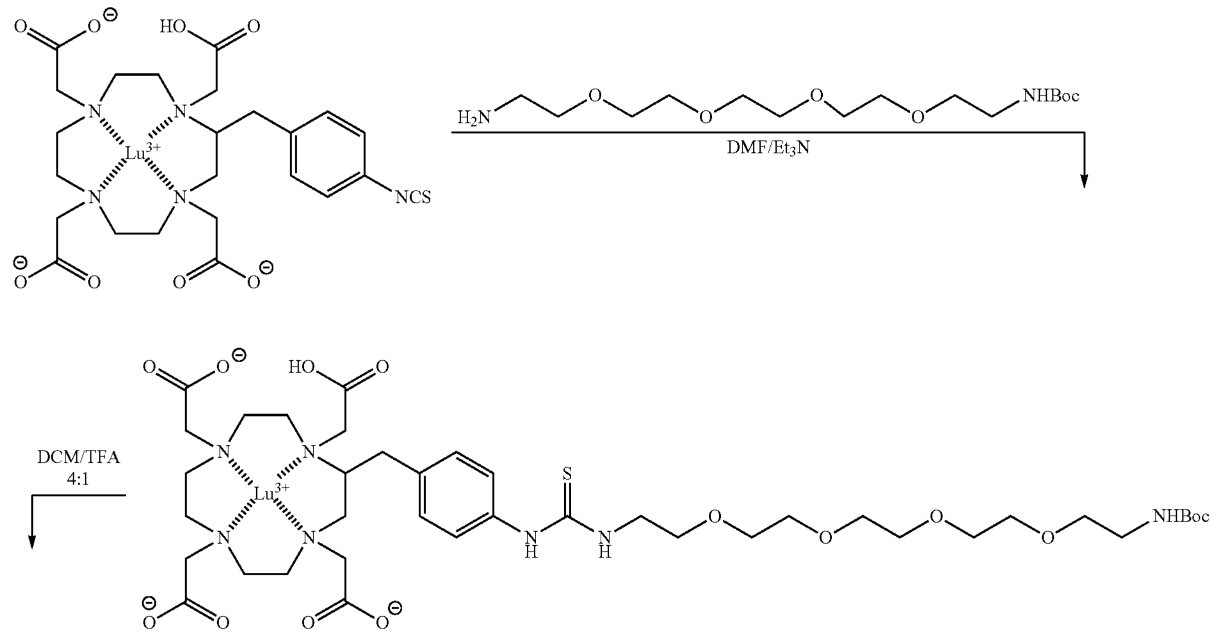

-continued

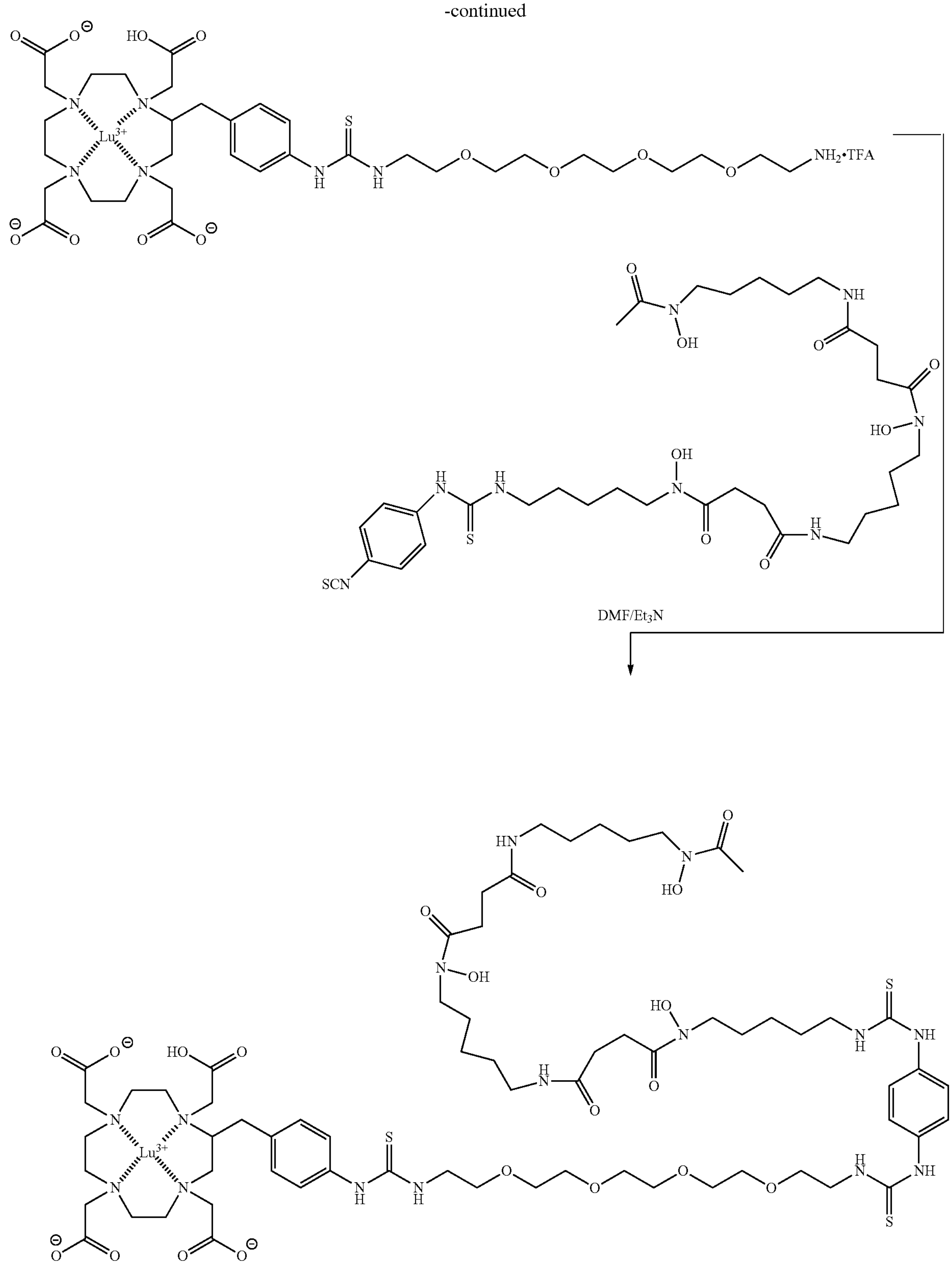

DOTA-$Lu^{3+}$-PEG 4-NHBoc p-SCN-Bn-DOTA $Lu^{31}$ complex (major isomer of Example 1) (30 mg, 41.5 μmol) and Boc-NH-PEG 4-$NH_2$ (17 mg, 50.5 μmol) were added to DMF (0.8 mL), followed by addition of $Et_3N$ (35 μL), and the resulting mixture stirred at room temperature (about 21° C.) overnight. Solvent was removed by vacuum evaporation, then dried over high vacuum. The resulting product was used directly in the next reaction.

Bn-DOTA.$Lu^{3+}$-PEG 4-$NH_2$. TFA

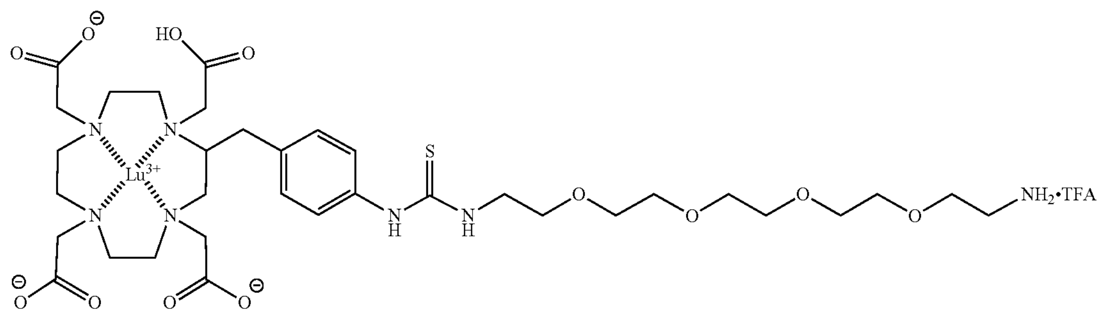

DOTA-$Lu^{3+}$-PEG 4-NHBoc was dissolved in a 4:1 (v/v) solution of DCM/TFA (0.8 mL), and the resulting colorless mixture was stirred at room temperature (about 21° C.) for 40 min. Solvents were then removed by vacuum evaporation, and the residue was purified by HPLC, C-18 reverse phase column, using the gradient 5-40% acetonitrile (containing 0.05% TFA) in water (containing 0.05% TFA). Subsequent lyophilization provided the desired DOTA-$Lu^{3+}$-PEG4-$NH_2$ TFA salt (21 mg, 53%) as a white foam.

Dota-$Lu^{3+}$-PEG 4-DFO

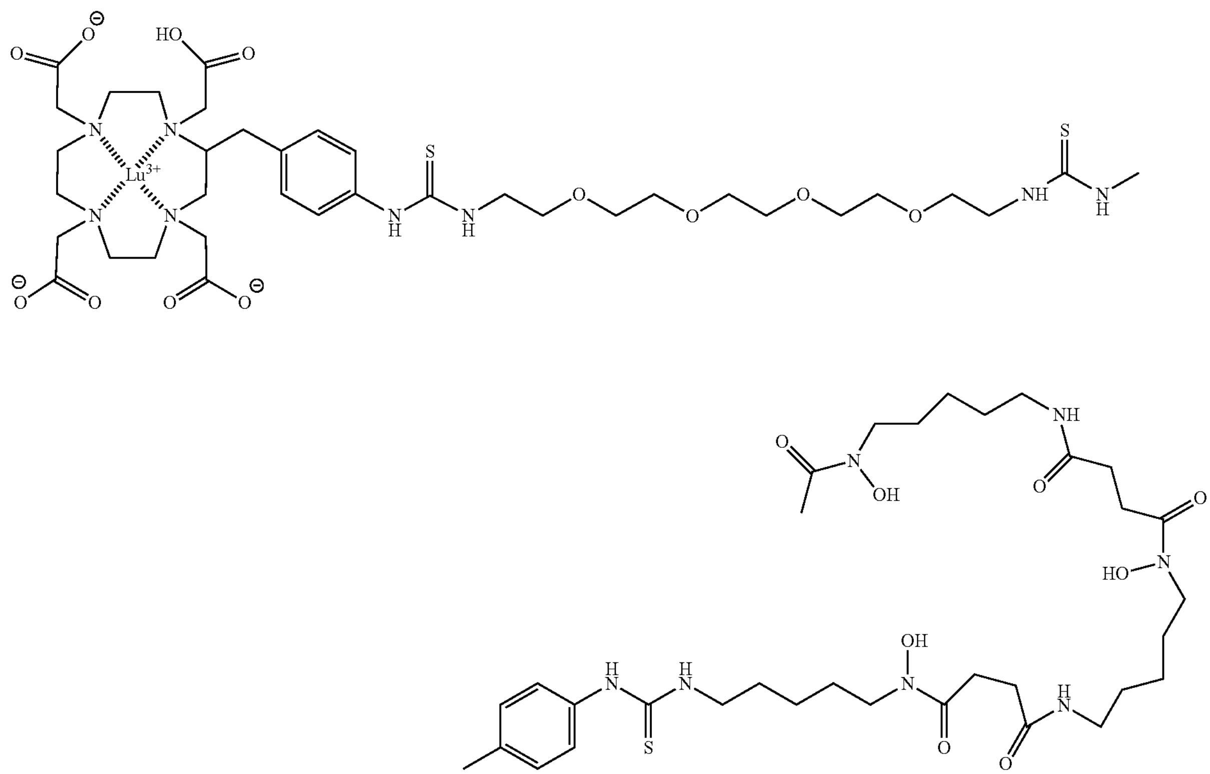

At room temperature (about 21° C.), a solution of Dota-$Lu^{3+}$-PEG (4)-$NH_2$. TFA salt (21 mg, 21.9 μmol) and DFO-SCN (18 mg, 23.9 μmol) in DMF (0.8 mL) was treated with $Et_3N$ (15 μL), and stirring was at room temperature was maintained for an overnight period. The volatiles were then removed under vacuum, and the residue was then purified by reverse phase HPLC using the gradient 5-50% acetonitrile (containing 0.05% TFA) in water (containing 0.05% TFA). DOTA-$Lu^{3+}$-PEG 4-DFO (37.2 mg, 91%) was isolated as a white foam after lyophilization of the appropriate fractions. $^1$H NMR, $D_2O$: 7.23-7.17 (m, 8H), 3.70-2.90 (m, 45H), 2.81-2.30 (m, 19 H), 2.16 (d, 1H), 2.02-2.05 (m, 3H), 1.60-1.51 (m, 8H), 1.44-1.39 (m, 4H), 1.22-1.19 (m, 6H). LCMS: Rf: 3.63 Minutes within a 8 minutes' run. MS calculated for $C_{67}H_{106}LuN_{15}O_{20}S_3$ $[M+1]^+$=1712.64, $[M+1]^{2+}$=856.32. Found: 856.81. In negative mode: calculated, $[M-1]^{2=}$=855.31. Found: 855.37.

Notably, utilizing different isothiocyantates in a similar reaction with DOTA-$Lu^{3+}$-$PEG_4$-$NH_2$ TFA provides for other compounds and compositions of the present technology. For example, utilizing PCTA-isothiocyanate (illustrated below in Scheme 3) or a salt thereof (e.g., the tris-HCl salt of PCTA-isothiocyanate) instead of DFO-SCN provides DOTA·$Lu^{3+}$-$PEG_4$-PCTA of the present technology, illustrated in Scheme 3.

Scheme 3.
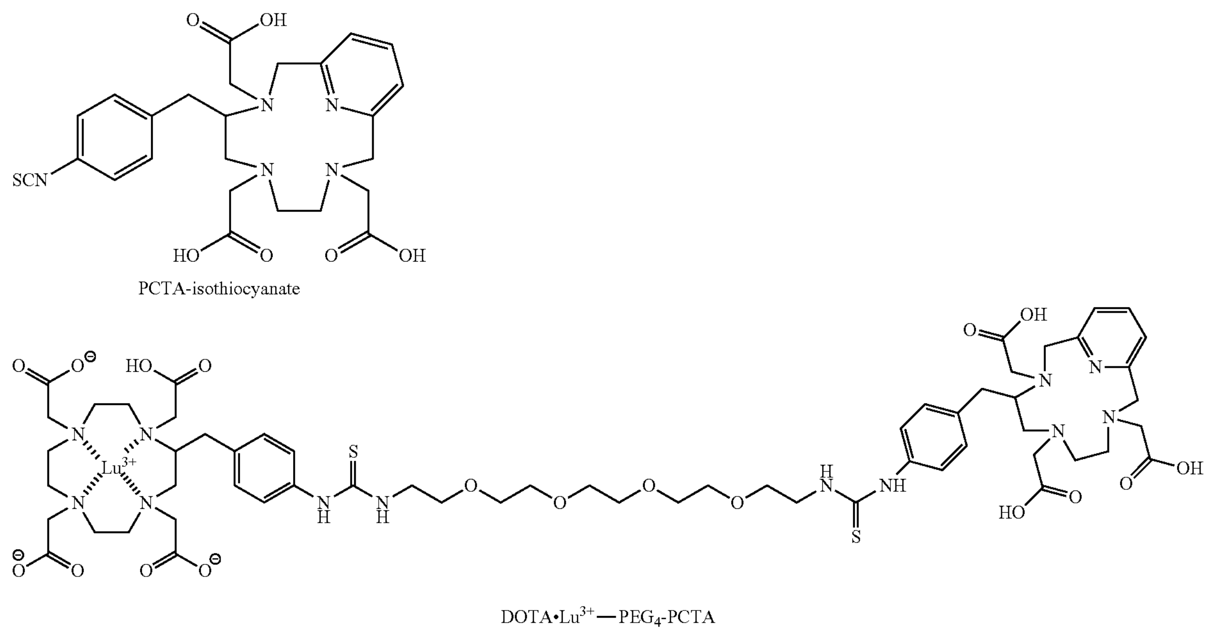
PCTA-isothiocyanate
DOTA•$Lu^{3+}$—$PEG_4$-PCTA
Example 3: Synthesis of DOTA·$Lu^{3+}$-PEG 4-DOTA
Scheme 2 provides a synthetic route to provide DOTA·$Lu^{3+}$-PEG 4-DOTA of the present technology. Experimental details of the synthesis are provided thereafter.
Scheme 2.
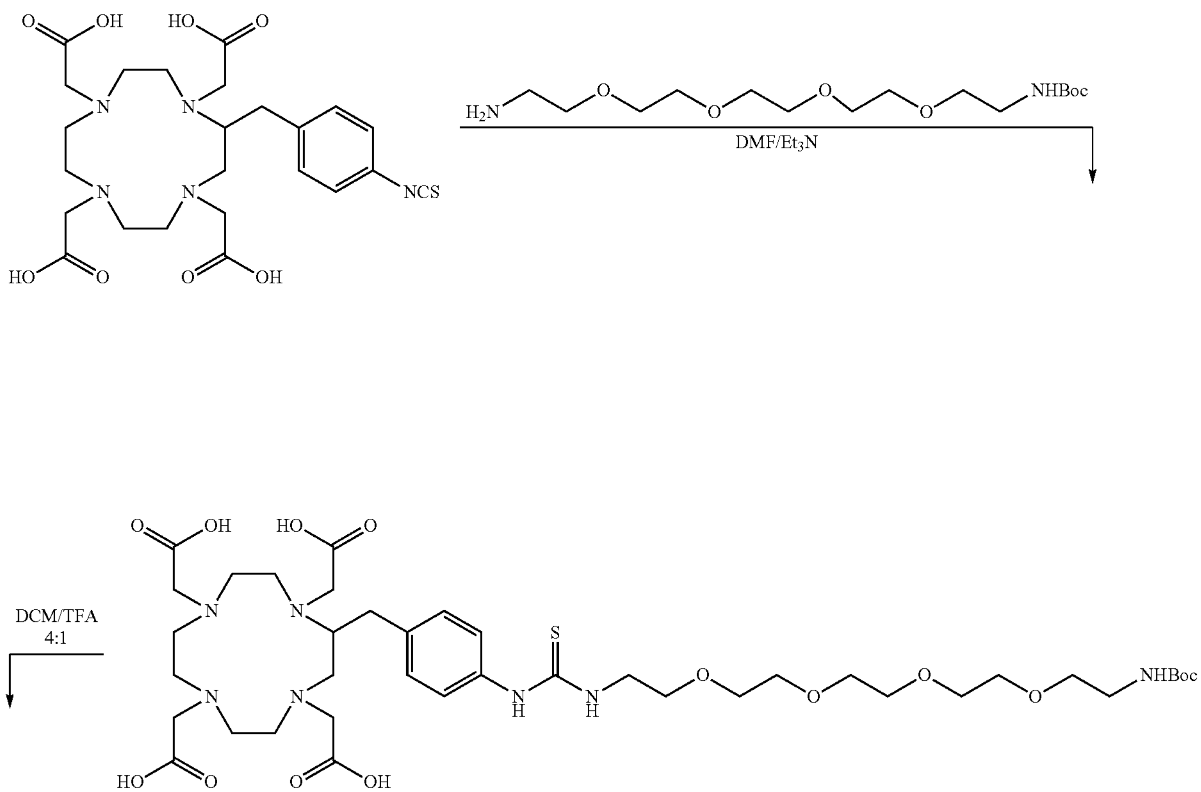

-continued

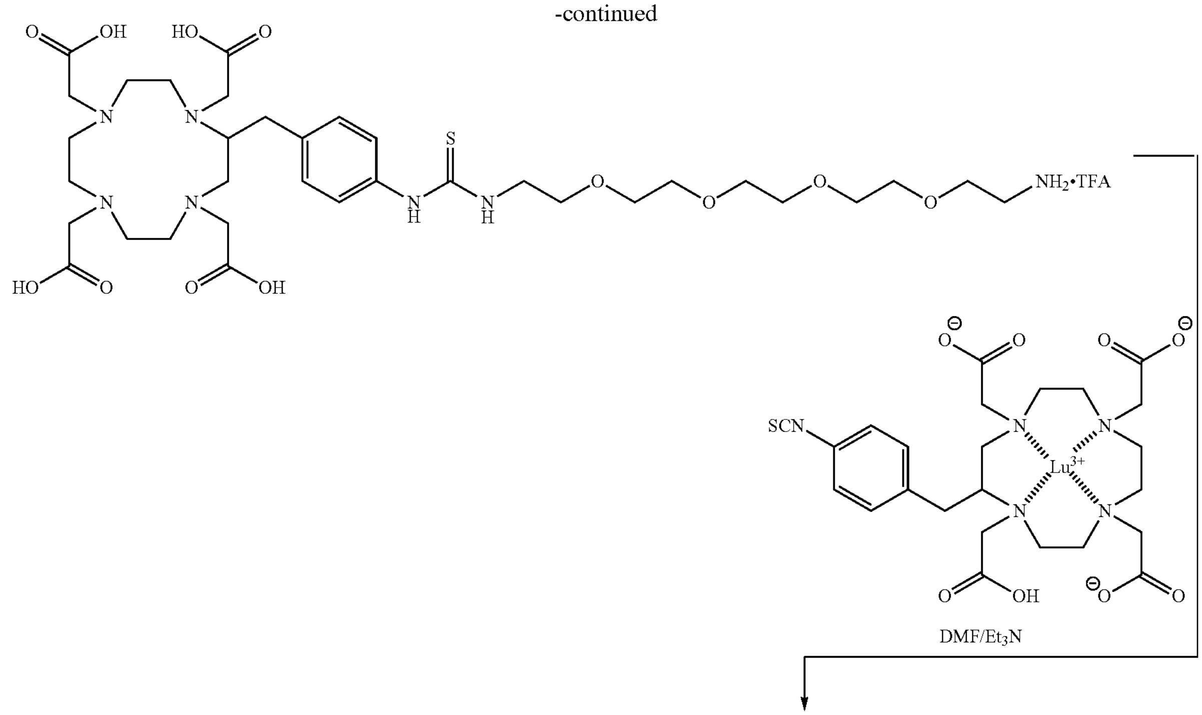

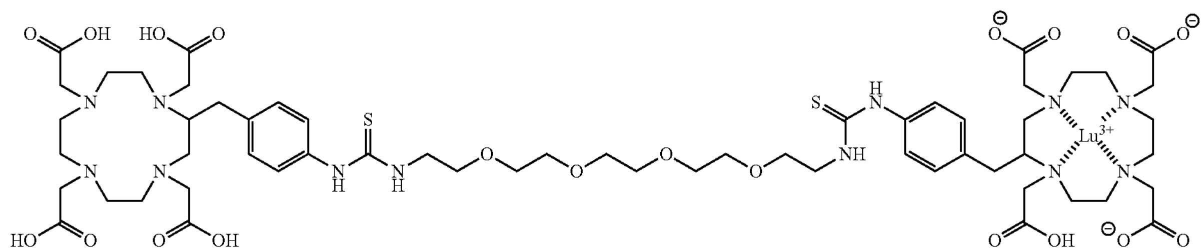

DOTA-PEG 4-NHBoc

At room temperature (about 21° C.), P—SCN—Bn-DOTA (30 mg, 54.4 μmol) and Boc-NH-PEG 4-$NH_2$ (18 mg, 53.5 μmol) were dissolved in anhydrous DMF (0.7 mL) the resulting solution was treated with $Et_3N$ (36 μL). The mixture was stirred at room temperature overnight. Solvents were then removed by vacuum evaporation, and the residue was dried over high vacuum. This was submitted directly in the next step.

DOTA-PEG 4-$NH_2$·TFA

DOTA-PEG 4-NHBoc was dissolved in a 4:1 (v/v) DCM/TFA (0.8 mL), and the resulting colorless mixture was stirred at RT for 40 min. The volatiles were then removed by evaporation, and the residue was purified by reverse phase C-18 HPLC using the gradient 5-40% acetonitrile (containing 0.05% TFA) in water (containing 0.05% TFA). DOTA-PEG 4-$NH_2$·TFA (20 mg, 47%) was obtained after lyophilization of the appropriate fractions.

DOTA·$Lu^{3+}$-PEG 4-DOTA

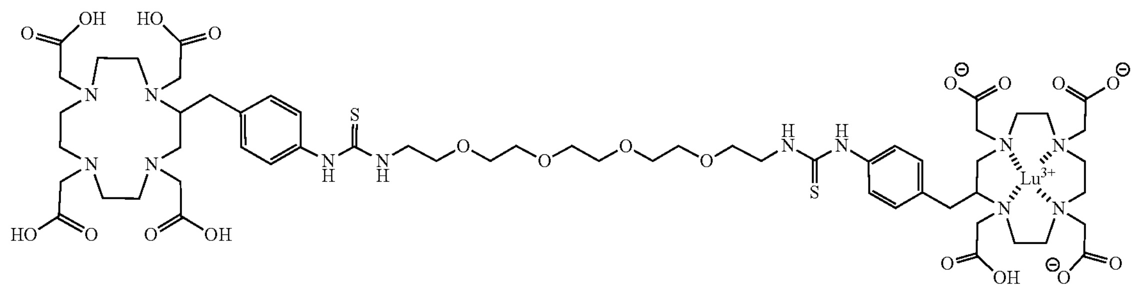

At room temperature (about 21° C.), DOTA-PEG 4-$NH_2$·TFA salt (20 mg, 25.4 μmol) and DOTA·$Lu^{3+}$-SCN major isomer complex (15.3 mg, 21.1 μmol) were mixed in anhydrous DMF (0.8 mL) and then treated with $Et_3N$ (15 μL). The reaction was stirred room temperature under argon atmosphere overnight. Solvents were then removed by vacuum evaporation, and the residue was purified by reverse phase C-18 HPLC using the gradient 5-50% acetonitrile (containing 0.05% TFA) in water (containing 0.05% TFA). The desired DOTA-PEG 4-DOTA·$Lu^{3+}$ (19.6 mg, 61%) mono-complex was isolated as a white foam upon lyophilization of product-containing fractions. $^1H$ NMR, $D_2O$: 7.30-7.15 (m, 8H), 3.75-2.90 (m, 58H), 2.82-2.36 (m, 11H), 2.18-2.14 (m, 1H). The latter multiplet contains some water peaks as well.

LCMS: $R_f$=4.51 minutes on a 8 minutes' HPLC run. MS calculated for $C_{58}H_{87}LuN_{12}O_{20}S_2$, $[M+1]^+$=1511.51, $[M+1]^{2+}$=755.75, Found: 756.25. In negative mode, $[M-1]^{2-}$= 754.82, found: 754.75.

Example 4: Synthesis of DOTA·$Lu^{3+}$-PEG 4-NODAGA

DOTA·$Lu^{3+}$-PEG 4-NODAGA

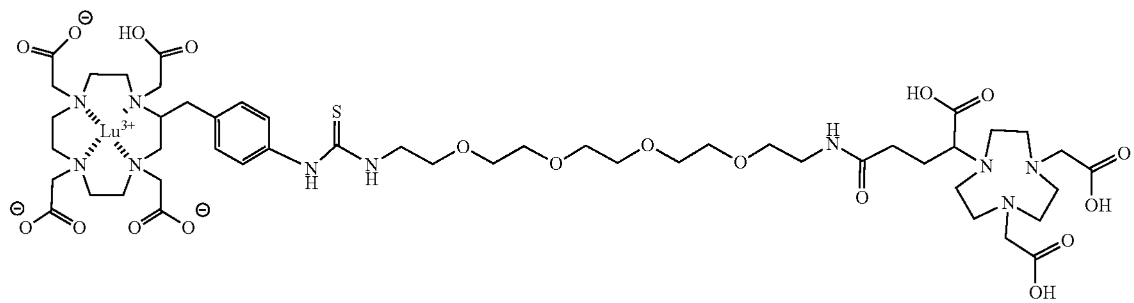

At room temperature (about 21° C.), p-SCN-Bn-DOTA·$Lu^{3+}$ major isomer complex (20 mg, 27.6 μmol) and $NH_2$-PEG 4-NODAGA (17 mg, 28.6 μmol) were dissolved in anhydrous DMF (0.8 mL) before treatment with $Et_3N$ (20 μL). The resulting mixture was stirred at room temperature for an overnight period. Solvents were then removed by vacuum evaporation, and the colorless residue was purified by reverse phase C-18 HPLC, using the gradient 5-40% acetonitrile (containing 0.05% TFA) in water (containing 0.05% TFA). DOTA·$Lu^{3+}$-PEG 4-NODAGA (15.1 mg, 41%) was obtained as a white foam after lyophilization of the appropriate fractions.

$^1H$ NMR, $D_2O$: 7.15-7.25 (m, 4H), 3.94-3.91 (m, 1H), 3.89-3.51 (m, 26H), 3.45-2.81 (m, 24H), 2.5-2.35 (m, 12H), 2.20-2.18 (m, 1H), 2.07-2.03 (m, 1H), 1.97-1.94 (m, 1H). Two close isomers are observed in LCMS with the ratios: 18% and 82%. The minor is at 3.02 minutes $R_f$ and the major at 3.08 minutes within the 8 minutes' run. MS calculated for $C_{49}H_{77}LuN_{10}O_{19}S$=1316.45. $[M+1]^+$=1317.46, $[M+1]^{2+}$= 658.73. Found: 659.35.

Alternatively, DOTA-$Lu^{3+}$-PEG4-$NH_2$ TFA may be reacted with the NHS ester of NODAGA ("NODAGA-NHS," CAS Number 1407166-70-4, illustrated in Scheme 4) and excess base in DMF, and after completion of the reaction (e.g., as indicated by HPLC) utilizing reverse phase C-18 HPLC purification and lyophilization to provide DOTA·$Lu^{3+}$-PEG 4-NODAGA.

Scheme 4.

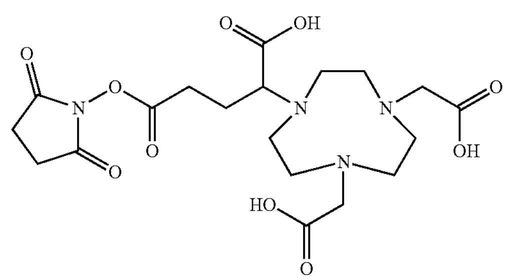

NODAGA-NHS

Notably, utilizing protocols similar to either of the above-described procedures provides for other compounds of the present technology. For example, HOPO-NHS (illustrated in Scheme 5) may be reacted with DOTA-$Lu^{3+}$-PEG4-$NH_2$ TFA and excess base in DMF, and after completion of the reaction (e.g., as indicated by HPLC) utilizing reverse phase C-18 HPLC purification and lyophilization to provide DOTA-$Lu^{3+}$-PEG4-HOPO (as also illustrated in Scheme 5).

Scheme 5. HOPO-NHS and DOTA-Lu$^{3+}$-PEG4-HOPO
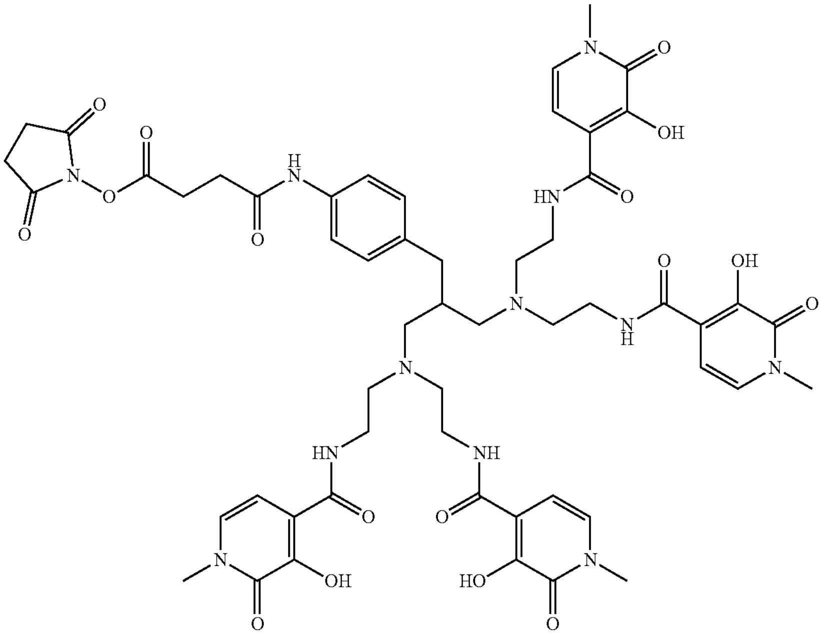
HOPO-NHS
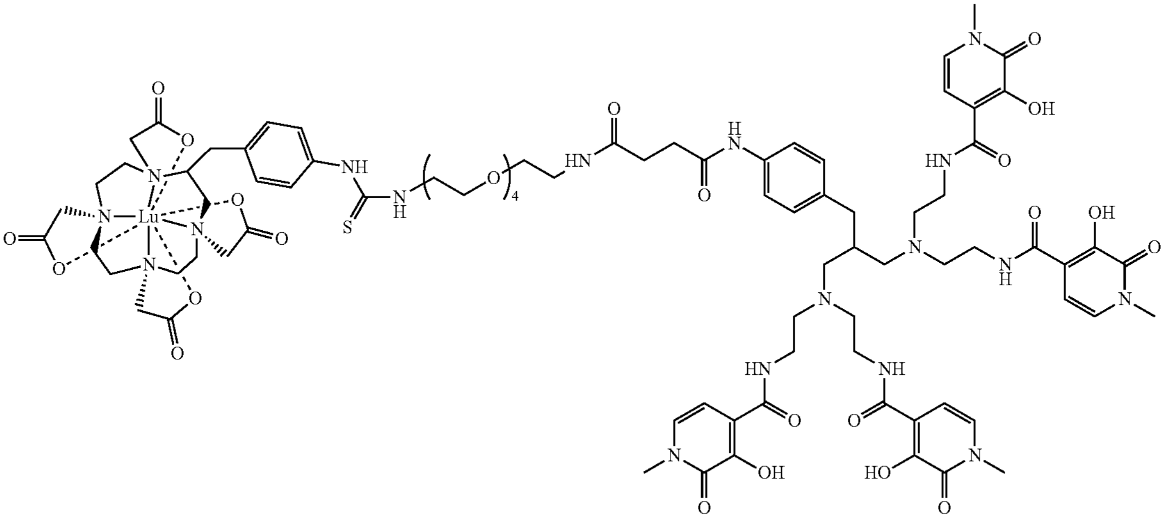
DOTA-Lu$^{3+}$-PEG4-HOPO Example 5: Synthesis of TCMC-PEG$_4$-$^{nat}$Lu-DOTABn residue was dried under high vacuum (2 h) and submitted directly in the next step without further purification.

Scheme 6.

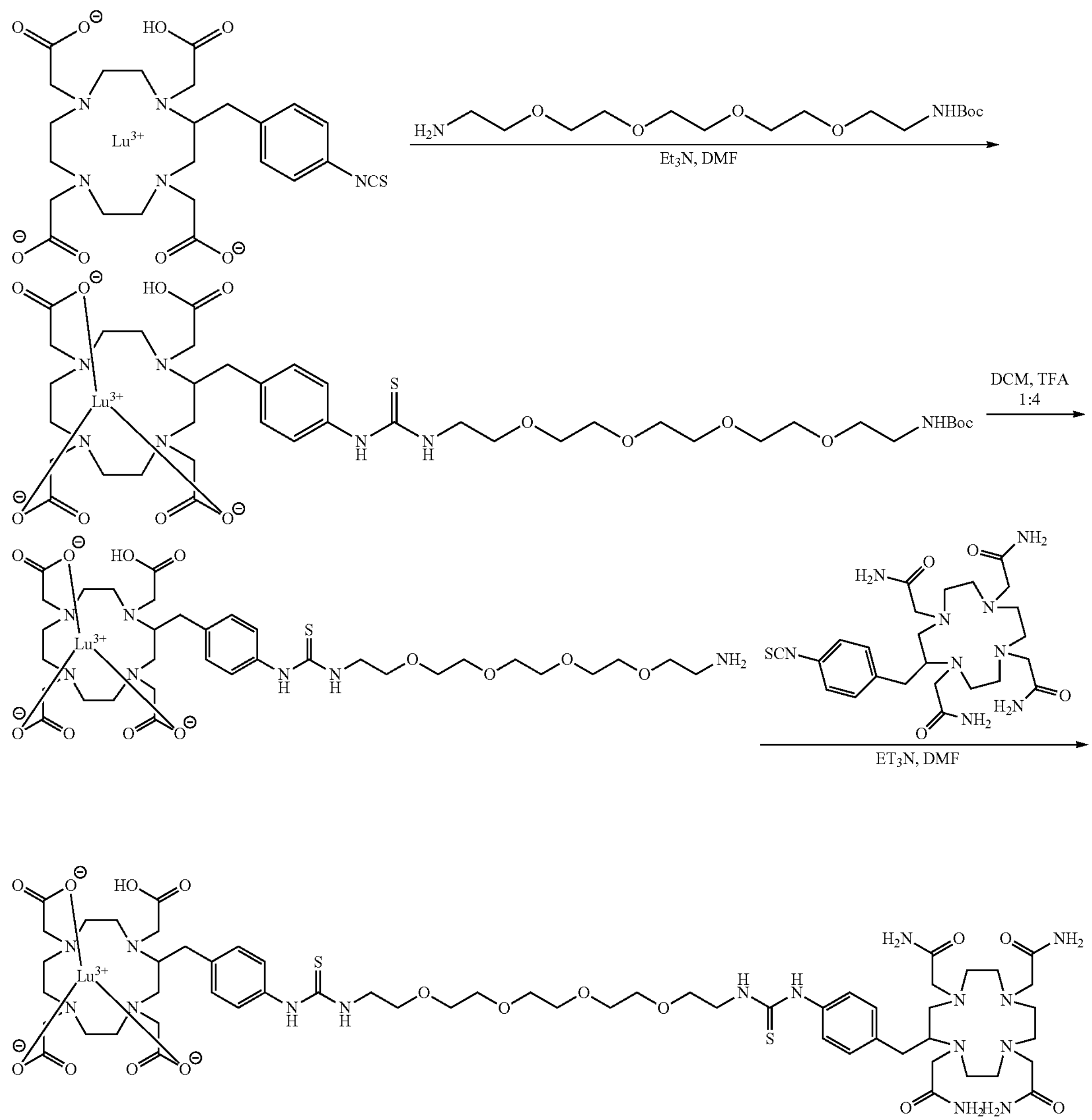

DOTA-Lu$^{3+}$-PEG4-NHBoc:

To DOTA-Lu$^{3+}$-SCN (25.0 mg, 34.6 μmol) and BocNH-PEG4-$NH_2$ (13.9 mg, 41.3 μmol) in DMF (0.8 mL) was added $Et_3N$ (29 μL). The mixture was stirred at RT for 5 h. Solvents were removed under reduced pressure. The residue was purified by preparative reverse phase C-18 HPLC using a gradient of 20:80 MeCN:$H_2O$ to 40:60 MeCN:$H_2O$ (both containing 0.05% TFA) over 10 min, the product was obtained after lyophilization (14.0 mg, 38%).

DOTA-Lu$^{3+}$-PEG4-$NH_2$:

DOTA-Lu3+-PEG4-NHBoc (14.0 mg, 13.2 μmol) in TFA:DCM (4:1, V:V) was stirred at RT for 40 min, the solvents were then removed under reduced pressure. The DOTA-Lu$^{3+}$-PEG4-TCMC The residue above was dissolved in DMF (0.8 mL), then TCMC-DOTA (10 mg, 18.3 μmol) and $Et_3N$ (40 μL) were added to the mixture. The reaction was stirred at ambient temperature overnight. The volatiles were removed under reduced pressure, and the residue was purified by preparative C-18 reverse phase HPLC using the gradient of 5:95 MeCN:$H_2O$ to 40:60 MeCN:$H_2O$ (both with 0.05% TFA) over 10 min. The product was obtained after lyophilization (16.19 mg, 81%). $^1$HNMR (500 MHz, $D_2O$): δ=7.25-7.18 (m, 8H), 3.82-3.2 (m, 40H), 3.10-2.95 (m, 2H), 2.83-2.38 (m, 28H). MS: calculated: 1507.6 $[M+H]^+$; found: 1507.5.

Example 6: Radiosynthesis of Compounds of Present Technology

Radiochemistry was performed in appropriately shielded chemical fume hoods equipped with electronic flow monitoring and sliding leaded glass windows. A CRC-55tR dose calibrator was used to measure radioactivity using manufacturer recommended calibration settings (Capintec Inc., Florham Park, NJ). Buffers and water used for radiochemical synthesis were treated with 5% w/v Chelex ion exchange resin (BT Chelex 100 Resin, Bio-Rad Inc., Hercules, CA) to remove adventitious heavy metals. Plasticware (pipet tips and microcentrifuge tubes) were tracemetal grade/RNA grade. RadioHPLC was performed on a Shimadzu Prominence HPLC system comprised of an LC-20AB dual pump module, DGU-20A3R degasser, SIL-20ACHT autosampler, SPD-20A UV-Vis detector and a Bioscan Flow-Count B-FC-1000 with PMT/NaI radioactivity detector in-line. Separations were run on an analytical 4.6×250 mm Gemini-NX C18 or Fusion RP C18 HPLC column (Phenomenex, Inc. Torrance, CA). Unless otherwise noted, HPLC conditions were: solvent A—10 mM pH 5 $NH_4OAc$, B—$CH_3CN$, 1.0 mL/min flow rate, $\lambda$=254 nm, injection volume 10-50 μL, gradient: 0% B to 40% B over 10 min. Samples of free radiometals, reaction mixtures and purified products were diluted 1:5 in 5 mM DTPA prior to analysis.

Radiosynthesis of [$^{203}$Pb]TCMC-PEG$_4$-LuDOTA

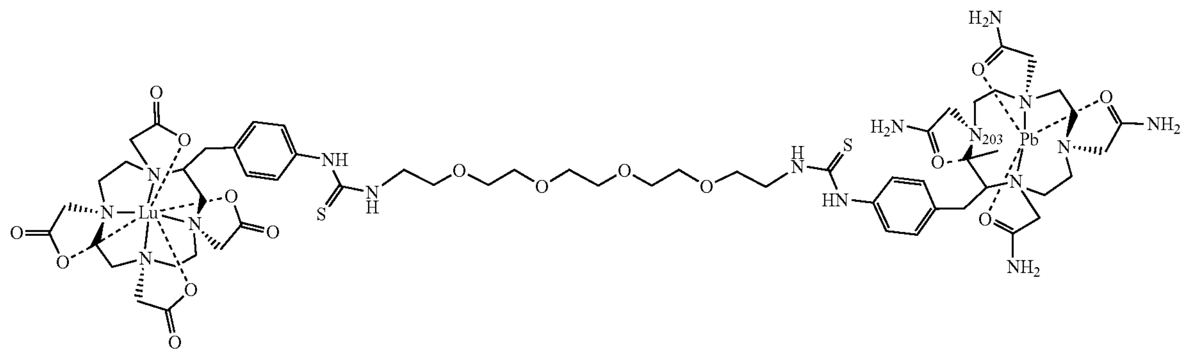

$^{203}PbCl_2$ (39.2 MBq/1.06 mCi) in 15 μL of 0.5M HCl (Lantheus Medical Imaging, Billerica MA) was transferred to a metal-free 1.5 mL microcentrifuge tube and diluted with 200 μL of chelexed aqueous 0.5M $NH_4OAc$ (pH 5.3) and mixed gently. To this was added 10 μL of 1 mM TCMC-PEG$_4$-LuDOTA (10 nmol) and mixed gently and placed in a heat block set to 40° C. After 30 minutes, the reaction was cooled briefly, then the entirety was gravity loaded on a 30 mg Strata-X SPE cartridge (Phenomenex, Torrance CA), which had been equilibrated with 1 mL of ethanol and 1 mL of water. Water (100 μL) was used to rinse the reaction tube and passed through the cartridge. The column was washed slowly dropwise with 200 μL of water, the column purged gently with nitrogen gas, then the product was slowly eluted dropwise with 200 μL of ethanol into a clean 2 mL microfuge tube and diluted to 2.0 mL with normal saline (Hospira, Lake Forest, IL) and sterile filtered to obtain [$^{203}$Pb]TCMC-PEG$_4$-LuDOTABn (36.1 MBq (975 μCi), 92% yield, $A_M$=3.9 MBq/nmol (106 μCi/nmol)). RadioHPLC confirmed that no free radiometal remained (98.1% radiochemical purity; major isomer $t_R$=10.8 min).

Radiosynthesis of [$^{89}$Zr]DFO-PEG$_4$-LuDOTA

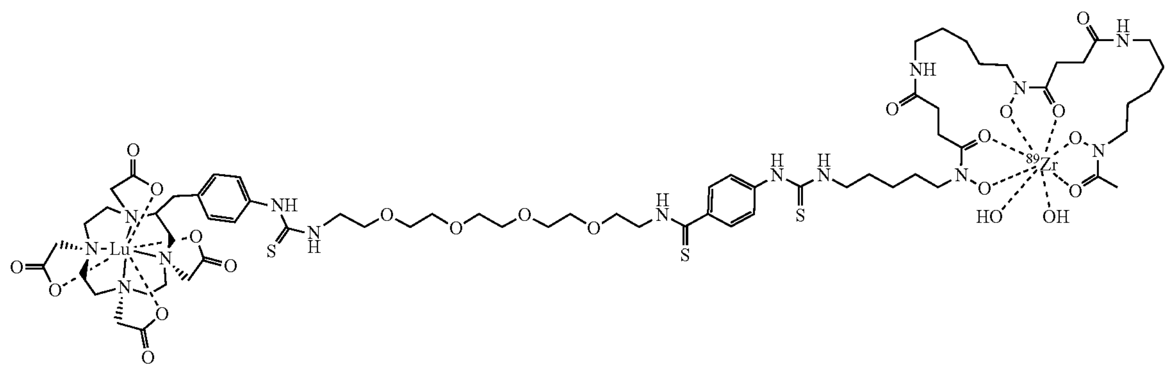

[$^{89}$Zr]ZrOxalate$_2$ (67.7 MBq/1.83 mCi) in 50 μL of 1.0M oxalic acid (Cyclotron Core Facility MSKCC) was transferred to a metal-free 1.5 mL microcentrifuge tube and neutralized with an equimolar amount of metal-free 1.0M $Na_2CO_3$~45 μL, then diluted with 400 μL of metal-free 0.5M HEPES buffer (pH 7.5) and mixed. To this was added DFO-PEG$_4$-LuDOTA (9.2 nmol, 9.2 μL of 1.0 mM solution in water), mixed and placed in a heat block at 40° C. After 60 minutes, the entirety was gravity loaded on a 30 mg Strata-X SPE cartridge (Phenomenex, Torrance CA), which had been equilibrated with 1 mL of ethanol and 1 mL of water. Water (100 μL) was used to rinse the reaction tube and passed through the cartridge. The SPE cartridge was washed with 200 μL of water, gently blown dry with nitrogen gas, then the product was slowly eluted dropwise with 200 μL of ethanol into a clean 2 mL microfuge tube. The eluent was diluted into 2 mL with normal saline (Hospira, Lake Forest, IL) and sterile filtered to obtain 44 MBq (1.2 mCi; 66% yield, $A_M$=7.4 MBq (0.2 mCi)/nmol) of [$^{89}$Zr]DFO-PEG$_4$-LuDOTA. This stock was used to prepare the doses for PET imaging and biodistribution (3.7 MBq/100 μCi; 0.5 nmol). RadioHPLC (solvent A: 0.1% TFA, B: $CH_3CN$) of crude and purified material confirmed that no detectable free radiometal remained (major isomer $t_R$=10.7 min, 99+% conversion).

Radiosynthesis of [$^{177}$Lu]DOTABn-PEG$_4$-LuDOTA

[$^{177}$Lu]LuCl$_3$ (38 MBq/1.03 mCi) in 19 μL of 0.05M HCl (NIDC/MURR; Missouri University Research Reactor, Columbia, MO) was transferred to a metal-free 1.5 mL microcentrifuge tube and diluted with 100 μL of metal-free 0.5M $NH_4OAc$ (pH 5.3) and mixed gently. To this was added DOTABn-PEG$_4$-LuDOTABn (5 nmol, 5 μL of 1 mM solution in water), and mixed gently and placed in a heat block at 80° C. for 60 minutes. After cooling for 5 minutes, the entirety was gravity loaded on a 30 mg Strata-X SPE cartridge (Phenomenex, Torrance CA), which had been equilibrated with 1 mL of ethanol and 1 mL of water. Water (100 μL) was used to rinse the reaction tube and passed through the cartridge. The column was washed slowly dropwise with 200 μL of water, gently blown dry with nitrogen gas. The product was slowly eluted dropwise with 200 μL of ethanol into a clean 2 mL microfuge tube and diluted to 2.0 mL with normal saline (Hospira, Lake Forest, IL) and sterile filtered to obtain [$^{177}$Lu]DOTABn-PEG$_4$-$^{nat}$LuDOTA (33.7 MBq (0.91 mCi), 88% yield, $A_M$=7.4 MBq/nmol (0.2 mCi/nmol)). RadioHPLC of crude and purified material confirmed that no free radiometal remained (99+% radiochemical purity; major isomer $t_R$=9.3 min).

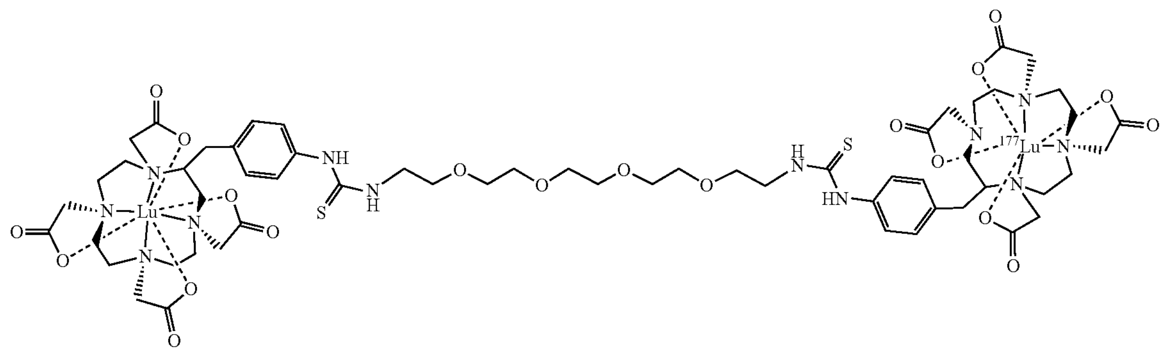

Radiosynthesis of [$^{86}$Y]DOTABn-PEG$_4$-LuDOTA

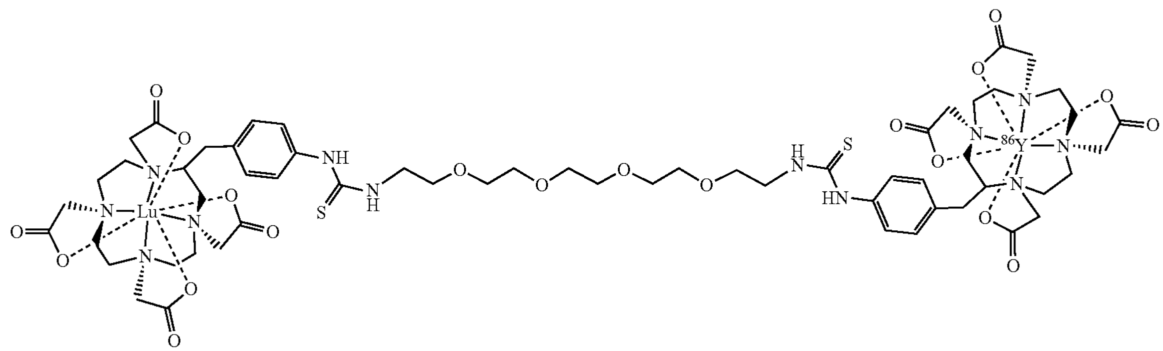

[$^{86}$Y]YCl$_3$ (4.7 MBq/126 Ci) in 5 L of 0.04M HCl (MIDACC CRF; Cyclotron Radiochemistry Facility MD Anderson Cancer Center, Houston, TX) was transferred to a metal-free 0.5 mL microcentrifuge tube and diluted with 50 μL of metal-free 0.5M $NH_4OAc$ (pH 5.3) and mixed gently. To this was added DOTABn-PEG$_4$-LuDOTABn (2 nmol, 2 μL of 1 mM solution in water), and mixed gently and placed in a heat block at 80° C. for 60 minutes. After cooling for 5 minutes, the entirety was gravity loaded on a 30 mg Strata-X SPE cartridge (Phenomenex, Torrance CA), which had been equilibrated with 1 mL of ethanol and 1 mL of water. Water (100 μL) was used to rinse the reaction tube and passed through the cartridge. The column was washed slowly dropwise with 200 μL of water, gently blown dry with nitrogen gas. The product was slowly eluted dropwise with 200 μL of ethanol into a clean 2 mL microfuge tube and diluted to 2.0 mL with normal saline (Hospira, Lake Forest, IL) and sterile filtered to obtain [$^{86}$Y]DOTABn-PEG$_4$-$^{nat}$-LuDOTA (1.38 MBq (37.2 μCi), 29% yield, $A_M$=2.3 MBq/nmol (63 μCi/nmol)). RadioHPLC confirmed that no free radiometal remained (99+% radiochemical purity; major isomer $t_R$=9.15 min).

Radiosynthesis of [$^{68}$Ga]NODAGA-PEG$_4$-LuDOTA

[$^{68}$Ga]GaCl$_3$ (175 MBq/4.7 mCi) in 1 mL 0.1M HCl was eluted from a GalliaPharm $^{68}$Ge/$^{68}$Ga generator (Eckert & Ziegler Radiopharma GmbH, Berlin, Germany) was transferred to a metal-free 2 mL microcentrifuge tube and diluted with 500 μL of chelexed aqueous 0.5M $NH_4OAc$ (pH 5.3) and mixed gently. To this was added NODAGA-PEG$_4$-LuDOTA (2 nmol in 20 μL water) and mixed gently. The tube was placed in a heat block at 80° C. for 15 minutes. After cooling for 5 minutes, the entirety was gravity loaded on a 30 mg Strata-X SPE cartridge (Phenomenex, Torrance CA), which had been equilibrated with 1 mL of ethanol and 1 mL of water. Water (100 μL) was used to rinse the reaction tube and passed through the cartridge. The column was washed with 200 μL of water, blown dry with nitrogen gas, then the product was slowly eluted dropwise with 200 μL of ethanol into a clean 1.5 mL microfuge tube. The volume of eluent was reduced under dry nitrogen gas flow to approximately 50 μL, diluted into 2 mL of normal saline (Hospira, Lake Forest, IL) and sterile filtered to obtain 141 MBq (3.8 mCi; 81% yield, $A_M$=65 MBq/nmol (1.8 mCi/nmol)) of [$^{68}$Ga]NODAGA-PEG$_4$-LuDOTA. This stock was used to prepare the doses for PET imaging (9.6 MBq/260 μCi; 0.15 nmol) and was diluted further in sterile saline for biodistribution doses (6.5 MBq/175 μCi; 0.1 nmol). RadioHPLC of crude and purified material confirmed that no free radiometal remained (major isomer $t_R$=8.1 min, 99+% conversion).

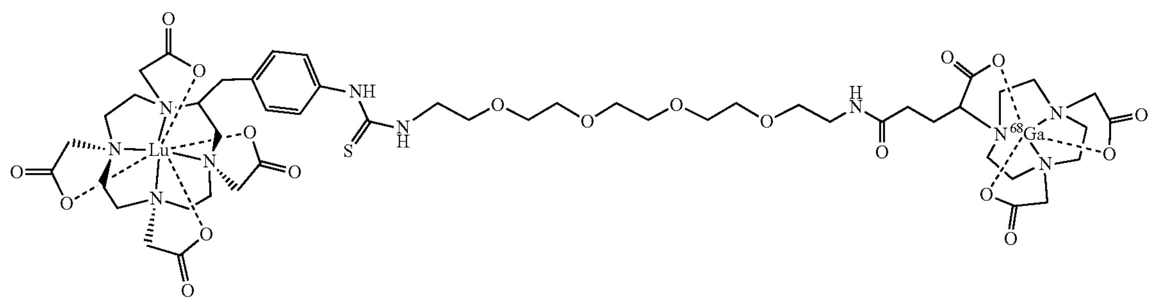

Radiosynthesis of [$^{64}$Cu]NODAGA-PEG$_4$-LuDOTA

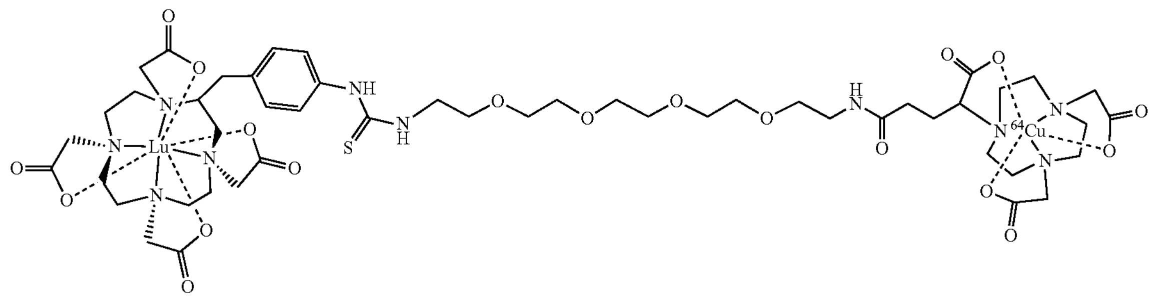

[$^{64}$Cu]$CuCl_2$ (38.1 MBq/1.03 mCi) in 4 μL (Washington University St. Louis) was transferred to a metal-free 1.5 mL microcentrifuge tube and diluted with 30 μL of chelexed aqueous 0.5M $NH_4OAc$ (pH 5.3) and mixed gently. To this was added NODAGA-PEG$_4$-LuDOTA (3 nmol) in 30 μL buffer, and mixed gently. After 5 minutes, the entirety was gravity loaded on a 30 mg Strata-X SPE cartridge (Phenomenex, Torrance CA), which had been equilibrated with 1 mL of ethanol and 1 mL of water. Water (100 μL) was used to rinse the reaction tube and passed through the cartridge. The column was washed slowly dropwise with 200 μL of water, gently blown dry with nitrogen gas, then the product was slowly eluted dropwise with 200 μL of ethanol into a clean 1.5 mL microfuge tube. The volume of eluent was reduced under dry nitrogen gas flow to approximately 50 μL, diluted into normal saline (Hospira, Lake Forest, IL) and sterile filtered to obtain 26.1 MBq (0.71 mCi; 68% yield) of [$^{64}$Cu]NODAGA-PEG$_4$-LuDOTA. This stock was used to prepare the doses for PET imaging (11 MBq/300 μCi; 1 nmol) and was diluted further in sterile saline for biodistribution doses (1.9 MBq/51 μCi; 0.15 nmol). RadioHPLC of crude and purified material confirmed that no free radiometal remained (99+% radiochemical purity; $A_M$=12.7 MBq/nmol).

Example 7: Stability of Radionuclide-Containing Compounds of the Present Technology Stability of [$^{203}$Pb]TCMC-PEG$_4$-LuDOTA in Human Serum: [$^{203}$Pb]TCMC-PEG$_4$-LuDOTA (88 μCi in 25 μL PBS) was gently mixed with 1 mL of human serum (Equitech-Bio) and incubated at 37° C. At three time points (1.5, 3 and 24 hours) 100 μL samples were withdrawn and placed in a microfuge tube. Each was treated with 200 μL of 3:1 acetonitrile:methanol to precipitate protein, then centrifuged for 10 minutes at 10,000×g at 4° C. Then, 200 μL of the supernatant was removed and the volume reduced under nitrogen gas flow for 20 minutes. The concentrate was diluted with 100 μL of 1 mM EDTA to chelate free $^{203}$Pb then 50 μL of each sample was analyzed by radioHPLC. Calibration of the radioHPLC by independently produced [$^{203}$Pb]EDTA found a retention time of 2.2 minutes for [$^{203}$Pb]EDTA under the radioHPLC conditions. However, none of the three samples provided detectable levels of [$^{203}$Pb]EDTA, thus evidencing no degradation of [$^{203}$Pb]TCMC-PEG$_4$-LuDOTA when incubated in human serum at 37° C. for 24 hours.

Plasma Clearance of [$^{203}$Pb]TCMC-PEG$_4$-LuDOTA: Five female nude athymic mice (20-25 g) were injected intravenously in the tail vein with 95±2.4 μCi of [$^{203}$Pb]PbTCMC-PEG$_4$-LuDOTA in 200 μL of sterile saline. At 5, 15, 30, 60 and 90 minutes post injection, the animals were euthanized by $CO_2$ asphyxiation and immediately 0.5-1.0 mL of blood collected by intracardiac puncture and transferred into EDTA anticoagulant containing tubes on ice. The samples were centrifuged (10,000×g at 4° C. for 10 minutes). The radioactivity in a 100 μL samples of plasma were counted on a PerkinElmer Wizard3 gamma counter using a 150-500 keV energy window.

Raw data for mouse plasma clearance study is provided below:

| | Syringe | residual | Injected activity | CPM (150-500 keV) 100 μL plasma | cal fact calc μCi | 980050 elapsed time D/C μCi | plasma 0.1 mL = 0.1 g (manually % ID/g |
|---|---|---|---|---|---|---|---|
| M1 5 min | 95 | 1.3 | 93.7 | 983555 | 1.003576 | 1.35 | 14.40768 |
| M2 15 min | 97 | 1.39 | 95.61 | 719633 | 0.734282 | 0.985 | 10.30227 |
| M3 30 min | 97.7 | 1.64 | 96.06 | 250693 | 0.255796 | 0.343 | 3.570685 |
| M4 60 min | 97.9 | 3.16 | 94.74 | 25984 | 0.026513 | 0.0356 | 0.375765 |
| M5 90 min | 96.8 | 2.17 | 94.63 | 7597 | 0.007752 | 0.0104 | 0.109902 |

| | uCi | Mbq |
|---|---|---|
| | 94.9 | 3.51 |
| Hi | 96.06 | 3.55 |
| Lo | 93.7 | 3.47 |
| Range | 2.4 | 0.09 |

Using the calibration factor for Pb-203 on the gamma counter window (150-500 keV), the radioactivity in each sample was calculated, decay corrected back to the time of injection, and then normalized by the injected dose in each animal. The percent injected dose per gram (% ID/g) at each time point was calculated according to the following formula:

$$\frac{\frac{DC \text{ Radioactivity in plasma}}{\text{Infected Radioactivity}} \times 100\%}{0.1 \text{ g plasma mass}}$$

Figure 1B:
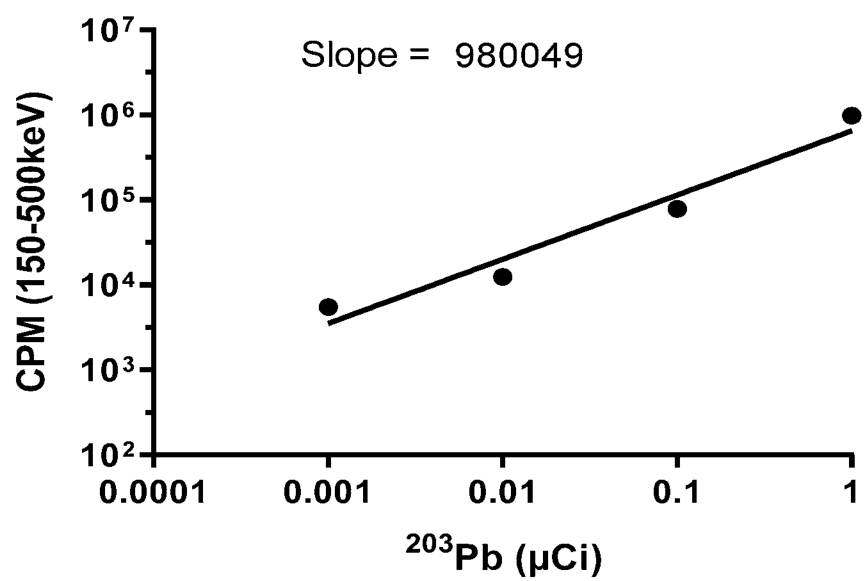
FIG. 1B shows the calibration curve for Pb-203 on the gamma counter window (150-500 keV).

The percent injected dose per gram (% ID/g) at each time point was calculated and plotted over time, as illustrated in FIGS. 1A-1B. This data illustrates that the vast majority (>97%) of [$^{203}$Pb]PbTCMC-PEG$_4$-LuDOTA clears the plasma after 1 hour.

Example 8: In Vivo Biodistribution Properties of the Compounds of the Present Technology DOTA-PRIT using the positron-emitting (PET) isotope gallium-68 ($^{68}$Ga) could accelerate the development of companion PET diagnostics, but the antibody affinity for $^{68}$Ga-benzyl-DOTA is low (Orcutt K D, et al. (2012) *Mol Cancer Ther,* 11(6): 1365-72).

[$^{89}$Zr]DFO-PEG$_4$-LuDOTA. Female athymic nude mice bearing s.c. GPA33-expressing SW1222 xenografts were administered 0.25 mg (1.19 nmol) of HuA33-C825 (from Cheal, et al. *Eur J Nucl Med Mol Imaging.* 2016 May; 43(5):925-937) at t=−28 h, followed with 16-N-acetylgalactosamine-DOTA(Y) clearing agent; 25 μg (2.76 nmol) at t=−4 h and [$^{89}$Zr]DFO-PEG$_4$-LuDOTA at t=0 h. Tumor-free controls were administered [$^{89}$Zr]DFO-PEG$_4$-LuDOTA at t=0 h.

The mice undergoing PRIT were sacrificed 4 hours after injection of [$^{89}$Zr]DFO-PEG$_4$-LuDOTA, while those given only [$^{89}$Zr]DFO-PEG$_4$-LuDOTA were sacrificed 4 hours after injection for biodistribution assessment. FIG. 5 shows representative PET maximum intensity projection images of two different mice that underwent PRIT with [$^{89}$Zr]DFO-PEG$_4$-LuDOTA. Images were obtained at 4 hours post-injection of [$^{89}$Zr]DFO-PEG$_4$-LuDOTA.

As shown in FIG. 2, animals undergoing PRIT with BsAb huA33-C825 and [$^{89}$Zr]DFO-PEG$_4$-LuDOTA, the blood, tumor, and kidney uptakes at 4 hours after injection were 0.92±0.12% ID/g, 9.30±2.88% ID/g, and 6.45±0.85% ID/g, respectively, corresponding to tumor-to-organ activity ratios of about 10.1±2.0 and 1.4±0.3 for blood and kidney, respectively. The blood uptake of [$^{89}$Zr]DFO-PEG$_4$-LuDOTA alone was 0.09±0.02% IA/g at 4 hours after injection, indicating negligible normal tissue uptake. See FIG. 3. The blood half-life of [$^{89}$Zr]DFO-PEG$_4$-LuDOTA was determined to be 11.88 minutes ($R^2$=0.9701). The whole-body half-life of [$^{89}$Zr]DFO-PEG$_4$-LuDOTA was determined to be 59.76 minutes ($R^2$=0.8914). See FIG. 4.

[$^{68}$Ga]NODAGA-PEG$_4$-LuDOTA. DOTA·Lu$^{3+}$-PEG 4-NODAGA was radiolabeled with $^{68}$Ga, and in vitro and in vivo studies were conducted to characterize the radiostability and determine if pretargeting of [$^{68}$Ga]NODAGA-PEG$_4$-LuDOTA hapten (also referred to herein as "$^{68}$Ga-NODAGA-proteus-DOTA") to tumor was feasible. Athymic nude mice bearing the GPA33-expressing human colorectal cancer SW1222 xenograft was used as a model for anti-GPA33 Benzyl-DOTA-PRIT.

DOTA·Lu$^{3+}$-PEG 4-NODAGA was synthesized from amine-PEG$_4$-NODAGA and the non-radioactive lutetium-175-complex of 2-(4-isothiocyanatobenzyl)-DOTA. Radiolabeling of DOTA·Lu$^{3+}$-PEG 4-NODAGA was accomplished by typically mixing ~185 MBq of generator-eluted [$^{68}$Ga]GaCl$_3$ to 2 nmol of DOTA·Lu$^{3+}$-PEG 4-NODAGA in 0.5 M sodium acetate pH 5.3 and incubating for 15 minutes at 80° C. (molar activity at end of synthesis: 70 MBq/nmol; radiochemical yield: <98%; radiochemical purity: 98%).

Figure 7:
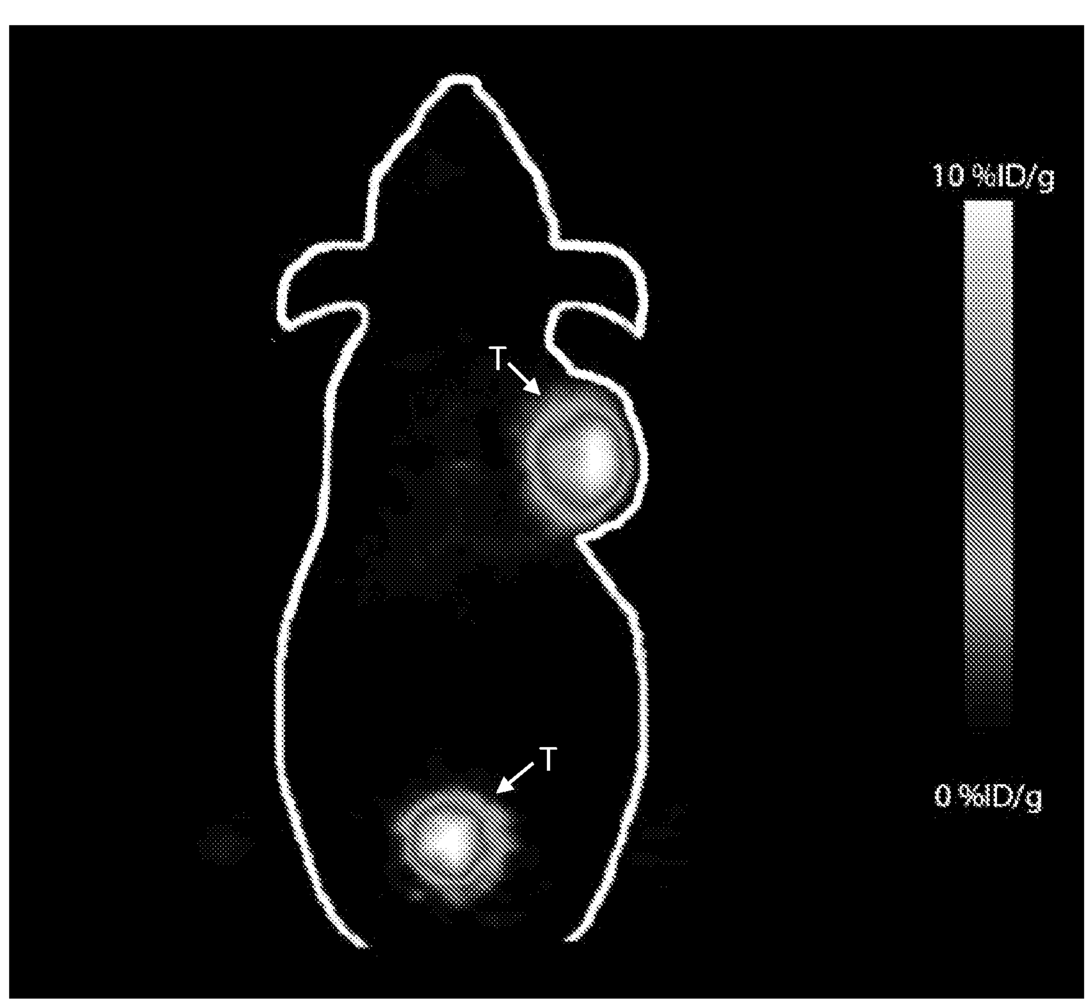
FIG. 7 shows a representative PET image (coronal) of a mouse that underwent PRIT with [$^{68}$Ga]NODAGA-PEG$_4$-LuDOTA (130 pmol/6.0 MBq). Images were obtained at obtained at 1 hour post-injection of [$^{68}$Ga]NODAGA-PEG$_4$-LuDOTA. Tumor is clearly visible in the shoulder ("T").

Female athymic nude mice bearing s.c. GPA33-expressing SW1222 xenografts were administered 0.25 mg (1.19 nmol) of HuA33-C825 (from Cheal, et al. *Eur J Nucl Med Mol Imaging.* 2016 May; 43(5):925-937) at t=−28 h, followed with 16-N-acetylgalactosamine-DOTA(Y); 25 μg (2.76 nmol) at t=−4 h and [$^{68}$Ga]DO3A-PEG$_4$-LuDOTA or [[$^{68}$Ga]NODAGA-PEG$_4$-LuDOTA at t=0 h. FIG. 7 shows representative PET image (coronal) of a mouse that underwent PRIT with [$^{68}$Ga]NODAGA-PEG$_4$-LuDOTA. Images were obtained at obtained at 1 hour post-injection of [$^{68}$Ga] NODAGA-PEG$_4$-LuDOTA. Tumor is clearly visible in the shoulder region.

As shown in FIG. 6, animals undergoing PRIT with BsAb huA33-C825 and [$^{68}$Ga]NODAGA-PEG$_4$-LuDOTA, the blood, tumor, and kidney uptakes at 1 hour after injection were 1.29±0.57% ID/g, 16.44±4.75% ID/g, and 1.23±0.25% ID/g, respectively, corresponding to tumor-to-organ activity ratios of about 12.7±3.9 and 13.4±2.7 for blood and kidney, respectively. In contrast, animals undergoing PRIT with BsAb huA33-C825 and [$^{68}$Ga]DO3A-PEG$_4$-LuDOTA exhibited tumor-to-organ activity ratios of about 4.6±2.1 and 7.8±3.5 for blood and kidney, respectively. Accordingly, the tumor-to-organ activity ratios for blood and kidney were at least 1.7 to 2.7 fold higher with [$^{68}$Ga]NODAGA-PEG$_4$-LuDOTA compared with [$^{68}$Ga]DO3A-PEG$_4$-LuDOTA.

Figure 9:
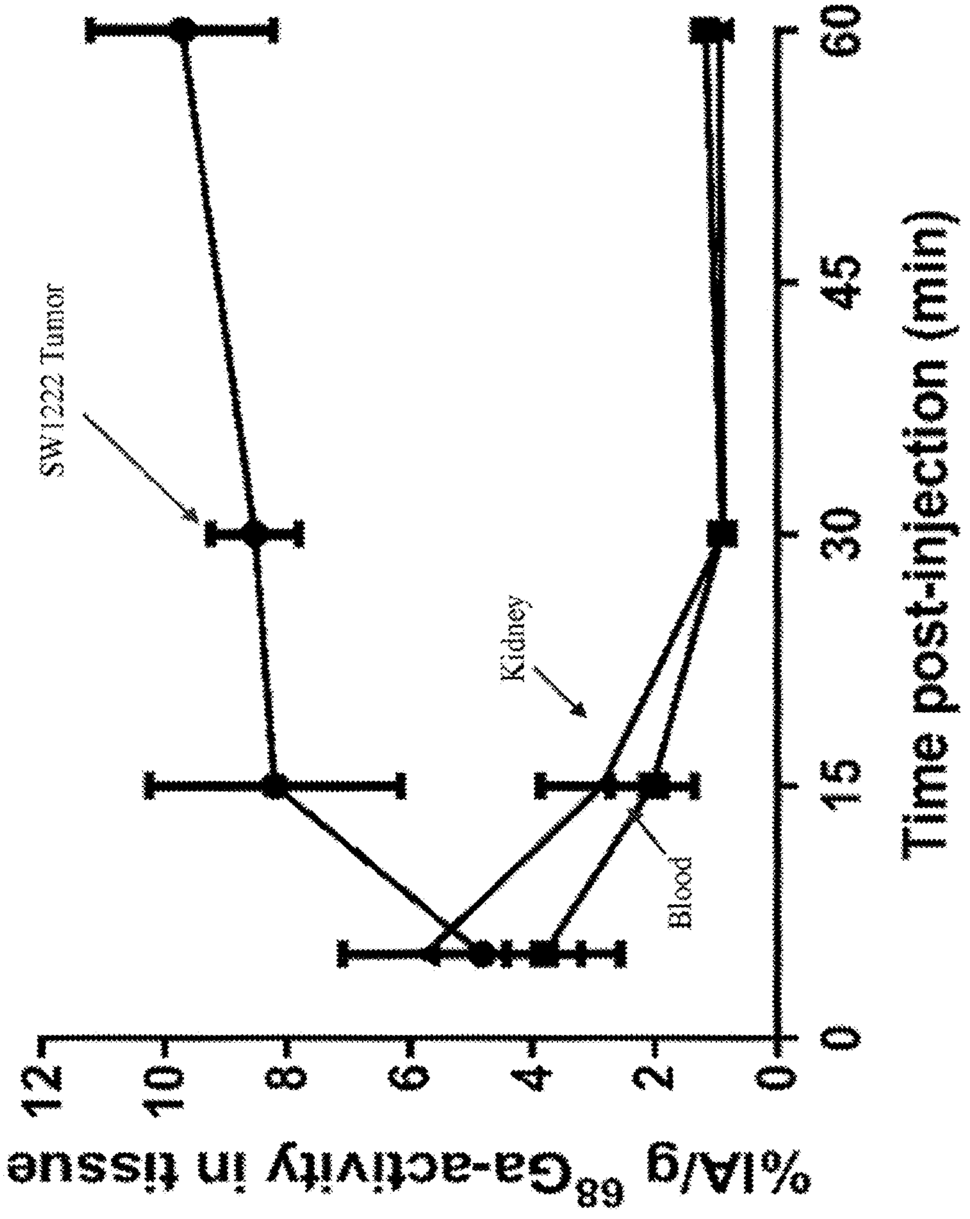
FIG. 9 shows $^{68}$Ga activity time curves for tumor, blood, and kidney based on serial ex vivo biodistribution data collected at 5, 15, 30, and 60 minutes post-injection of pretargeted [$^{68}$Ga]NODAGA-PEG$_4$-LuDOTA (FIG. 8). Data in graph is presented as average±standard deviation.

An in vitro plasma stability study with mouse serum at 37° C. revealed no significant demetallation over one hour and minimal serum-protein binding of radioactivity. Female athymic nude mice bearing s.c. GPA33-expressing SW1222 xenografts were administered 0.25 mg (1.19 nmol) of HuA33-C825 (from Cheal, et al. *Eur J Nucl Med Mol Imaging.* 2016 May; 43(5):925-937) at t=−28 h, followed with 16-N-acetylgalactosamine-DOTA(Y); 25 μg (2.76 nmol) at t=−4 h and [[$^{68}$Ga]NODAGA-PEG$_4$-LuDOTA at t=0 h. For calculation of mol, doses drawn up were 132 μCi for [$^{68}$Ga]NODAGA-PEG$_4$-LuDOTA. Mice were administered 71 μCi [2.62 MBq] (75 μmol). As shown in FIG. 8, serial biodistribution experiments performed at 5, 15, 30, and 60 min post-injection (p.i.) of pretargeted [$^{68}$Ga] NODAGA-PEG$_4$-LuDOTA (4 MBq, 67 μmol) revealed rapid tumor targeting combined with renal clearance. At 60 min p.i., the tumor uptake reached ~10 percentage of injected $^{68}$Ga-dose per gram (% ID/g) with minimal normal tissue accumulation including blood and kidney (both ~1% ID/g). Maximum tumor uptake (8-10% IA/g) was obtained within 15 minutes post-injection, and maximum tumor-to-blood and tumor-to-kidney ratios (both ~10:1) were obtained within 30 minutes post-injection. See FIG. 9.

Figure 11:
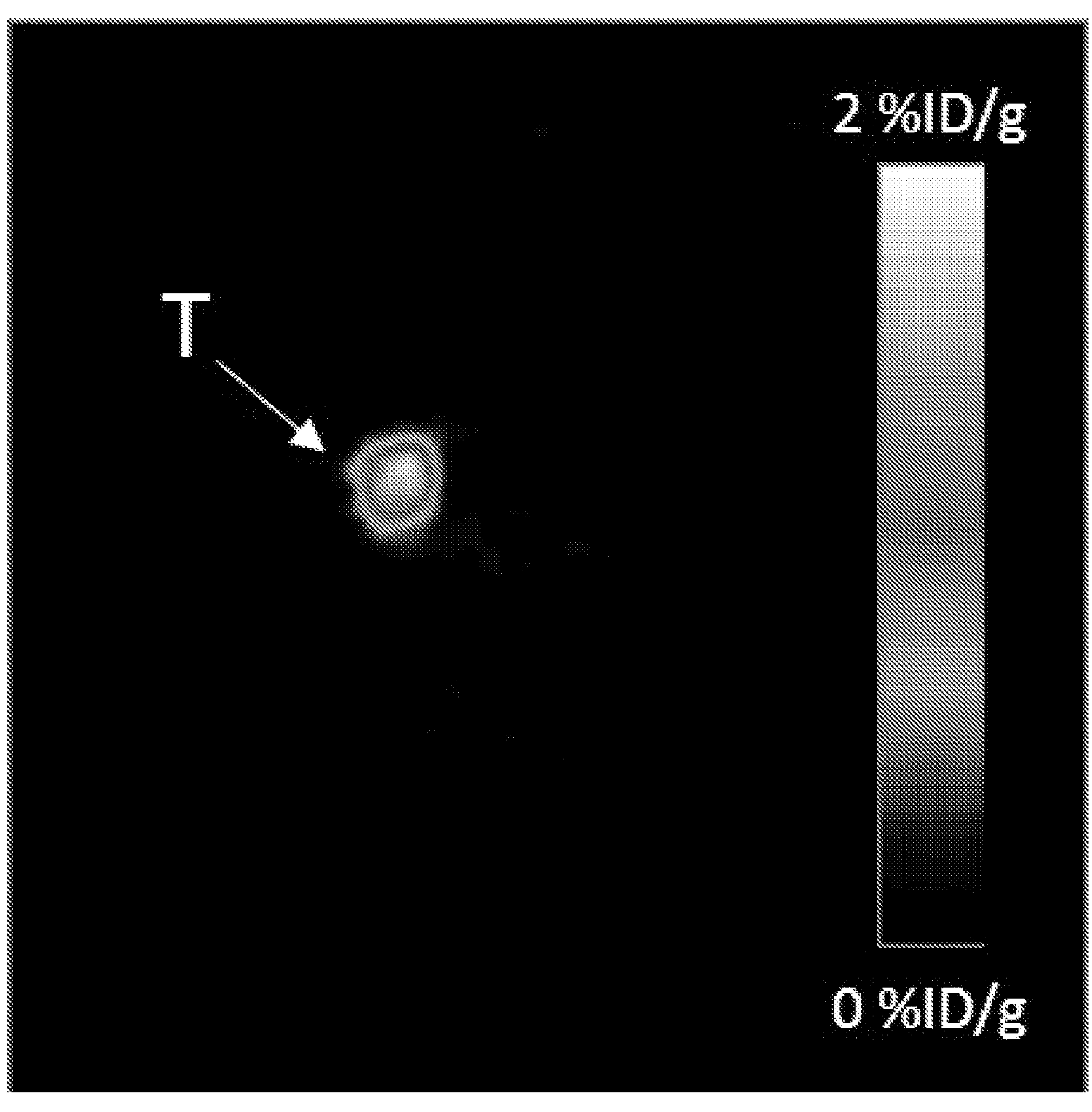
FIG. 11 shows a representative PET image (coronal) of a mouse that underwent PRIT with [$^{64}$Cu]NODAGA-PEG$_4$-LuDOTA. Images were obtained at ~24 hours post-injection of 300μ curies [$^{64}$Cu]NODAGA-PEG$_4$-LuDOTA. Tumor is clearly visible in the shoulder ("T").

[$^{64}$Cu]NODAGA-PEG$_4$-LuDOTA. Female athymic nude mice bearing s.c. GPA33-expressing SW1222 xenografts were administered 0.25 mg (1.19 nmol) of a HuA33-C825 BsAb at t=−28 h, followed with 16-N-acetylgalactosamine-DOTA(Y); 25 μg (2.76 nmol) at t=−4 h and [$^{64}$Cu] NODAGA-PEG$_4$-LuDOTA at t=0 h. FIG. 11 shows a representative PET image (coronal) of a mouse that underwent PRIT with [$^{64}$Cu]NODAGA-PEG$_4$-LuDOTA. Images were obtained at −24 hours post-injection of 300μ curies of [$^{64}$Cu]NODAGA-PEG$_4$-LuDOTA. Tumor is clearly visible in the shoulder ("T").

As shown in FIG. 10, in animals undergoing PRIT with BsAb huA33-C825 and [$^{64}$Cu]NODAGA-PEG$_4$-LuDOTA, the blood, tumor, and kidney uptakes at 24 hours after injection were 0.22±0.03% ID/g, 3.53±0.55% ID/g, and 0.41±0.03% ID/g, respectively, corresponding to tumor-to-organ activity ratios of about 15.8±1.7 and 8.6±0.7 for blood and kidney, respectively.

[$^{177}$Lu]DOTABn-PEG$_4$-LuDOTA. Groups of SW1222 tumor-bearing mice (n=4-6) were given 250 μg of huA33-C825, followed 24 h later with dendrimer-clearing agent (10% (w/w), 25 μg), and after an additional 4 h, [$^{177}$Lu]Lu-aminobenzylDOTA (illustrated below in Scheme 7) or [$^{177}$Lu]DOTABn-PEG$_4$-LuDOTA (also referred to herein as "[$^{177}$Lu]Lu-GeminiDOTA") was administered (see FIG. 12A for administered moles/activity). As shown in FIGS. 12A-12B, in animals undergoing PRIT with BsAb huA33-C825 and [$^{177}$Lu]DOTABn-PEG$_4$-LuDOTA, the blood, tumor, and kidney uptakes at 24 hours after injection were 0.14±0.02% ID/g, 5.07±0.38% ID/g, and 0.48±0.05% ID/g, respectively, corresponding to tumor-to-organ activity ratios of about 36.2±5.8 and 10.6±1.3 for blood and kidney, respectively. In addition, prolonged retention of [$^{177}$Lu] DOTABn-PEG$_4$-LuDOTA in the tumor has been observed (both via this data as well as other data) and is a significant advantage especially in terms of delivering a much higher dose of the [$^{177}$Lu]DOTABn-PEG$_4$-LuDOTA to solid tumors.

Scheme 7. [$^{177}$Lu]Lu-aminobenzylDOTA

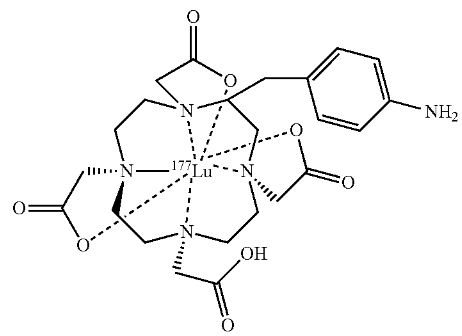

[$^{177}$Lu]Lu-aminobenzylDOTA

[$^{203}$Pb]TCMC-PEG$_4$-LuDOTA and [$^{203}$Pb]DO3A-PEG$_4$-LuDOTA. Groups of SW1222 tumor-bearing mice (n=4) were given 250 μg of huA33-C825, followed 24 h later with dendrimer-clearing agent (10% (w/w), 25 μg), and after an additional 4 h, [$^{203}$Pb]TCMC-PEG$_4$-LuDOTA (also referred to herein as "[$^{203}$Pb]TCMC-proteus-DOTA") or [$^{203}$Pb] DO3A-PEG$_4$-LuDOTA (also referred to herein as "[$^{203}$Pb] Proteus-DOTA") was administered (see FIG. 13 for administered moles/activity). The structure of [$^{203}$Pb]DO3A-PEG$_4$-LuDOTA is illustrated below in Scheme 8. See Int'l Appl. No. PCT/US2018/040911 filed Jul. 5, 2018, published as Int'l Publ. No. WO 2019/010299 A1 on Jan. 10, 2019, for more on [$^{203}$Pb]DO3A-PEG$_4$-LuDOTA.

Scheme 8. [$^{203}$Pb]DO3A-PEG$_4$-LuDOTA (also referred as "[$^{203}$Pb]Proteus-DOTA")

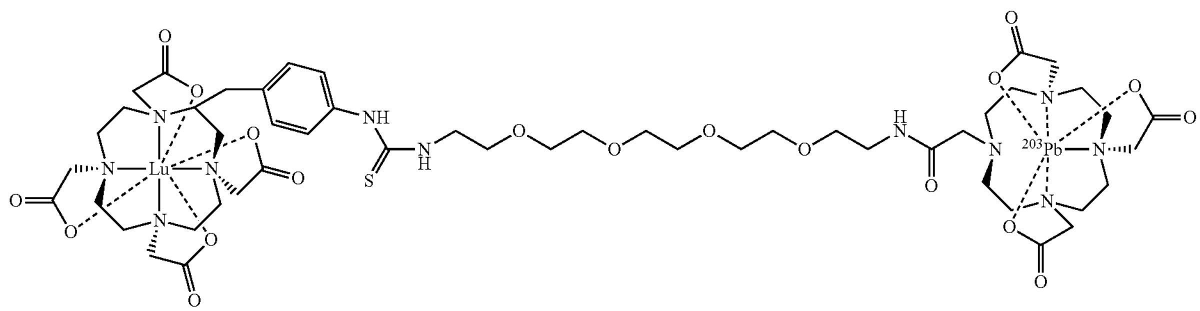

As shown in FIG. 13, in animals undergoing PRIT with BsAb huA33-C825 and [$^{203}$Pb]TCMC-proteus-DOTA, the blood, tumor, and kidney uptakes at 24 hours after injection were 0.31±0.12% ID/g, 27.79±7.38% ID/g, and 1.49±0.07% ID/g, respectively, corresponding to tumor-to-organ activity ratios of about 89.6±20.6 and 18.6±2.5 for blood and kidney, respectively.

As another comparison, groups of SW1222 tumor-bearing mice (n=4) were given 250 μg of huA33-C825, followed 24 h later with dendrimer-clearing agent (10% (w/w), 25 μg), and after an additional 4 h, either "[$^{111}$In]proteus-DOTA (Lu)" or "[$^{111}$In]proteus-DOTA(Gd)" (illustrated below in Scheme 9) was administered. See Int'l Appl. No. PCT/US2018/040911 filed Jul. 5, 2018, published as Int'l Publ. No. WO 2019/010299 A1 on Jan. 10, 2019, for more regarding [$^{111}$In]proteus-DOTA(Lu) and [$^{111}$In]proteus-DOTA(Gd).

Scheme 9. [$^{111}$In]proteus-DOTA(Lu) or [$^{111}$In]proteus-DOTA(Gd)

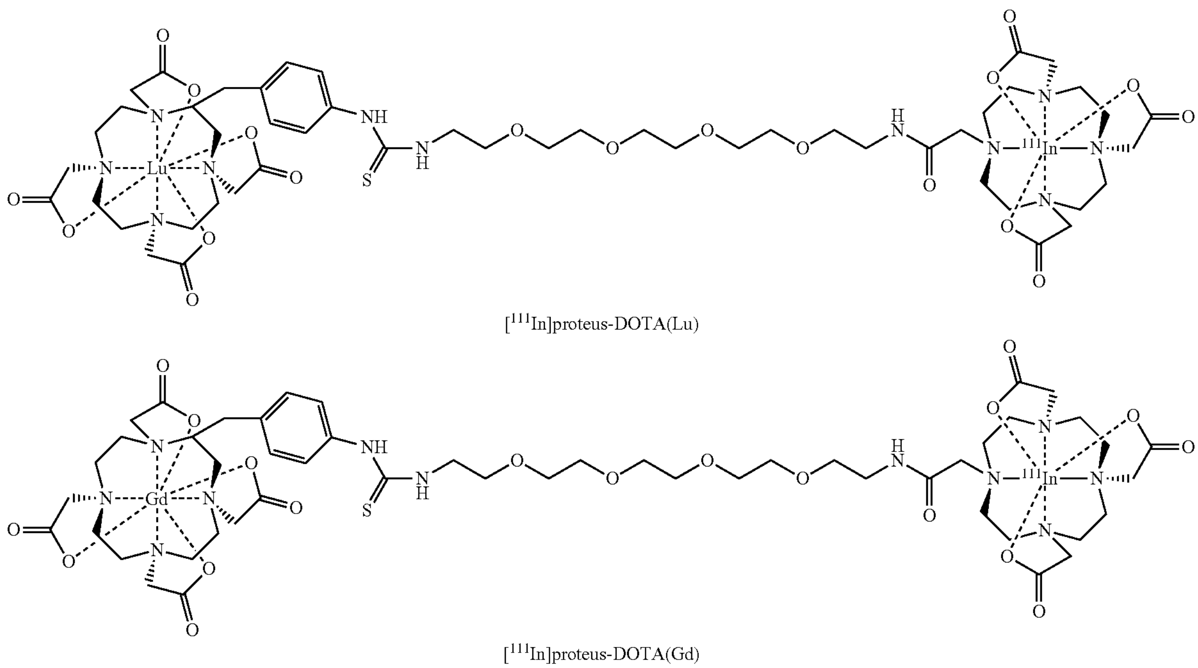

[$^{111}$In]proteus-DOTA(Lu)

[$^{111}$In]proteus-DOTA(Gd)

As shown in FIG. 14, in animals undergoing PRIT with BsAb huA33-C825 and [$^{111}$In]proteus-DOTA(Lu), the blood, tumor, and kidney uptakes at 24 hours after injection were 0.63±0.31% ID/g, 9.25±2.72% ID/g, and 0.67±0.13% ID/g, respectively, corresponding to tumor-to-organ activity ratios of about 14.6±4.2 and 13.9±2.5 for blood and kidney, respectively. FIG. 14 further illustrates that in animals undergoing PRIT with BsAb huA33-C825 and [$^{111}$In]proteus-DOTA(Gd), the blood, tumor, and kidney uptakes at 24 hours after injection were 0.46±0.21% ID/g, 7.66±4.74% ID/g, and 0.58±0.11% ID/g, respectively, corresponding to tumor-to-organ activity ratios of about 16.6±6.3 and 13.3±4.3 for blood and kidney, respectively.

These results demonstrates that the compositions of the present technology are useful for in vivo diagnostic imaging methods and pretargeted radioimmunotherapy.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I
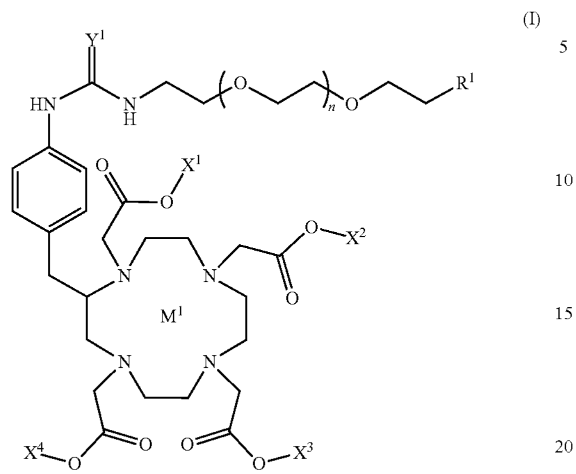
(I)
or a pharmaceutically acceptable salt thereof, wherein
$M^1$ is a chelated $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$ or $^{60}Gd^{3+}$;
$R^1$ is
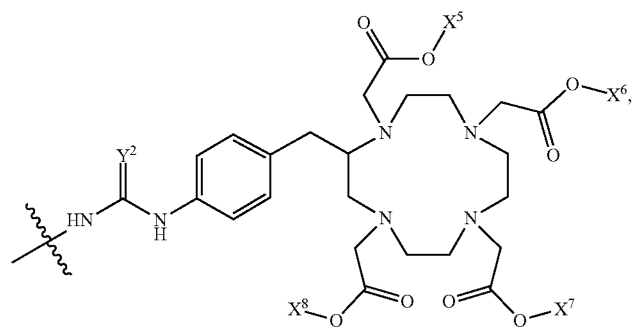
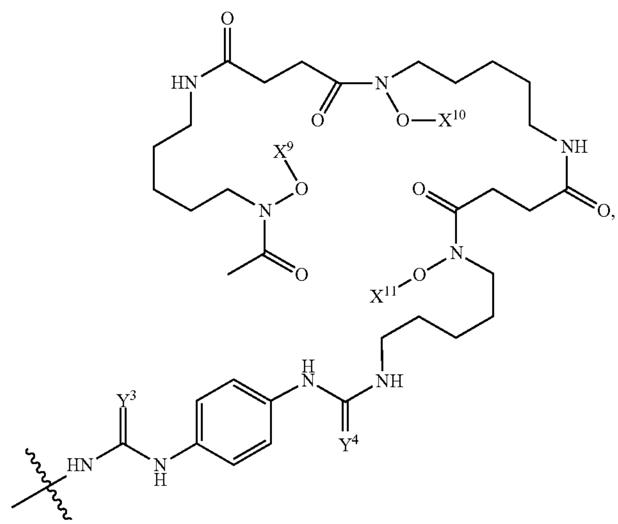
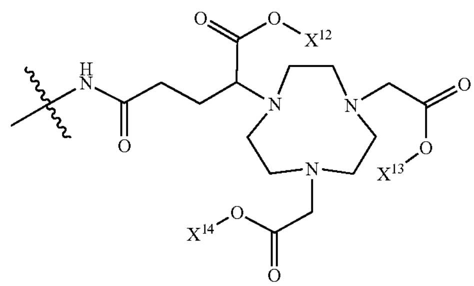

-continued
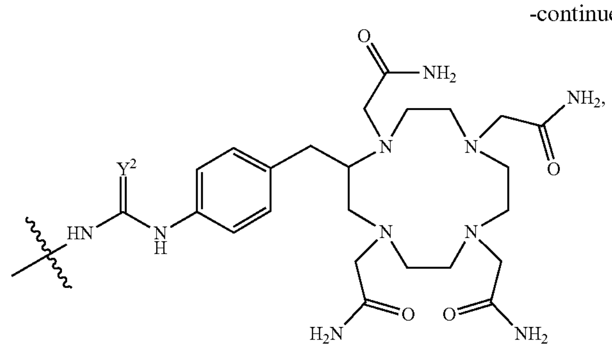
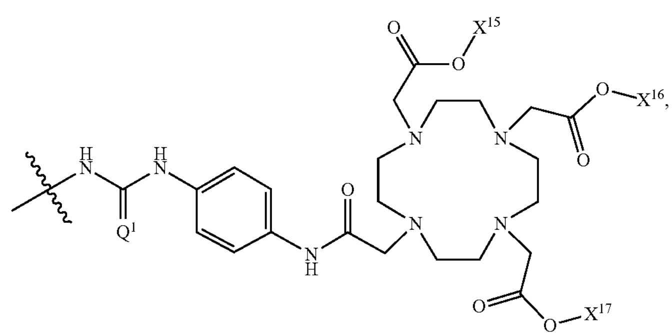
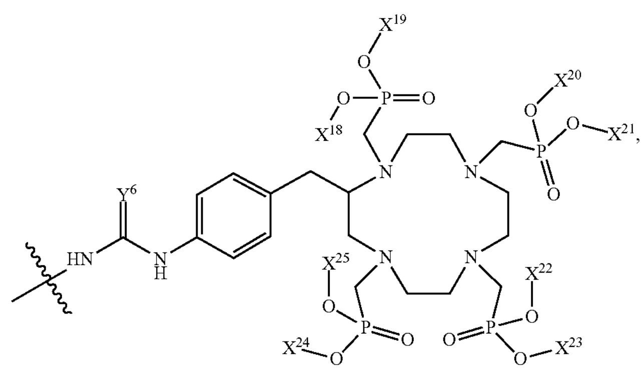
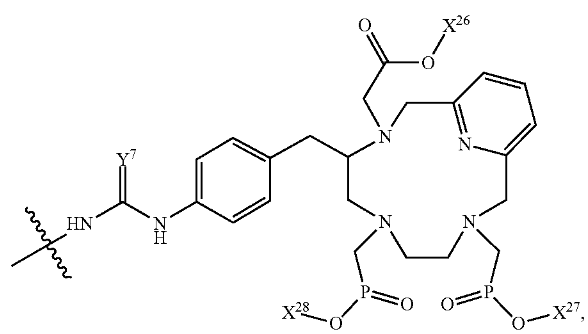

-continued

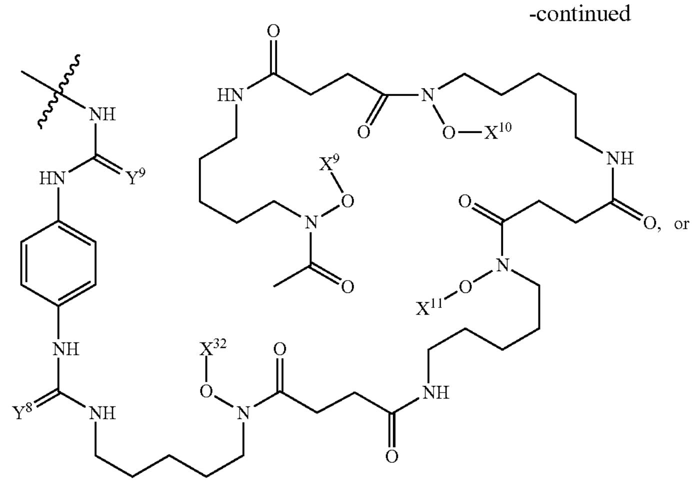

, or

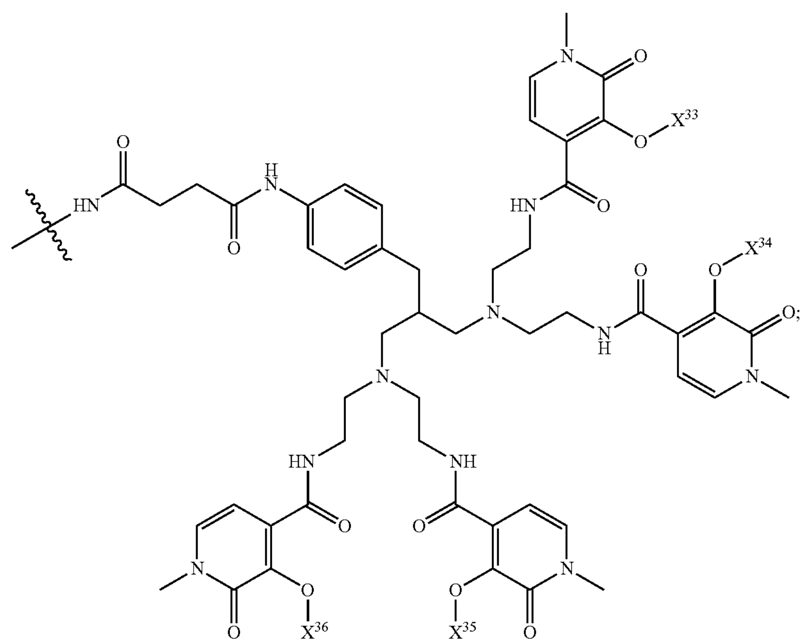

;

$X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, $X^{35}$, and $X^{36}$ are each independently a lone pair of electrons (i.e., providing an oxygen anion) or H;

$Y^1$, $Y^2$, $Y^3$, $Y^4$, $Y^5$, $Y^6$, $Y^7$, $Y^8$, and $Y^9$ are each independently S or O;

$Q^1$ is S or O; and n is 1, 2, 3, 4, 5, 6, 7, 8, 9, 10, 11, 12, 13, 14, 15, 16, 17, 18, 19, 20, 21, or 22.

B. A bischelate comprising the compound of Paragraph A and a radionuclide cation.

C. The bischelate of Paragraph B, wherein the bischelate is of Formula II (II)

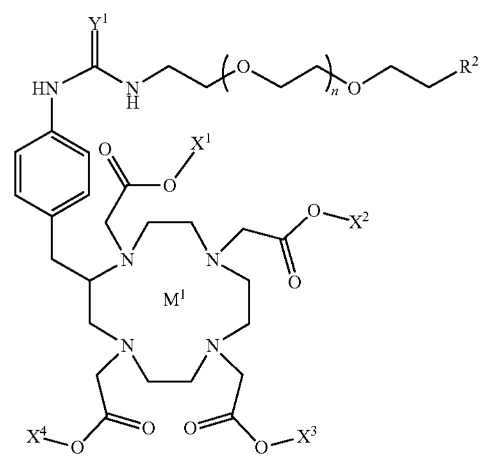

or a pharmaceutically acceptable salt thereof, wherein $M^1$ is a chelated $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $^{60}Gd^{3+}$;
$R^2$ is
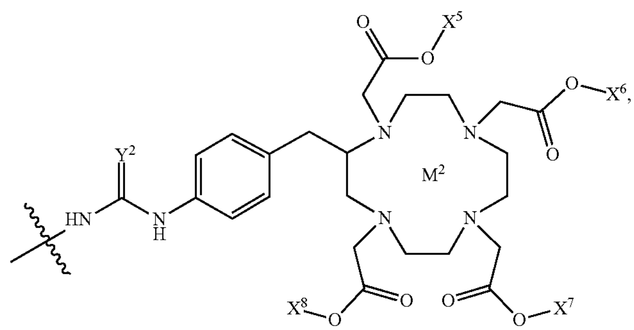
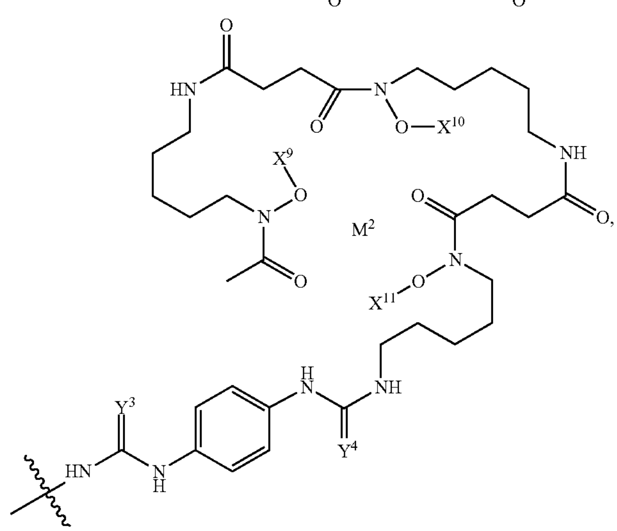
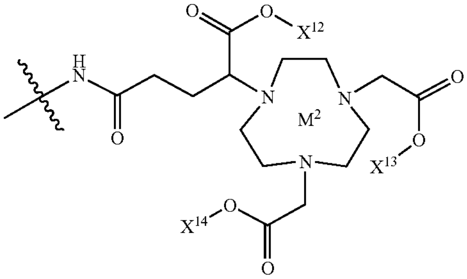
,
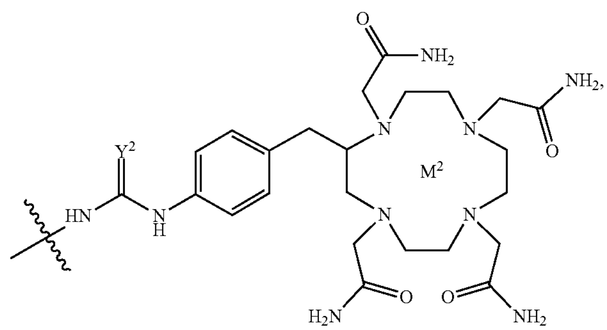
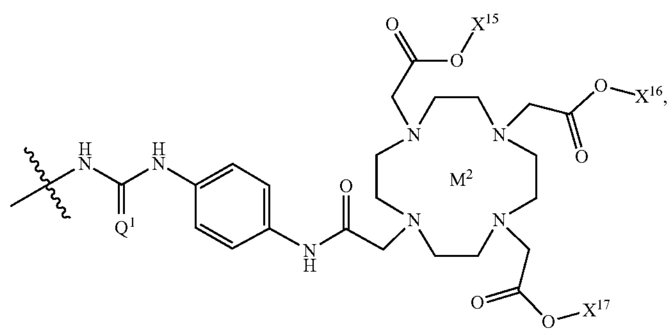

-continued
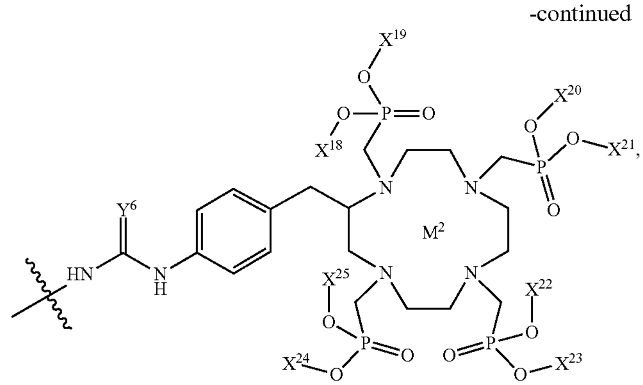
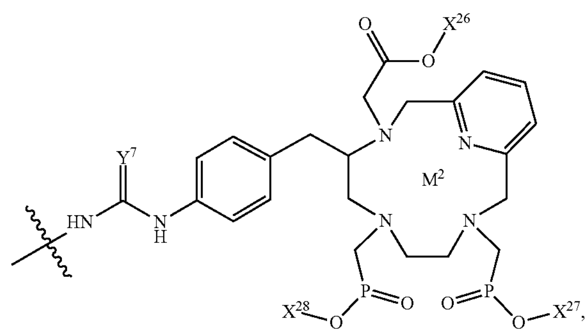
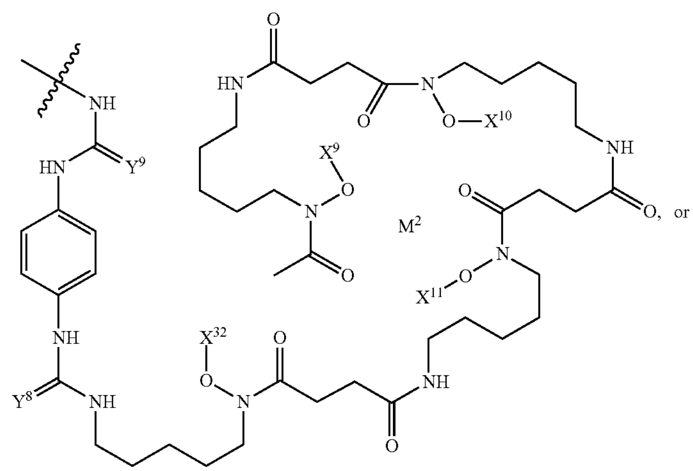
or

-continued

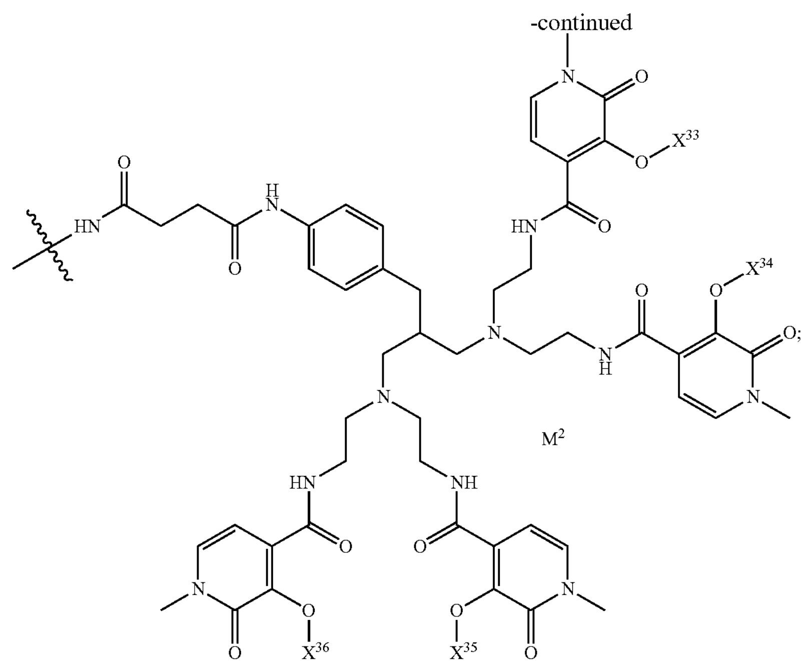

$M^2$ is independently at each occurrence a radionuclide cation chelated by the $R^2$ group;

$X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, $X^{35}$, and $X^{36}$ are each independently a lone pair of electrons (i.e., providing an oxygen anion) or H;

$Y^1$, $Y^2$, $Y^3$, $Y^4$, $Y^5$, $Y^6$, $Y^7$, $Y^8$, and $Y^9$ are each independently S or O;

$Q^1$ is S or O; and n is 1, 2, 3, 4, 5, 6, 7, 8, 9, 10, 11, 12, 13, 14, 15, 16, 17, 18, 19, 20, 21, or 22.

D. The bischelate of Paragraph C, wherein $M^2$ is an alpha particle-emitting isotope, a beta particle-emitting isotope, an Auger-emitter, or a combination of any two or more thereof.

E. The bischelate of Paragraph C or Paragraph D, wherein $M^2$ is $^{213}Bi$, $^{211}At$, $^{225}Ac$, $^{152}Dy$, $^{212}Bi$, $^{223}Ra$, $^{219}Rn$, $^{215}Po$, $^{211}Bi$, $^{221}Fr$, $^{217}At$, or $^{255}Fm$.

F. The bischelate of Paragraph C or Paragraph D wherein $M^2$ is $^{86}Y$, $^{90}Y$, $^{89}Sr$, $^{165}Dy$, $^{186}Re$, $^{188}Re$, $^{177}Lu$, or $^{67}Cu$.

G. The bischelate of Paragraph C or Paragraph D, wherein $M^2$ is $^{111}In$, $^{67}Ga$, $^{51}Cr$, $^{58}Co$, $^{99m}Tc$, $^{103m}Rh$, $^{195m}Pt$, $^{119}Sb$, $^{161}Ho$, $^{189m}Os$, $^{192}Ir$, $^{201}Tl$, or $^{203}Pb$.

H. The bischelate of Paragraph C or Paragraph D, wherein $M^2$ is $^{89}Zr$, $^{68}Ga$ $^{212}Pb$, $^{227}Th$, or $^{64}Cu$.

I. A complex comprising the compound of Paragraph A and a bispecific antibody that recognizes and binds to the compound and a tumor antigen target.

J. A complex comprising the bischelate of any one of Paragraphs B-H and a bispecific antibody that binds to the bischelate and a tumor antigen target.

K. The complex of Paragraph I or Paragraph J, wherein the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM.

L. The complex of Paragraph J or Paragraph K, wherein the bispecific antibody binds to the bischelate with a $K_d$ that is less than or equal to 100 nM-95 nM, 95-90 nM, 90-85 nM, 85-80 nM, 80-75 nM, 75-70 nM, 70-65 nM, 65-60 nM, 60-55 nM, 55-50 nM, 50-45 nM, 45-40 nM, 40-35 nM, 35-30 nM, 30-25 nM, 25-20 nM, 20-15 nM, 15-10 nM, 10-5 nM, 5-1 nM, 1 nM-950 pM, 950 pM-900 pM, 900 pM-850 pM, 850 pM-800 pM, 800 pM-750 pM, 750 pM-700 pM, 700 pM-650 pM, 650 pM-600 pM, 600 pM-550 pM, 550 pM-500 pM, 500 pM-450 pM, 450 pM-400 pM, 400 pM-350 pM, 350 pM-300 pM, 300 pM-250 pM, 250 pM-200 pM, 200 pM-150 pM, 150 pM-100 pM, 100 pM-50 pM, 50 pM-40 pM, 40 pM-30 pM, 30 pM-20 pM, 20 pM-10 pM, 9 pM, 8 pM, 7 pM, 6 pM, 5 pM, 4 pM, 3 pM, 2.5 pM, 2 pM, 1.5 pM, or 1 pM.

M. A method for detecting tumors in a subject in need thereof comprising (a) administering an effective amount of the complex of any one of Paragraphs J-K to the subject, wherein the complex is configured to localize to a tumor expressing the tumor antigen target recognized by the bispecific antibody of the complex; and (b) detecting the presence of tumors in the subject by detecting radioactive levels emitted by the complex that are higher than a reference value.

N. A method for selecting a subject for pretargeted radioimmunotherapy comprising (a) administering an effective amount of the complex of any one of Paragraphs J-K to the subject, wherein the complex is configured to localize to a tumor expressing the tumor antigen target recognized by the bispecific antibody of the complex;

(b) detecting radioactive levels emitted by the complex; and (c) selecting the subject for pretargeted radioimmunotherapy when the radioactive levels emitted by the complex are higher than a reference value.

O. The method of Paragraph M or Paragraph N, wherein the radioactive levels emitted by the complex are detected using positron emission tomography or single photon emission computed tomography.

P. The method of any one of Paragraphs M-O, wherein the subject is diagnosed with, or is suspected of having cancer.

Q. The method of Paragraph P, wherein the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, and head-and-neck cancer.

R. The method of Paragraph Q, wherein the brain cancer is a pituitary adenoma, a meningioma, a neuroblastoma, or a craniopharyngioma.

S. The method of any one of Paragraphs M-R, wherein the complex is administered into the cerebral spinal fluid or blood of the subject.

T. The method of any one of Paragraphs M-S, wherein the complex is administered intravenously, intramuscularly, intraarterially, intrathecally, intracapsularly, intraorbitally, intradermally, intraperitoneally, transtracheally, subcutaneously, intracerebroventricularly, orally or intranasally.

U. The method of any one of Paragraphs M-T, wherein the radioactive levels emitted by the complex are detected between 4 to 24 hours after the complex is administered.

V. The method of any one of Paragraphs M-U, wherein the radioactive levels emitted by the complex are expressed as the percentage injected dose per gram tissue (% ID/g).

W. The method of any one of Paragraphs M-V, wherein the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

X. A method for increasing tumor sensitivity to radiation therapy in a subject diagnosed with cancer comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of any one of Paragraphs B-H to the subject, wherein the bischelate is configured to bind to the anti-DOTA bispecific antibody.

Y. The method of Paragraph X, further comprising administering an effective amount of a clearing agent to the subject prior to administration of the bischelate.

Z. The method of Paragraph Y, wherein the clearing agent is a 500 kD aminodextran-DOTA conjugate.

AA. The method of any one of Paragraphs X-Z, wherein the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM.

AB. The method of any one of Paragraphs X-AA, wherein the anti-DOTA bispecific antibody is administered intravenously, intramuscularly, intraarterially, intrathecally, intracapsularly, intraorbitally, intradermally, intraperitoneally, transtracheally, subcutaneously, intracerebroventricularly, orally or intranasally.

AC. The method of any one of Paragraphs X-AB, wherein the bischelate is administered intravenously, intramuscularly, intraarterially, intrathecally, intracapsularly, intraorbitally, intradermally, intraperitoneally, transtracheally, subcutaneously, intracerebroventricularly, orally or intranasally.

AD. A method for increasing tumor sensitivity to radiation therapy in a subject diagnosed with cancer comprising administering an effective amount of the complex of any one of Paragraphs J-L to the subject, wherein the complex is configured to localize to a tumor expressing the tumor antigen target recognized by the bispecific antibody of the complex.

AE. The method of Paragraph AD, wherein the complex is administered intravenously, intramuscularly, intraarterially, intrathecally, intracapsularly, intraorbitally, intradermally, intraperitoneally, transtracheally, subcutaneously, intracerebroventricularly, orally or intranasally.

AF. A method for treating cancer in a subject in need thereof comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of any one of Paragraphs B-H to the subject, wherein the bischelate is configured to bind to the anti-DOTA bispecific antibody.

AG. The method of Paragraph AF, further comprising administering an effective amount of a clearing agent to the subject prior to administration of the bischelate.

AH. A method for treating cancer in a subject in need thereof comprising administering an effective amount of the complex of any one of Paragraphs J-L to the subject, wherein the complex is configured to localize to a tumor expressing the tumor antigen target recognized by the bispecific antibody of the complex.

AI. The method of any one of Paragraphs AF-AH, further comprising sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11.

AJ. The method of any one of Paragraphs X-AI, wherein the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, and head-and-neck cancer.

AK. A kit comprising a compound of Paragraph A, at least one anti-DOTA BsAb, and instructions for use.

AL. A kit comprising a bischelate of any one of Paragraphs B-H, at least one anti-DOTA BsAb, and instructions for use.

AM. The kit of Paragraph AK or Paragraph AL, further comprising a clearing agent and/or one or more radionuclides.

AN. The kit of Paragraph AM, wherein the clearing agent is a 500 kD aminodextran-DOTA conjugate.

Other embodiments are set forth in the following claims.

The invention claimed is:

1. A compound of Formula I (I)

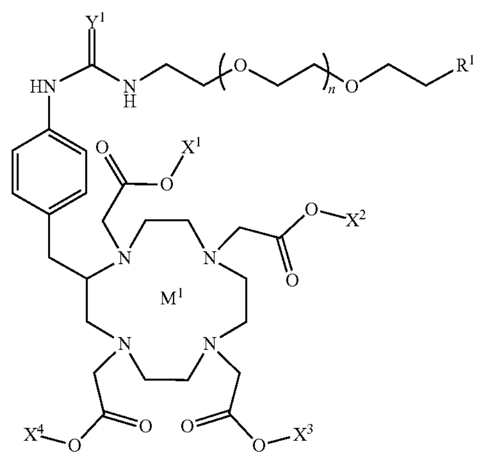

or a pharmaceutically acceptable salt thereof, wherein $M^1$ is a chelated $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$ or $^{60}Gd^{3+}$;

$R^1$ is

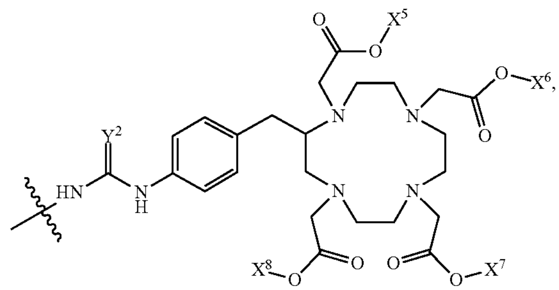

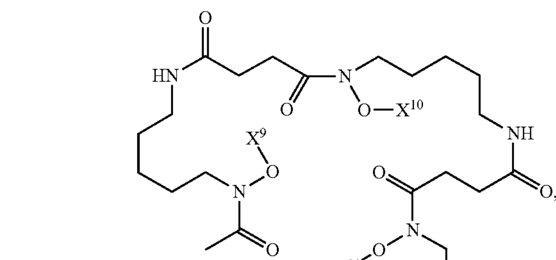

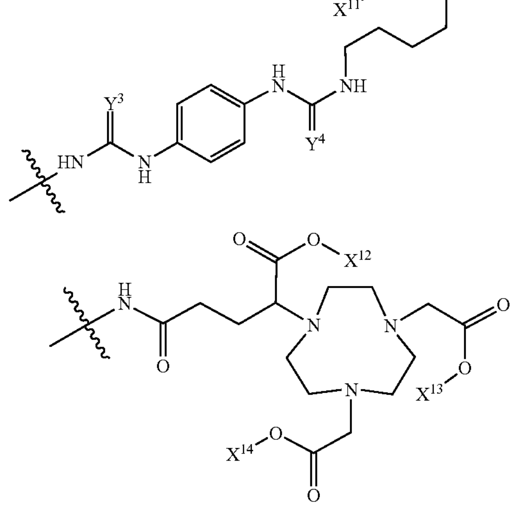

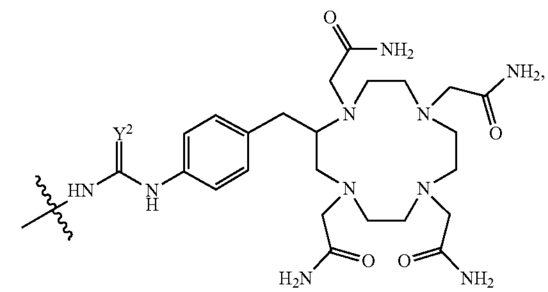

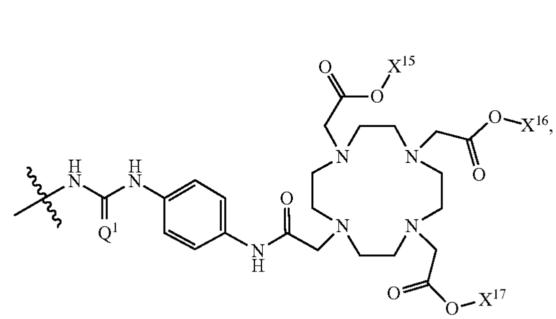

-continued

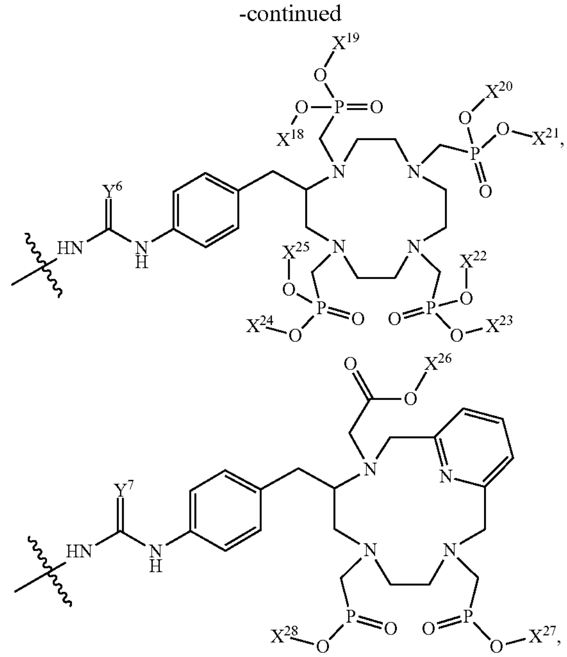

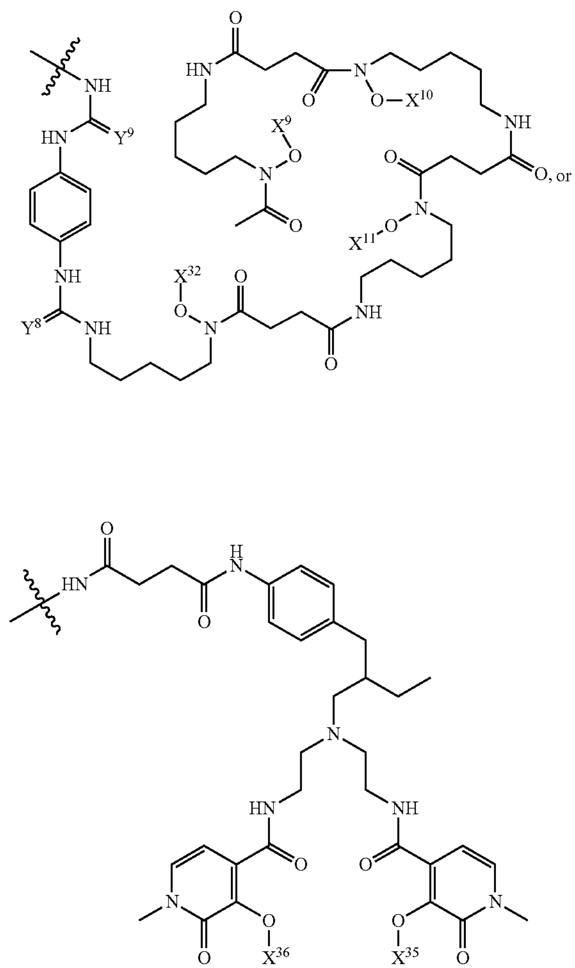

-continued

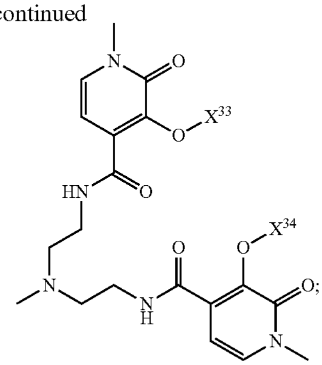

$X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, $X^{35}$, and $X^{36}$ are each independently a lone pair of electrons or H;

$Y^1$, $Y^2$, $Y^3$, $Y^4$, $Y^5$, $Y^6$, $Y^7$, $Y^8$, and $Y^9$ are each independently S or O;

$Q^1$ is S or O; and n is 1, 2, 3, 4, 5, 6, 7, 8, 9, 10, 11, 12, 13, 14, 15, 16, 17, 18, 19, 20, 21, or 22.

2. A bischelate comprising the compound of claim 1 and a radionuclide cation or wherein the bischelate is of Formula II (II)

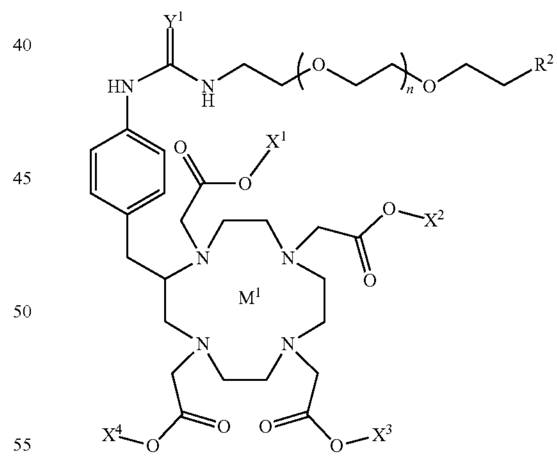

or a pharmaceutically acceptable salt thereof, wherein $M^1$ is a chelated $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $^{60}Gd^{3+}$;

$R^2$ is
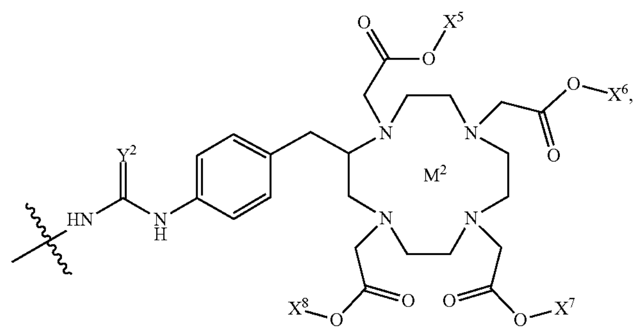
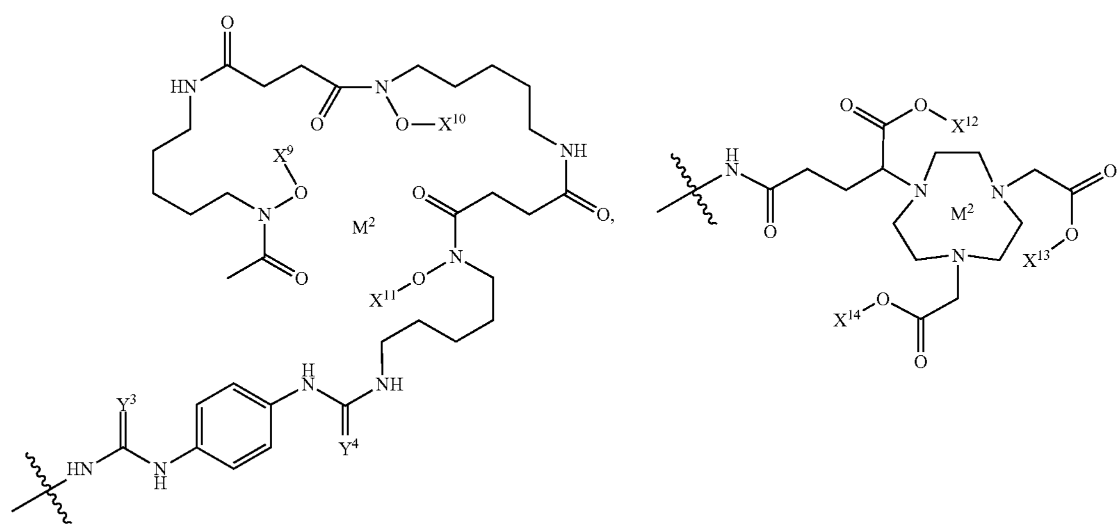
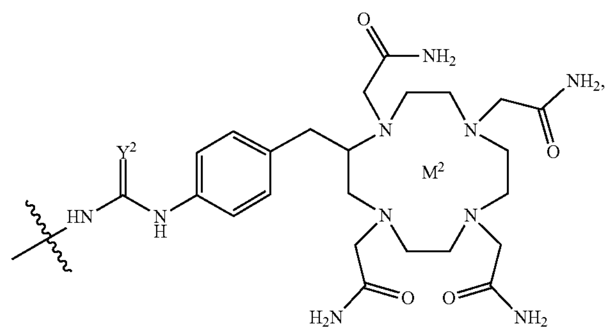
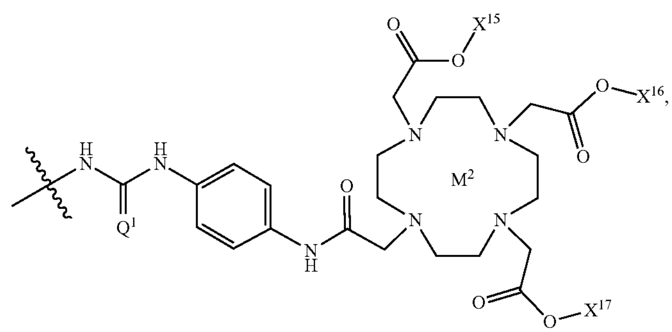

-continued
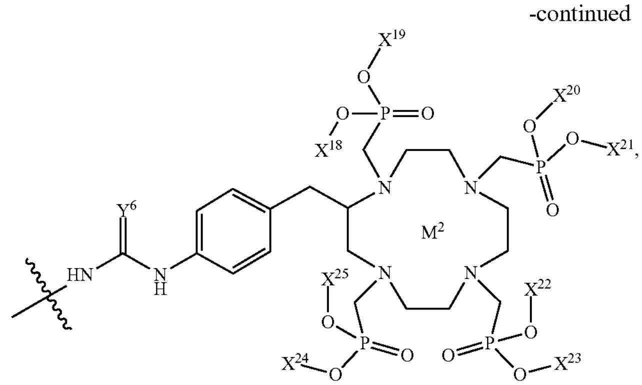
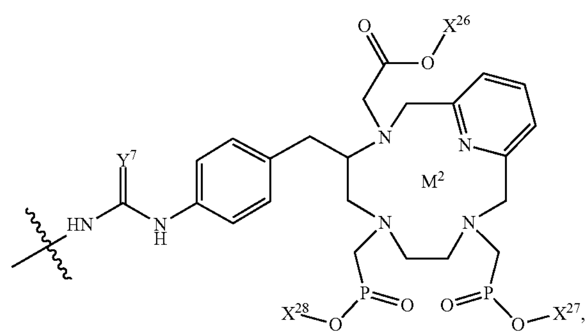
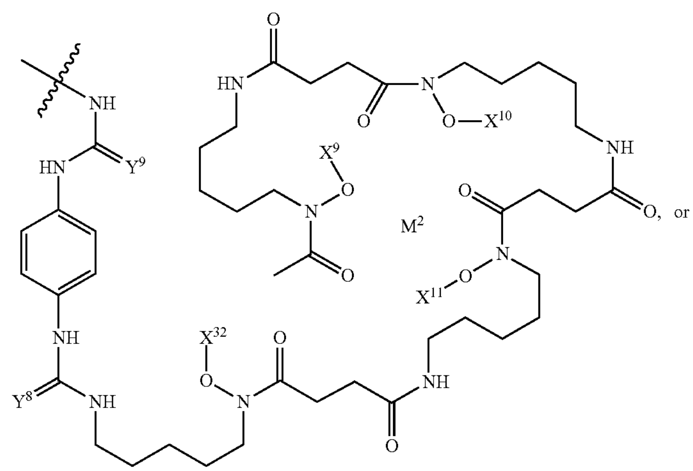
or

-continued

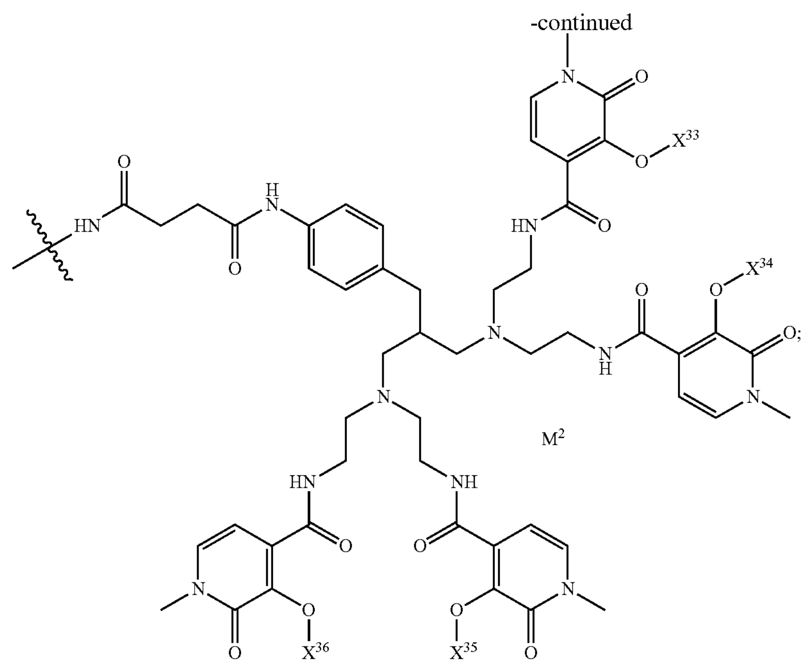

$M^2$ is independently at each occurrence a radionuclide cation chelated by the $R^2$ group;

$X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, $X^{35}$, and $X^{36}$ are each independently a lone pair of electrons or H;

$Y^1$, $Y^2$, $Y^3$, $Y^4$, $Y^5$, $Y^6$, $Y^7$, $Y^8$, and $Y^9$ are each independently S or O;

$Q^1$ is S or O; and n is 1, 2, 3, 4, 5, 6, 7, 8, 9, 10, 11, 12, 13, 14, 15, 16, 17, 18, 19, 20, 21, or 22.

3. The bischelate of claim 2, wherein $M^2$ is an alpha particle-emitting isotope, a beta particle-emitting isotope, an Auger-emitter, or a combination of any two or more thereof; or wherein $M^2$ is $^{213}Bi$, $^{211}At$, $^{225}Ac$, $^{152}Dy$, $^{212}Bi$, $^{223}Ra$, $^{219}Rn$, $^{215}Po$, $^{211}Bi$, $^{221}Fr$, $^{217}At$, or $^{255}Fm$; or wherein $M^2$ is $^{86}Y$, $^{90}Y$, $^{89}Sr$, $^{165}Dy$, $^{186}Re$, $^{188}Re$, $^{177}Lu$, or $^{67}Cu$; or wherein $M^2$ is $^{111}In$, $^{67}Ga$, $^{51}Cr$, $^{58}Co$, $^{99m}Tc$, $^{103m}Rh$, $^{195m}Pt$, $^{119}Sb$, $_{161}Ho$, $^{189m}Os$, $^{192}Ir$, $^{201}Tl$, or $^{203}Pb$; or wherein $M^2$ is $^{89}Zr$, $^{68}Ga$, $^{212}Pb$, $^{227}Th$, or $^{64}Cu$.

4. A complex comprising the compound of claim 1 and a bispecific antibody that recognizes and binds to the compound and a tumor antigen target.

5. A complex comprising the bischelate of claim 2 and a bispecificantibody that binds to the bischelate and a tumor antigen target, optionally wherein the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125, carcinoembryonic antigen, RAGE, MART, MUC-1, MUC-2, MUC-3, MUC-4, MUC-5ac, MUC-16, MUC-17, tyrosinase, Pmel 17, GnT-V intron V sequence, Prostate cancer psm, PRAME, β-catenin, EBNA 1-6, p53, lung resistance protein, Bcl-2, prostate specific antigen, Ki-67, CEACAM6, colon-specific antigen-p, HLA-DR, CD40, CD74, CD138, EGFR, EGP-1, EGP-2, VEGF, PIGF, insulin-like growth factor, tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y antigen, E-cadherin, V-cadherin, and EpCAM; or the bispecific antibody binds to the bischelate with a Kd that is less than or equal to 100 nM-95 nM, 95-90 nM, 90-85 nM, 85-80 nM, 80-75 nM, 75-70 nM, 70-65 nM, 65-60 nM, 60-55 nM, 55-50 nM, 50-45 nM, 45-40 nM, 40-35 nM, 35-30 nM, 30-25 nM, 25-20 nM, 20-15 nM, 15-10 nM, 10-5 nM, 5-1 nM, 1 nM-950 pM, 950 pM-900 pM, 900 pM-850 pM, 850 pM-800 pM, 800 pM-750 pM, 750 pM-700 pM, 700 pM-650 pM, 650 pM-600 pM, 600 pM-550 pM, 550 pM-500 pM, 500 pM-450 pM, 450 pM-400 pM, 400 pM-350 pM, 350 pM-300 pM, 300 pM-250 pM, 250 pM-200 pM, 200 pM-150 pM, 150 pM-100 pM, 100 pM-50 pM, 50 pM-40 pM, 40 pM-30 pM, 30 pM-20 pM, 20 pM-10 pM, 9 pM, 8 pM, 7 pM, 6 pM, 5 pM, 4 pM, 3 pM, 2.5 pM, 2 pM, 1.5 pM, or 1 pM.

6. A method for detecting tumors in a subject in need thereof comprising (a) administering an effective amount of the complex of claim 5 to the subject, wherein the complex is configured to localize to a tumor expressing the tumor antigen target recognized by the bispecific antibody of the complex; and (b) detecting the presence of tumors in the subject by detecting radioactive levels emitted by the complex that are higher than a reference value.

7. A method for selecting a subject for pretargeted radioimmunotherapy comprising (a) administering an effective amount of the complex of claim 5 to the subject, wherein the complex is configured to localize to a tumor expressing the tumor antigen target recognized by the bispecific antibody of the complex;

(b) detecting radioactive levels emitted by the complex; and (c) selecting the subject for pretargeted radioimmunotherapy when the radioactive levels emitted by the complex are higher than a reference value.

8. The method of claim 6, wherein the radioactive levels emitted by the complex are detected using positron emission tomography or single photon emission computed tomography; or wherein the subject is diagnosed with, or is suspected of having cancer, optionally wherein the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, head-and-neck cancer, pituitary adenoma, a meningioma, a neuroblastoma, or a craniopharyngioma.

9. The method of claim 7, wherein the radioactive levels emitted by the complex are detected using positron emission tomography or single photon emission computed tomography; or wherein the subject is diagnosed with, or is suspected of having cancer, optionally wherein the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, head-and-neck cancer, pituitary adenoma, a meningioma, a neuroblastoma, or a craniopharyngioma.

10. A method for increasing tumor sensitivity to radiation therapy in a subject diagnosed with cancer comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of claim 2 to the subject, wherein the bischelate is configured to bind to the anti-DOTA bispecific antibody.

11. The method of claim 10, further comprising administering an effective amount of a clearing agent to the subject prior to administration of the bischelate.

12. The method of claim 10, wherein the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125, carcinoembryonic antigen, RAGE, MART, MUC-1, MUC-2, MUC-3, MUC-4, MUC-5ac, MUC-16, MUC-17, tyrosinase, Pmel 17, GnT-V intron V sequence, Prostate cancer psm, PRAME, β-catenin, EBNA 1-6, p53, lung resistance protein, Bcl-2, prostate specific antigen, Ki-67, CEACAM6, colon-specific antigen-p, HLA-DR, CD40, CD74, CD138, EGFR, EGP-1, EGP-2, VEGF, PIGF, insulin-like growth factor, tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y antigen, E-cadherin, V-cadherin, and EpCAM; or wherein the anti-DOTA bispecific antibody and/or the bischelate is administered intravenously, intramuscularly, intraarterially, intrathecally, intracapsularly, intraorbitally, intradermally, intraperitoneally, transtracheally, subcutaneously, intracerebroventricularly, orally or intranasally.

13. A method for increasing tumor sensitivity to radiation therapy in a subject diagnosed with cancer comprising administering an effective amount of the complex of claim 5 to the subject, wherein the complex is configured to localize to a tumor expressing the tumor antigen target recognized by the bispecific antibody of the complex, optionally wherein the complex is administered intravenously, intramuscularly, intraarterially, intrathecally, intracapsularly, intraorbitally, intradermally, intraperitoneally, transtracheally, subcutaneously, intracerebroventricularly, orally or intranasally.

14. A method for treating cancer in a subject in need thereof comprising (a) administering an effective amount of an anti-DOTA bispecific antibody to the subject, wherein the anti-DOTA bispecific antibody is configured to localize to a tumor expressing a tumor antigen target; and (b) administering an effective amount of the bischelate of claim 2 to the subject, wherein the bischelate is configured to bind to the anti-DOTA bispecific antibody.

15. The method of claim 14, further comprising administering an effective amount of a clearing agent to the subject prior to administration of the bischelate.

16. A method for treating cancer in a subject in need thereof comprising administering an effective amount of the complex of claim 5 to the subject, wherein the complex is configured to localize to a tumor expressing the tumor antigen target recognized by the bispecific antibody of the complex.

17. The method of claim 14, further comprising sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein inhibitors, proteosome inhibitors, HDAC inhibitors, pro-apoptotic agents, methotrexate and CPT-11.

18. The method of claim 14, wherein the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, leukemia, lymphoma, and head-and-neck cancer.

19. A kit comprising a compound of claim 1, at least one anti-DOTA BsAb, and instructions for use, optionally wherein the kit further comprises a clearing agent and/or one or more radionuclides, optionally wherein the clearing agent is a 500 kD aminodextran-DOTA conjugate.

20. A kit comprising a bischelate of claim 2, at least one anti-DOTA BsAb, and instructions for use, optionally wherein the kit further comprises a clearing agent and/or one or more radionuclides, optionally wherein the clearing agent is a 500 kD aminodextran-DOTA conjugate.

* * * * *